US012661387B2

(12) United States Patent
Moebius et al.

(10) Patent No.: US 12,661,387 B2
(45) Date of Patent: Jun. 23, 2026

(54) IL-2/IL-15R BETA GAMMA AGONIST DOSING REGIMENS FOR TREATING CANCER OR INFECTIOUS DISEASES

(71) Applicant: CYTUNE PHARMA, Nantes (FR)

(72) Inventors: Ulrich Moebius, Gauting Unterbrunn (DE); David Bechard, Saint-Etienne de Montluc (FR); Irena Adkins, Prezletice (CZ); Nada Podzimkova, Jindrichuv Hradec (CZ)

(73) Assignee: Cytune Pharma, Nantes (FR)

( * ) Notice: Subject to any disclaimer, the term of this patent is extended or adjusted under 35 U.S.C. 154(b) by 1249 days.

(21) Appl. No.: 17/612,432

(22) PCT Filed: May 20, 2020

(86) PCT No.: PCT/EP2020/064132
§ 371 (c)(1),
(2) Date: Nov. 18, 2021

(87) PCT Pub. No.: WO2020/234387
PCT Pub. Date: Nov. 26, 2020

(65) Prior Publication Data
US 2022/0241375 A1      Aug. 4, 2022

(30) Foreign Application Priority Data

May 20, 2019   (EP) .................................... 19175436
May 28, 2019   (EP) .................................... 19177064

(51) Int. Cl.
| | |
|---|---|
| *A61K 38/20* | (2006.01) |
| *A61K 39/00* | (2006.01) |
| *A61K 39/395* | (2006.01) |
| *A61P 35/00* | (2006.01) |

(52) U.S. Cl.
CPC ...... *A61K 38/2013* (2013.01); *A61K 38/2086* (2013.01); *A61K 39/3955* (2013.01); *A61K 39/39558* (2013.01); *A61P 35/00* (2018.01); *A61K 2039/505* (2013.01); *A61K 2039/545* (2013.01); *A61K 2039/585* (2013.01)

(58) Field of Classification Search
CPC ............ A61K 38/2013; A61K 38/2086; A61K 39/3955; A61K 39/39558; A61K 2039/505; A61K 2039/545; A61K 2039/585; A61K 38/1793; A61K 2300/00; A61K 31/00; A61K 45/06; A61P 35/00; A61P 31/00; C07K 14/55; C07K 14/5443; C07K 14/7155; C07K 16/2818; C07K 16/2896
See application file for complete search history.

(56) References Cited

U.S. PATENT DOCUMENTS

| | | | |
|---|---|---|---|
| 5,229,109 | A | 7/1993 | Grimm et al. |
| 10,206,980 | B2 | 2/2019 | Qu et al. |
| 2003/0124678 | A1 | 7/2003 | Epstein et al. |
| 2006/0057680 | A1 | 3/2006 | Zheng et al. |
| 2007/0036752 | A1 | 2/2007 | Gillies et al. |
| 2015/0359853 | A1 | 12/2015 | Felber et al. |
| 2016/0175459 | A1 | 6/2016 | Gey et al. |
| 2016/0184399 | A1 | 6/2016 | Bechard et al. |
| 2017/0088597 | A1 | 3/2017 | Wong et al. |
| 2018/0118805 | A1 | 5/2018 | Bernett et al. |
| 2019/0092380 | A1 | 3/2019 | Miccinilli et al. |

FOREIGN PATENT DOCUMENTS

| | | | |
|---|---|---|---|
| WO | WO 2005/085282 | A1 | 9/2005 |
| WO | WO 2006/020849 | A2 | 2/2006 |
| WO | WO 2007/046006 | A2 | 4/2007 |
| WO | WO 2008/003473 | A2 | 1/2008 |
| WO | WO 2008/143794 | A1 | 11/2008 |
| WO | WO 2009/135031 | A1 | 11/2009 |
| WO | WO 2012/065086 | A1 | 5/2012 |
| WO | WO 2012/107417 | A1 | 8/2012 |
| WO | WO 2012/175222 | A1 | 12/2012 |
| WO | WO 2014/066527 | A2 | 5/2014 |
| WO | WO 2014/145806 | A2 | 9/2014 |
| WO | WO 2014/207173 | A1 | 12/2014 |
| WO | WO 2015/018528 | A1 | 2/2015 |
| WO | WO 2015/109124 | A2 | 7/2015 |
| WO | WO 2016/018920 | | 2/2016 |
| WO | WO 2016/060996 | A2 | 4/2016 |
| WO | 20180134784 | A1 | 7/2016 |
| WO | WO 2016/142314 | A1 | 9/2016 |
| WO | WO 2017/046200 | A1 | 3/2017 |
| WO | WO 2017/112528 | A2 | 6/2017 |

(Continued)

OTHER PUBLICATIONS

Tanigawa, K. et al. Current landscape and future prospects of interleukin-2 receptor (IL-2R) agonists in cancer immunotherapy. OncoImmunology (2025) (Year: 2025).*
Chillemi, A. et al. "Anti-CD38 antibody therapy: windows of opportunity yielded by the functional characteristics of the target molecule." Molecular Medicine (2013) (Year: 2013).*
Wu et al., An intermittent approach for cancer chemoprevention. Nat Rev Cancer 11, 879-885. Published Nov. 10, 2011, https://doi.org/10.1038/nrc3167 (2011).*
Wu et al., Immunogenic chemotherapy: Dose and schedule dependence and combination with immunotherapy, Cancer Letters, vol. 419, pp. 210-221, ISSN 0304-3835, https://doi.org/10.1016/j.canlet.2018.01.050. (2018).*
International Search Report for International Application No. PCT/EP2020/064132, mailed Aug. 24, 2020 (15 pages).

(Continued)

*Primary Examiner* — Jeffrey Stucker
(74) *Attorney, Agent, or Firm* — Kagan Binder, PLLC

(57) ABSTRACT

The present invention provides pulsed cyclic administration regimes and pulsed administration regimes for interleukin-2/interleukin-15 receptor βγ (IL-2/IL-15Rβγ) agonists for treating or managing cancer or infectious diseases in human patients. The administration regimes inter alia involve daily administration of IL-2/IL-15Rβγ agonists on 2, 3 or 4 consecutive days followed by days without administration.

18 Claims, 31 Drawing Sheets

Figure 1D:
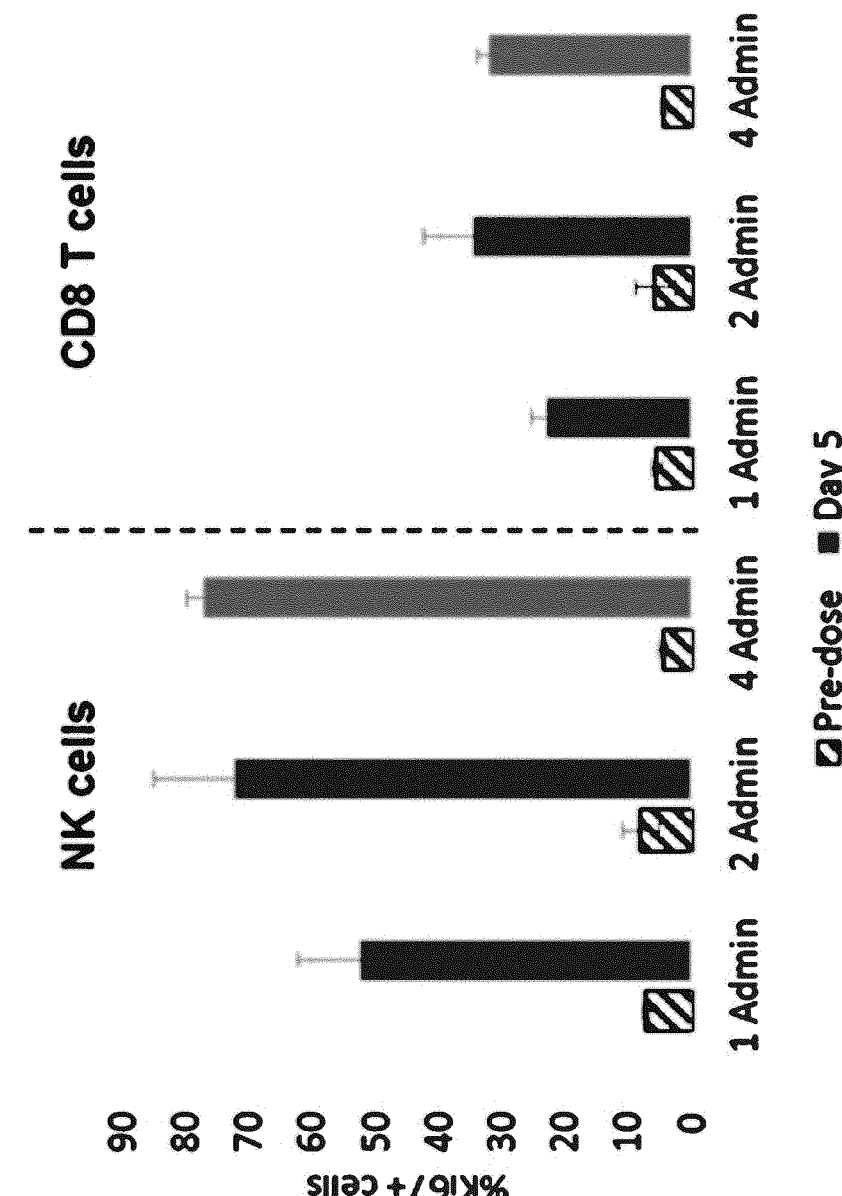

Specification includes a Sequence Listing.

(56) References Cited

FOREIGN PATENT DOCUMENTS

| WO | WO-2017103088 A1 * | 6/2017 | .............. A61P 29/00 |
| WO | WO 2018/071919 A | 4/2018 | |
| WO | WO 2018071918 A1 | 4/2018 | |
| WO | WO 2018/102536 A1 | 6/2018 | |
| WO | WO 2018/134782 A1 | 7/2018 | |
| WO | WO-2018134784 A1 * | 7/2018 | ......... A61K 38/1793 |
| WO | WO 2018/151868 A2 | 8/2018 | |
| WO | WO 2018/213341 A1 | 11/2018 | |
| WO | WO 2019/028419 A1 | 2/2019 | |
| WO | WO 2019/028425 A1 | 2/2019 | |
| WO | WO 2019/165453 A1 | 8/2019 | |
| WO | WO 2019/173798 A1 | 9/2019 | |

OTHER PUBLICATIONS

Abramson, H.N., "Monoclonal Antibodies for the Treatment of Multiple Myeloma: An Update," International Journal of Molecular Sciences, vol. 19, No. 12, Dec. 2018, pp. 31.

Bacac et al., "A Novel Carcinoembryonic Antigen T-Cell Bispecific Antibody (CEA TCB) for the Treatment of Solid Tumors," Clinical Cancer Research, vol. 22, No. 13, Feb. 2016, pp. 3286-3297.

Bacac et al., "Abstract No. 1594 Enhancement of the anti-tumor activity of CEA TCB via combination with checkpoint blockade by PD-L1 and interleukin-2 variant immunocytokine," Proceedings of the American Association for Cancer Research Annual Meeting, vol. 58, Apr. 2017, p. 408.

Beltra et al., "IL2Rβ-dependent signals drive terminal exhaustion and suppress memory development during chronic viral infection," Proceedings of the National Academy of Sciences of the United States of America (PNAS), vol. 113, No. 37, Aug. 2016, pp. E5444-E5453.

Bentebibel et al., "The Novel IL-2 Cytokine Immune Agonist NKTR-214 Harnesses the Adaptive and Innate Immune System for the Treatment of solid Cancers," Poster #P77, Society for Immunotherapy of Cancer 2017 Annual Meeting, National Harbor, MD, Nov. 2017, pp. 10.

Bergamaschi et al., "Optimized administration of hetIL-15 expands lymphocytes and minimizes toxicity in rhesus macaques," Cytokine, vol. 108, May 2018, pp. 213-224.

Bernett et al., "Abstract 1595: IL15/IL15Rα heterodimeric Fc-fusions with extended half-lives," Proceedings of the American Association for Cancer Research Annual Meeting, vol. 58, Apr. 2017, p. 408.

Caffaro et al., "Discovery of pharmacologically differentiated Interleukin 15 (IL-15) agonists employing a synthetic biology platform," Poster: P613, Society for Immunotherapy of Cancer (SITC) 2019 Annual Meeting, National Harbor, MD, Nov. 2019, pp. 2.

Castro et al., "The Basis of Distinctive IL-2- and IL-15-Dependent Signaling: Weak CD122-Dependent Signaling Favors CD8+ T Central-Memory Cell Survival but Not T Effector-Memory Cell Development," The Journal of Immunology, vol. 187, No. 10, Oct. 2011, pp. 5170-5182.

Charych et al., "Abstract No. 482: Tipping the balance in the tumor microenvironment: An engineered cytokine (NKTR-214) with altered IL2 receptor binding selectivity and improved efficacy," American Association for Cancer Research (AACR), Cancer Research, vol. 73, Issue 8 Supplement, Apr. 2013, pp. 4.

Charych et al., "Modeling the receptor pharmacology, pharmacokinetics, and pharmacodynamics of NKTR-214, a kinetically-controlled interleukin-2 (IL2) receptor agonist for cancer immunotherapy," PLoS ONE, vol. 12, No. 7, Jul. 2017, E0179431, pp. 24.

Charych et al., "NKTR-214, an Engineered Cytokine with Biased IL2 Receptor Binding, Increased Tumor Exposure, and Marked Efficacy in Mouse Tumor Models," Clinical Cancer Research, vol. 22, No. 3, Feb. 2016, pp. 680-690.

Chenoweth et al., "IL-15 Can Signal via IL-15Rα, JNK, and NF-κB to Drive RANTES Production by Myeloid Cells," The Journal of Immunology, vol. 188, No. 9, Mar. 2012, pp. 4149-4157.

Conlon et al., "Cytokines in the Treatment of Cancer," Journal of Interferon & Cytokine Research, vol. 39, No. 1, Jan. 2019, pp. 6-21.

Conlon et al., "Phase I/lb study of NIZ985 with and without spartalizumab (PDR001) in patients with metastatic/unresectable solid tumors," American Association for Cancer Research (AACR) Annual Meeting, Atlanta, GA, Mar. 2019, pp. 1.

Conlon et al., "Redistribution, Hyperproliferation, Activation of Natural Killer Cells and CD8 T Cells, and Cytokine Production During First-in-Human Clinical Trial of Recombinant Human Interleukin-15 in Patients With Cancer," Journal of Clinical Oncology, vol. 33, No. 1, Jan. 2015, on-line Nov. 2014, pp. 74-82 and appendix pp. 8.

Darvin et al., "Immune checkpoint inhibitors: recent progress and potential biomarkers," Experimental & Molecular Medicine, vol. 50, No. 12, Dec. 2018, pp. 1-11.

De Sousa et al., "Not All Immune Checkpoints Are Created Equal," Frontiers in Immunology, vol. 9, No. 1909, Aug. 2018, pp. 15.

Edgar, R.C., "Muscle: multiple sequence alignment with high accuracy and high throughput," Nucleic Acids Research, vol. 32, No. 5, Mar. 2004, pp. 1792-1797.

Elpek et al., "Mature natural killer cells with phenotypic and functional alterations accumulate upon sustained stimulation with IL-15/IL-15Rα complexes," Proceedings of National Academy of Sciences of the United States of America (PNAS), vol. 107, No. 50, Nov. 2010, pp. 21647-21652.

Felices et al., "Continuous treatment with IL-15 exhausts human NK cells via a metabolic defect," JCI Insight, vol. 3, No. 3, Feb. 2018, e96219, pp. 14.

Frutoso et al., "Emergence of NK Cell Hyporesponsiveness after Two IL-15 Stimulation Cycles," The Journal of Immunology, vol. 201, No. 2, May 2018, pp. 493-506.

Fyfe et al., "Results of Treatment of 255 Patients With Metastatic Renal Cell Carcinoma Who Received High-Dose Recombinant Interleukin-2 Therapy," Journal of Clinical Oncology, vol. 13, No. 3, Mar. 1995, pp. 688-696.

Gajewski et al., "Cancer immunotherapy strategies based on overcoming barriers within the tumor microenvironment," Current Opinion in Immunology, vol. 25, No. 2, Apr. 2013, pp. 268-276.

Gearing et al., "The international standard for human interleukin-2: Calibration by international collaborative study," Journal of Immunological Methods, vol. 114, No. 1-2, Nov. 1988, pp. 3-9.

Ghasemi et al., "Selective targeting of IL-2 to NKG2D bearing cells for improved immunotherapy," Nature Communications, vol. 7, Article No. 12878, Sep. 2016, pp. 15.

Giron-Michel et al., "Membrane-bound and soluble IL-15/IL-15Rα complexes display differential signaling and functions on human hematopoietic progenitors," Blood, vol. 106, No. 7, Oct. 2005, pp. 2302-2310.

Goujon et al., "A new bioinformatics analysis tools framework at EMBL-EBI," Nucleic Acids Research, vol. 38, Issue Suppl_2, May 2010, pp. W695-W699.

"Guidance for Industry—Estimating the Maximum Safe Starting Dose in Initial Clinical Trials for therapeutics in Adult Healthy Volunteers," by U.S. Department of Health and Human Services Food and Drug Administration—Center for Drug Evaluation and Research (CDER), Jul. 2005, pp. 30.

Han et al., "IL-15:IL-15 receptor alpha superagonist complex: High-level co-expression in recombinant mammalian cells, purification and characterization," Cytokine, vol. 56, No. 3, Oct. 2011, pp. 804-810.

Hangasky et al., "Interleukin 15 Pharmacokinetics and Consumption by a Dynamic Cytokine Sink," Frontiers in Immunology, vol. 13, No. 1813, Aug. 2020, pp. 5.

Harland et al., "Epigenetic plasticity of Cd8a locus during DC8+ T-cell development and effector differentiation and reprogramming," Nature Communications, vol. 5, Article No. 3547, Mar. 2014, pp. 13.

Heaton et al., "Human interleukin 2 Analogues that preferentially bind the intermediate-affinity interleukin 2 receptor lead to reduced secondary cytokine section: Implications for the use of these interleukin 2 analogues in cancer immunotherapy," Cancer Research, vol. 53, No. 11, Jun. 1993, pp. 2597-2602.

(56)                    References Cited

OTHER PUBLICATIONS

Hori et al., "Establishment of an Interleukin 2-Dependent Human T Cell Line From a Patient With T Cell Chronic Lymphocytic Leukemia Who is Not Infected With Human T Cell Leukemia/Lymphoma Virus," Blood, vol. 70, No. 4, Oct. 1987, pp. 1069-1072.

Hu et al., "Generation of low-toxicity interleukin-2 fusion proteins devoid of vasopermeability activity," Blood, vol. 101, No. 12, Jun. 2003, pp. 4853-4861.

Joseph et al., "Abstract No. 3258—THOR-707, a novel not-alpha IL-2, elicits durable pharmacodynamic responses in non-human primates and efficacy as single agent and in combination with anti PD-1 in multiple syngeneic mouse models," Proceedings of the American Association for Cancer Research Annual Meeting, vol. 60, Mar. 2019, pp. 838.

Klein, C., "S41. Novel CEA-targeted IL2 variant immunocytokine for immunotherapy of cancer," Journal for Immuno Therapy of Cancer, vol. 2, Issue Suppl. 2, Mar. 2014, p. I8-I8.

Klein et al., "Abstract PR8: Novel tumor-targeted, engineered IL-2 variant (IL-2v)-based immunocytokines for immunotherapy of cancer," Proceedings of the AACR Special Conference on Tumor Immunology: Multidisciplinary Science Driving Basic and Clinical Advances, Miami, FL, Dec. 2012, Cancer Research, vol. 73, Issue 1-Supplment, Jan. 2013, pp. 4.

Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, vol. 6, No. 3, Jan. 2017, e1277306, pp. 15.

Kurowska et al., "Fibroblast-Like Synoviocytes from Rheumatoid Arthritis Patients Express Functional IL-15 Receptor Complex: Endogenous IL-15 in Autocrine Fashion Enhances Cell Proliferation and Expression of Bcl-xL and Bcl-2," Journal of Immunology, vol. 169, No. 4, Aug. 2002, pp. 1760-1767.

Larsen et al., "NK Cells in the Tumor Microenvironment," Critical Reviews™ in Oncogenesis, vol. 19, No. 1-2, Apr. 2014, pp. 91-105.

Lazear et al., "Targeting of IL-2 to cytotoxic lymphocytes as an improved method of cytokine-driven immunotherapy," Oncoimmunology, vol. 6, No. 2, Jan. 2017, e1265721, pp. 3.

Liu et al., "Evaluation of the biological activities of the IL-15 superagonist complex, ALT-803, following intravenous versus subcutaneous administration in murine models," Cytokine, vol. 107, Feb. 2018, pp. 105-112.

Margolin et al., "Phase 1 Trial of ALT-803, A Novel Recombinant IL15 Complex, in Patients with Advanced Solid Tumors," Clinical Cancer Research, vol. 24, No. 22, Jul. 2018, pp. 5552-5561.

Mathios et al., "Therapeutic administration of IL-15 superagonist complex ALT-803 leads to long-term survival and durable antitumor immune response in a murine glioblastoma model," International Journal of Cancer, vol. 138, No. 1, Jul. 2015, pp. 187-194.

Miller et al., "A First-in-Human Phase 1 Study of Subcutaneous Outpatient Recombinant Human IL15 (rhIL15) in Adults with Advanced Solid Tumors," Clinical Cancer Research, vol. 24, No. 7, Dec. 2017, pp. a525-a1535.

Miyazaki et al., "Pharmacokinetic and Pharmacodynamic Study of NKTR-255, a Polymer-Conjugated Human IL-15, in Cynomolgus Monkey," Blood, vol. 132, Issue Supplement 1, Nov. 2018, pp. 2952.

Nct01021059, "A Phase I Study of Intravenous Recombinant Huma IL-15 in Adults With Refractory Metastatic Malignant Melanoma and Metastatic Renal Cell Cancer," accessed from www.clinicaltrials.gov as of May 14, 2019, 9 pages.

NCT01572493, "Continuous Infusion of rhIL-15 for Adults With Advanced Cancer," accessed from www.clinicaltrials.gov as of Aug. 16, 2018, 8 pages.

NCT02627274, A Study Evaluating Safety, Pharmacokinetics, and Therapeutic Activity of RO6874281 as a Single Agent (Part A) or in in Combination With Trastuzumab or Cetuximab (Part B or C), accessed from www.clinicaltrials.gov as of Jul. 30, 2024, 15 pages.

NCT02983045, "A Dose Escalation and Cohort Expansion Study of CD122-Biased Cytokine (NKTR-214) in Combination With Anti-PD-1 Antibody (Nivolumab) or in Combination With Nivolumab and Anti-CTLA4 Antibody (Ipilimumab) in Patients With Selected Advanced or Metastatic Solid Tumors (PIVOT-02)," accessed from www.clinicaltrials.gov as of Aug. 16, 2018, 13 pages.

NCT03063762, "Study to Evaluate Safety, Pharmacokinetics and Therapeutic Activity of RO6874281 as a Combination Therapy in Participants With Unresectable Advanced and/or Metastatic Renal Cell Carcinoma (RCC)," accessed from www.clinicaltrials.gov as of Aug. 16, 2018, 16 pages.

NCT03214666, "GTB-3550 (CD16/IL-15/CD33) Tri-Specific Killer Engager (TriKE™) for High Risk Heme Malignancies," accessed from www.clinicaltrials.gov as of Nov. 25, 2019, 8 pages.

NCT03386721, "Study to Evaluate the Therapeutic Activity of RO6874281 as a Combination Therapy in Participants With Advanced and/or Metastatic Solid Tumors," accessed from www.clinicaltrials.gov as of Aug. 16, 2018, 13 pages.

NCT03388632, "Recombinant Interleukin-15 in Combination With Checkpoint Inhibitors Nivolumab and Ipilimumab in People With Refractory Cancers," accessed from www.clinicaltrials.gov as of Aug. 16, 2018, 11 pages.

Needleman et al., "A General Method Applicable to the Search for Similarities in the Amino Acid Sequence of Two Proteins," Journal of Molecular Biology, vol. 48, No. 3, Mar. 1970, pp. 443-453.

Pearson et al., "Improved tools for biological sequence comparison," Proceedings of the National Academy of Sciences of the United States of America, vol. 85, No. 8, Apr. 1988, pp. 2444-2448.

Perdreau et al., "Different dynamics of IL-15R activation following IL-15 cis- or trans-presentation," European Cytokine Network, vol. 21, No. 4, Nov. 2010, pp. 297-307.

Rhode et al., "Comparison of the Superagonist Complex, ALT-803, to IL15 as Cancer Immunotherapeutics in Animal Models," Cancer Immunology Research, vol. 4, No. 1, Oct. 2015, pp. 49-60.

Ring et al., "Mechanistic and structural insight into the functional dichotomy between interleukin-2 and interleukin-15," Nature Immunology, vol. 13, No. 12, Oct. 2012, pp. 1187-1195.

Robinson et al., "The potential and promise of IL-15 in immune-oncogenic therapies," Immunology Letters, vol. 190, Aug. 2017, pp. 159-168.

Romee et al., "First-in-human phase 1 clinical study of the IL-15 superagonist complex ALT-803 to treat relapse after transplantation," Blood, vol. 131, No. 23, Feb. 2018, pp. 2515-2527.

Rosenzwajg et al., "Immunological and clinical effects of low-dose interleukin-2 across 11 autoimmune diseases in a single, open clinical trial," Annuals of the Rheumatic Diseases, vol. 78, No. 2, Nov. 2018, pp. 209-217.

Shanafelt et al., "A T-cell-selective interleukin 2 mutein exhibits potent antitumor activity and is well tolerated in vivo," Nature Biotechnology, vol. 18, No. 11, Nov. 2000, pp. 1197-1202.

Silva et al., "De novo design of potent and selective mimics of IL-2 and IL-15," Nature, vol. 565, No. 7738, Jan. 2019, pp. 186-191 and Supplementary Information pp. 16.

Smith et al., "Comparison of Biosequences," Advances in Applied Mathematics, vol. 2, No. 4, Dec. 1981, pp. 482-489.

Solomon et al., "TIGIT: a novel immunotherapy target moving from bench to bedside," Cancer Immunology, Immunotherapy, vol. 67, No. 11, Sep. 2018, pp. 1659-1667.

Soman et al., "MTS dye based colorimetric CTLL-2 cell proliferation assay for product release and stability monitoring of Interleukin-15: Assay qualification, standardization and statistical analysis," Journal of Immunological Methods, vol. 348, Nos. 1-2, Aug. 2009, pp. 83-94.

Steel et al., "Interleukin-15 biology and its therapeutic implications in cancer," Trends in Pharmacological Sciences, vol. 33, No. 1, Jan. 2012, pp. 35-41.

Thaysen-Andersen et al., "Recombinant human heterodimeric IL-15 complex displays extensive and reproducible N- and O-linked glycosylation," Glycoconjugate Journal, vol. 33, No. 3, Nov. 2015, pp. 417-433.

Toutain et al., "Plasma terminal half-life," Journal of Veterinary Pharmacology and Therapeutics, vol. 27, No. 6, Dec. 2004, pp. 427-439.

(56) References Cited

OTHER PUBLICATIONS

Wadhwa et al., "The 2nd International standard for Interleukin-2 (IL-2) Report of a collaborative study," Journal of Immunological Methods, vol. 397, Nos. 1-2, Aug. 2013, pp. 1-7.

Waldmann, T.A., "The Shared and Contrasting Roles of IL2 and IL15 in the Life and Death of Normal and Neoplastic Lymphocytes: Implications for Cancer therapy," Cancer Immunology Research, vol. 3, No. 3, Mar. 2015, pp. 219-227.

Wei et al., "The Sushi Domain of Soluble IL-15 Receptor a is Essential for Binding IL-15 and Inhibiting Inflammatory and Allogenic Responses In Vivo," Journal of Immunology, vol. 167, No. 1, Jul. 2001, pp. 277-282.

Wrangle et al., "ALT-803, an IL-15 superagonist, in combination with nivolumab in patients with metastatic non-small cell lung cancer: a non-randomised, open-label, phase 1b trial," Lancet Oncology, vol. 19, No. 5, Apr. 2018, pp. 694-704.

Champiat et al., "Nanrilkefusp alfa (SOT101), an IL-15 receptor βY superagonist, as a single agent or with anti-PD-1 in patients with advanced cancers," Cell Reports Medicine, vol. 2, No. 2, Feb. 2025, 23 pp.

* cited by examiner

Fig. 1 A

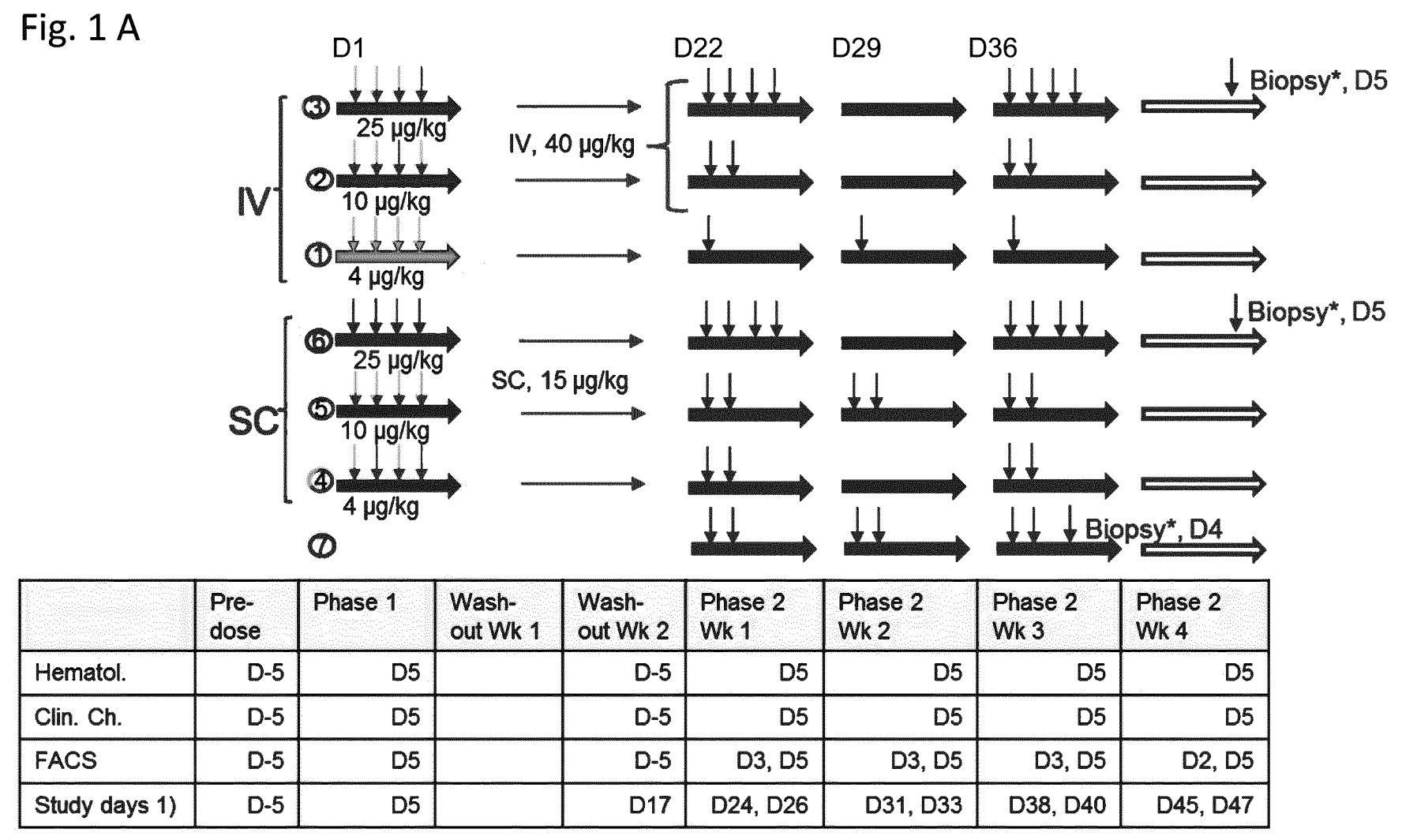

| | Pre-dose | Phase 1 | Wash-out Wk 1 | Wash-out Wk 2 | Phase 2 Wk 1 | Phase 2 Wk 2 | Phase 2 Wk 3 | Phase 2 Wk 4 |
|---|---|---|---|---|---|---|---|---|
| Hematol. | D-5 | D5 | | D-5 | | | | D5 |
| Clin. Ch. | D-5 | D5 | | D-5 | | | | D5 |
| FACS | D-5 | D5 | | D-5 | D3, D5 | D3, D5 | D3, D5 | D2, D5 |
| Study days 1) | D-5 | D5 | | D17 | D24, D26 | D31, D33 | D38, D40 | D45, D47 |

Figure 1:
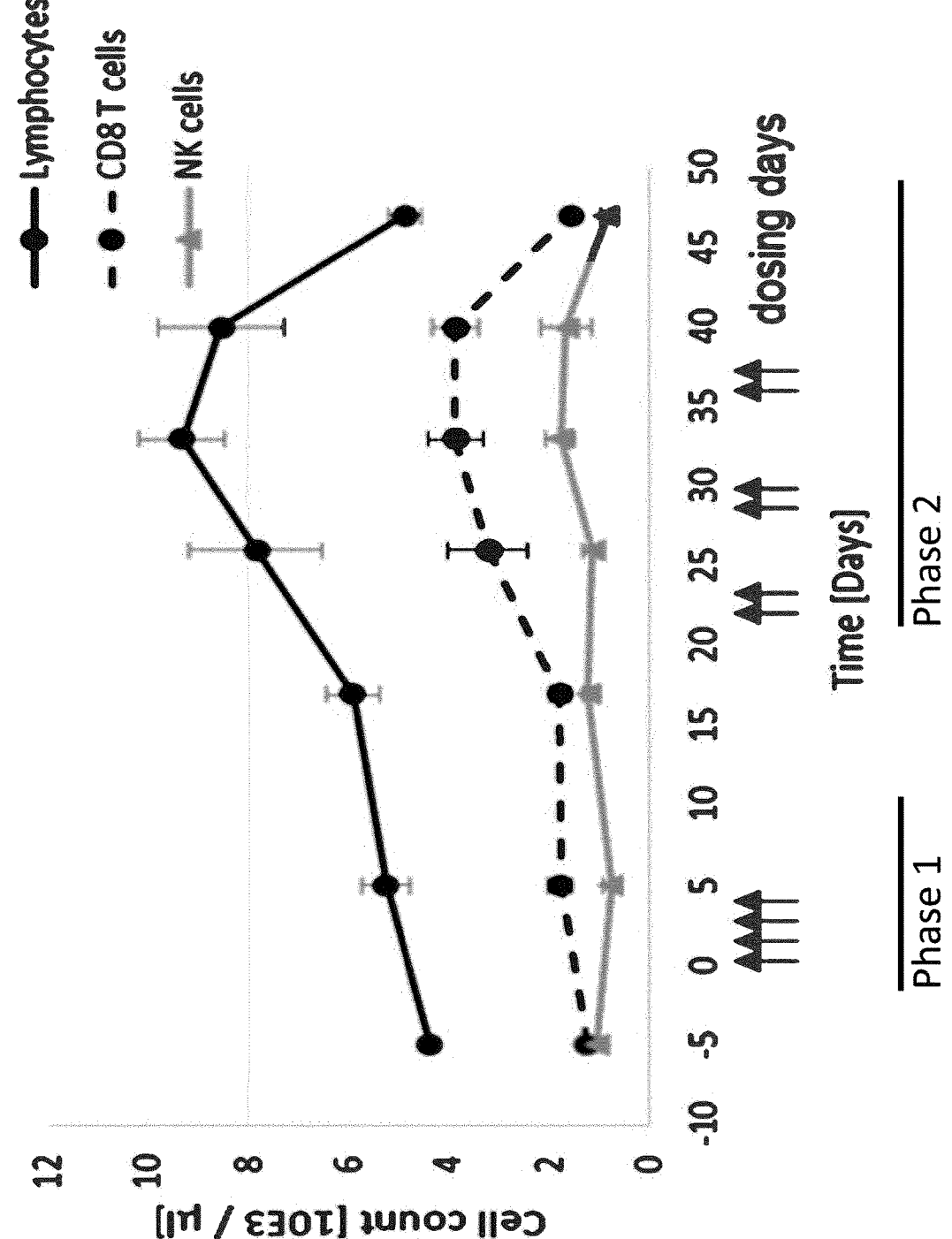
Figure 1:
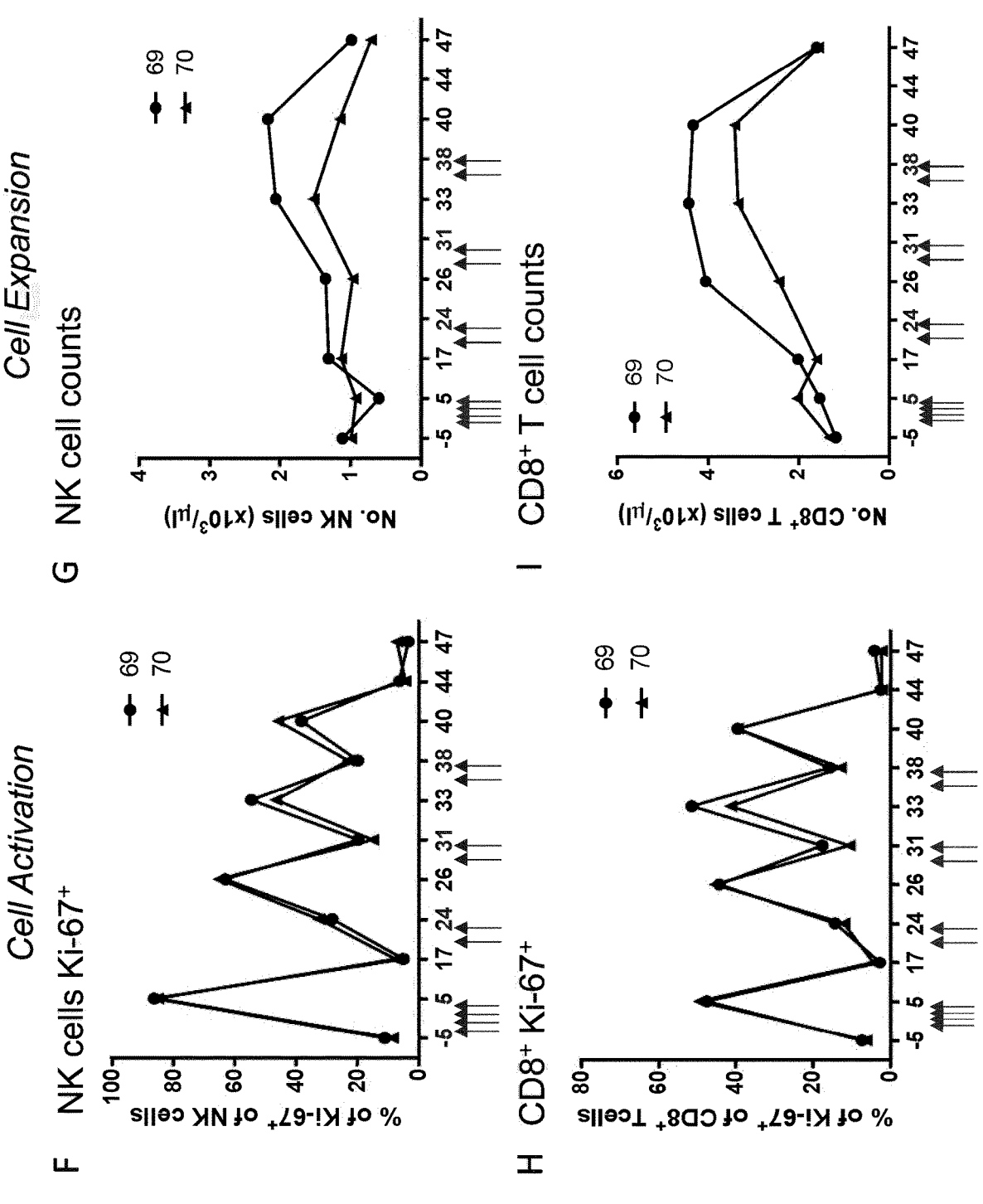
Figure 1:
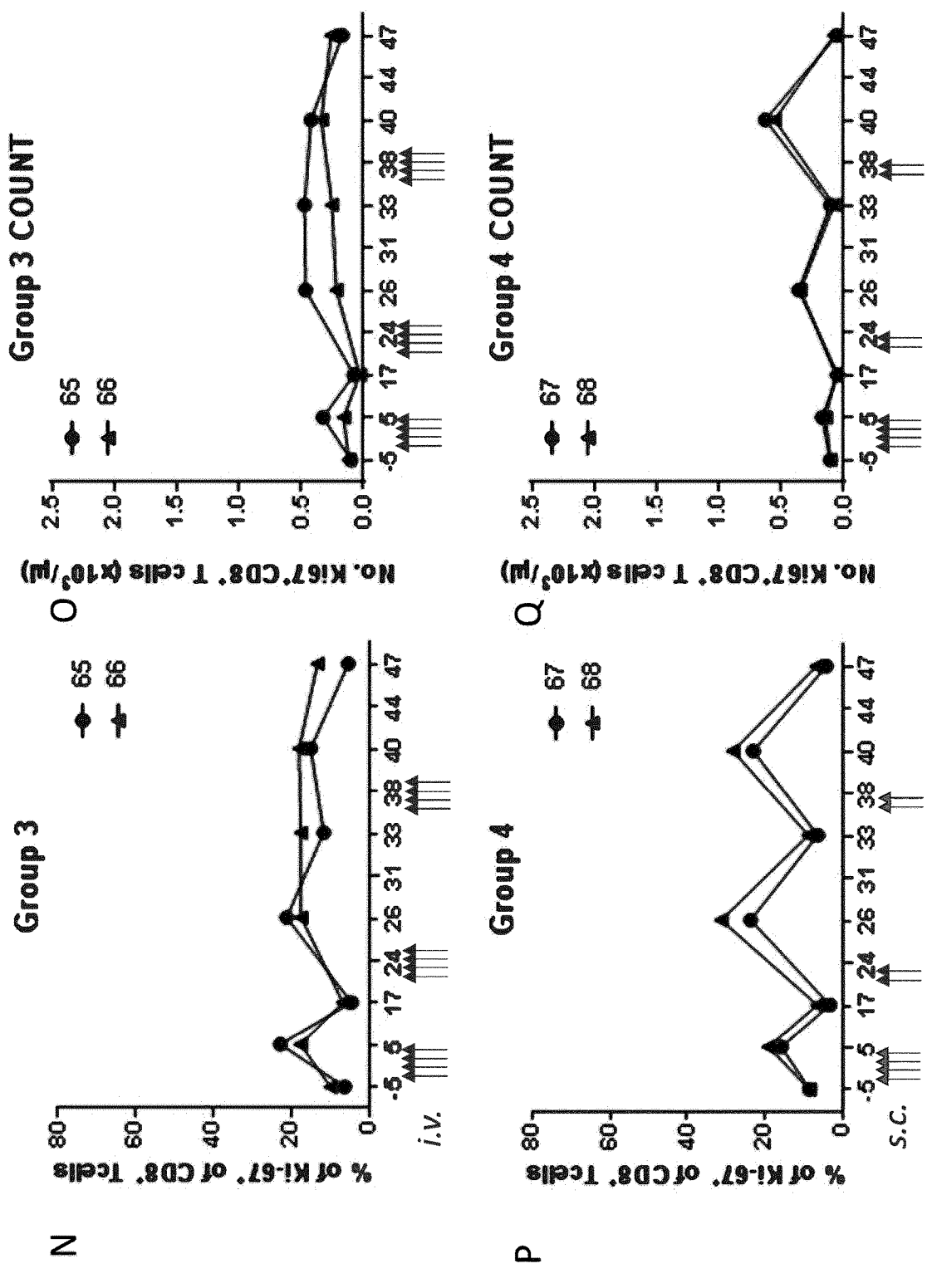

Fig. 1
C
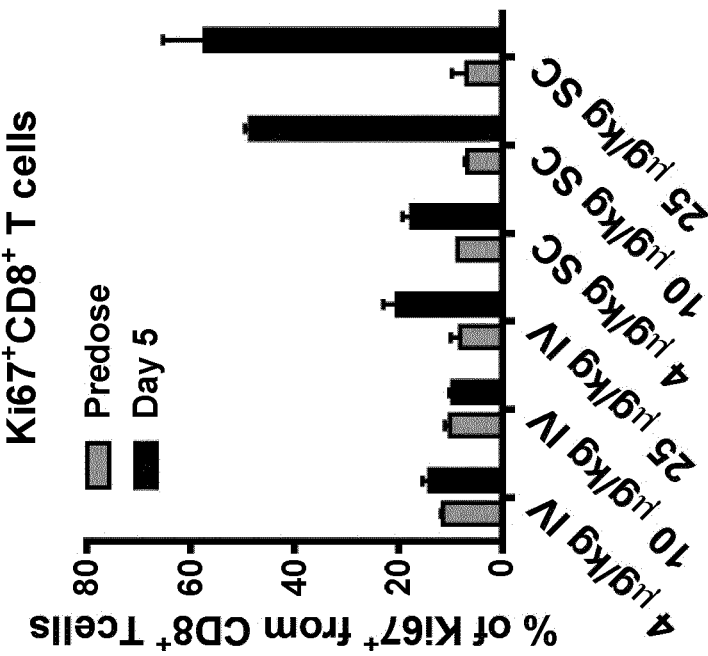
Ki67+CD8+ T cells
B
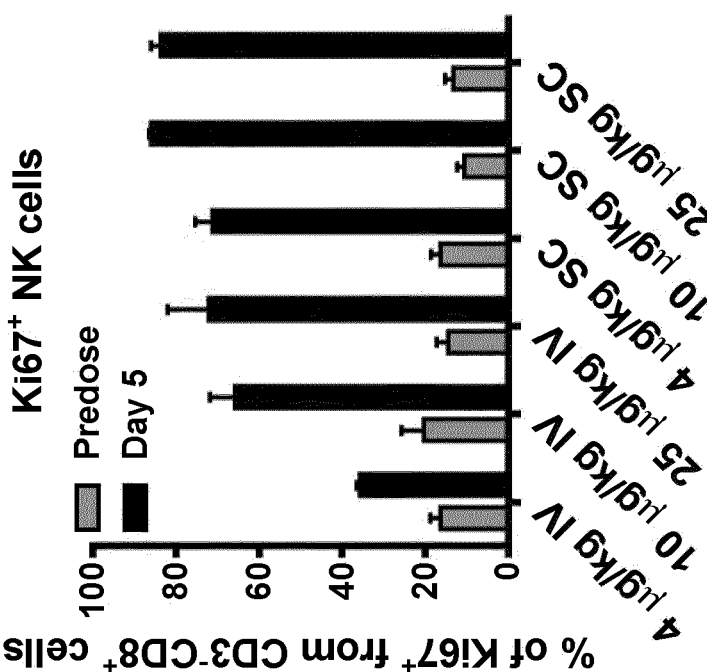
Ki67+ NK cells

Fig. 1
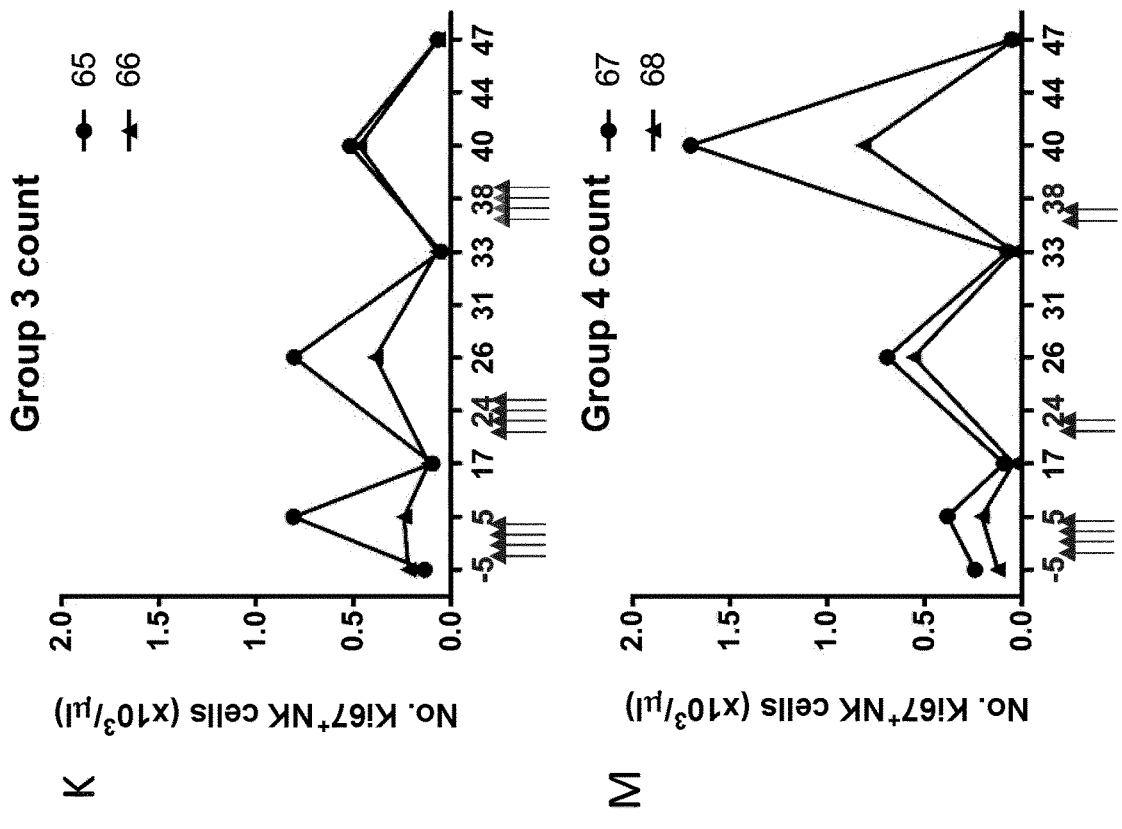
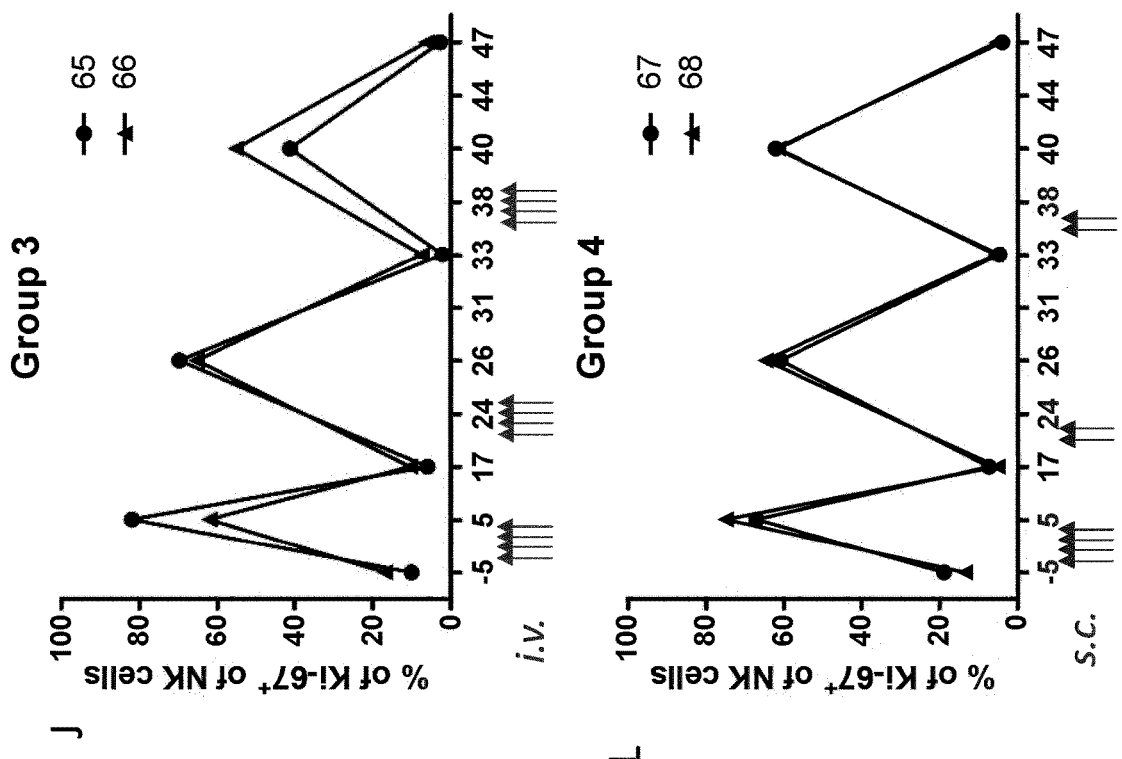

FIG. 10
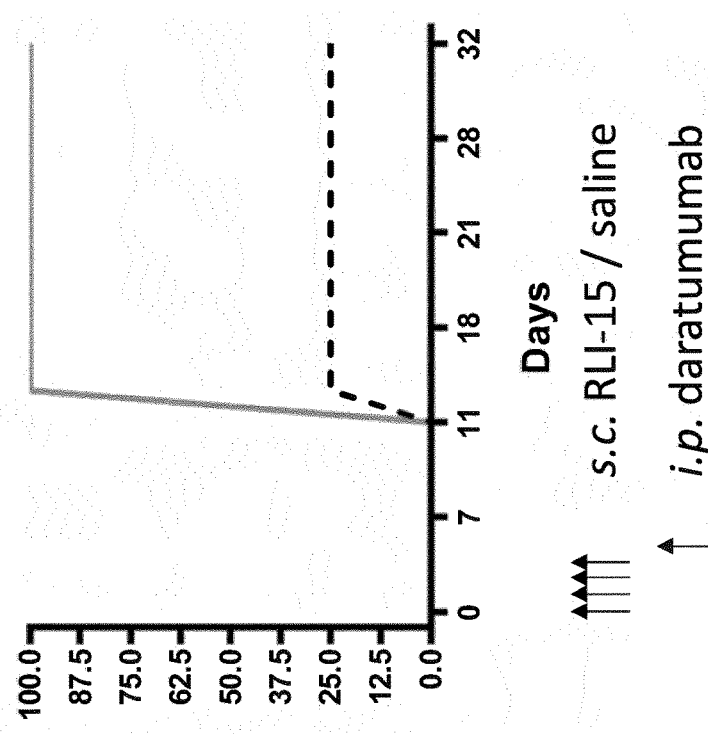
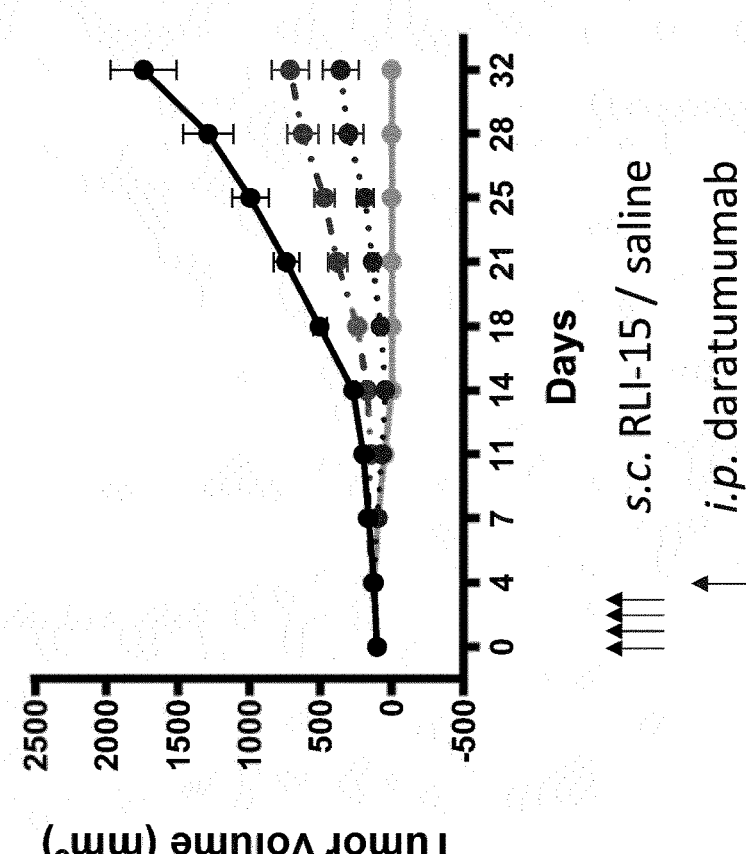

FIG. 11
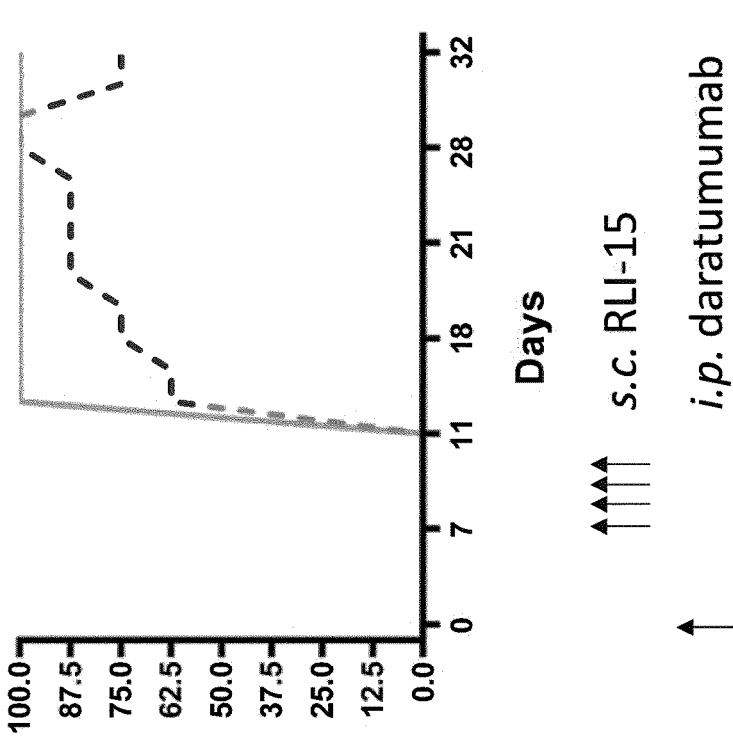
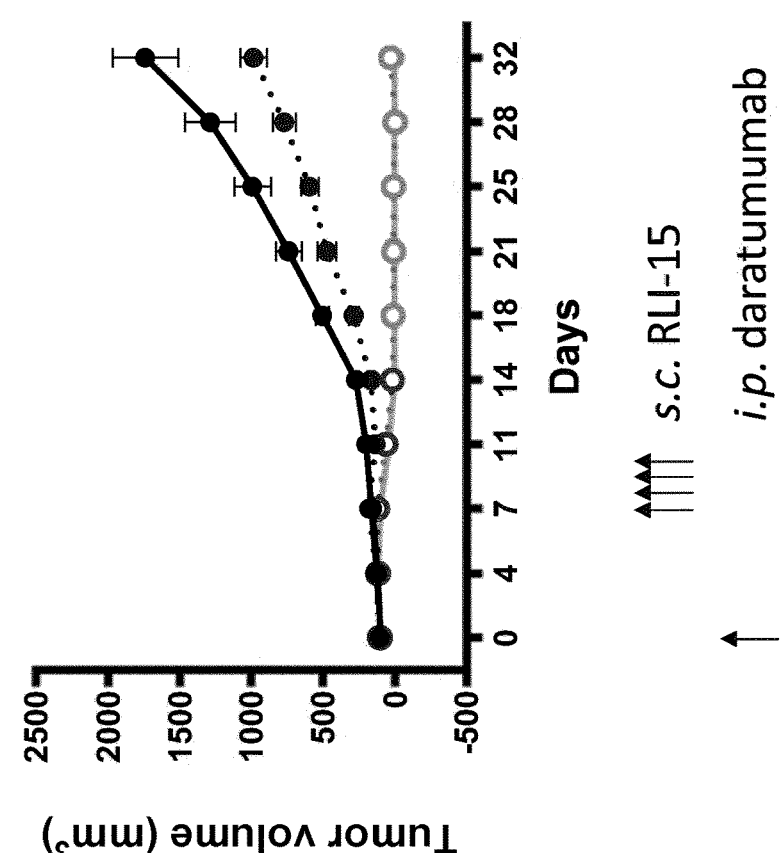

Figure 2:
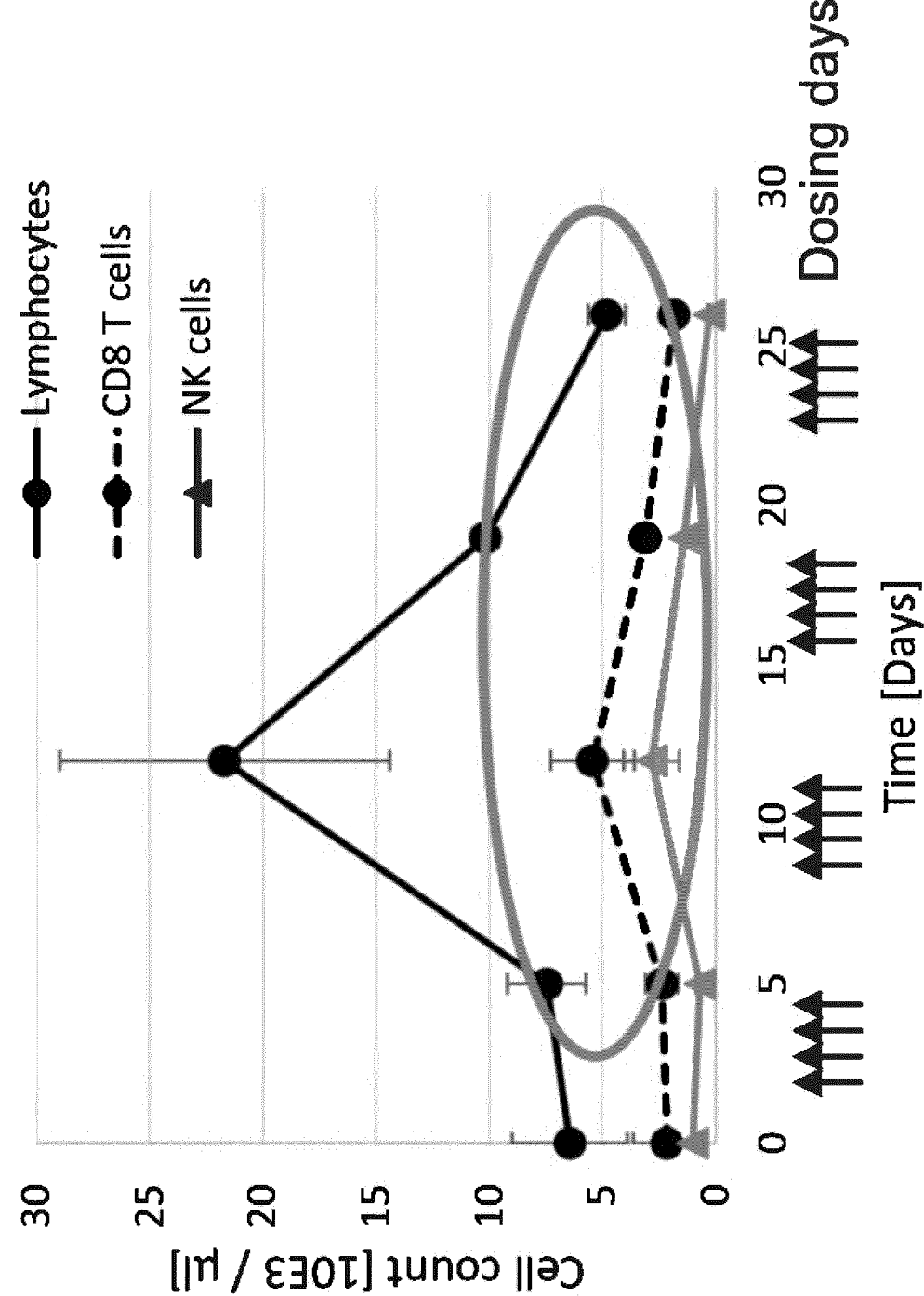
Figure 15:
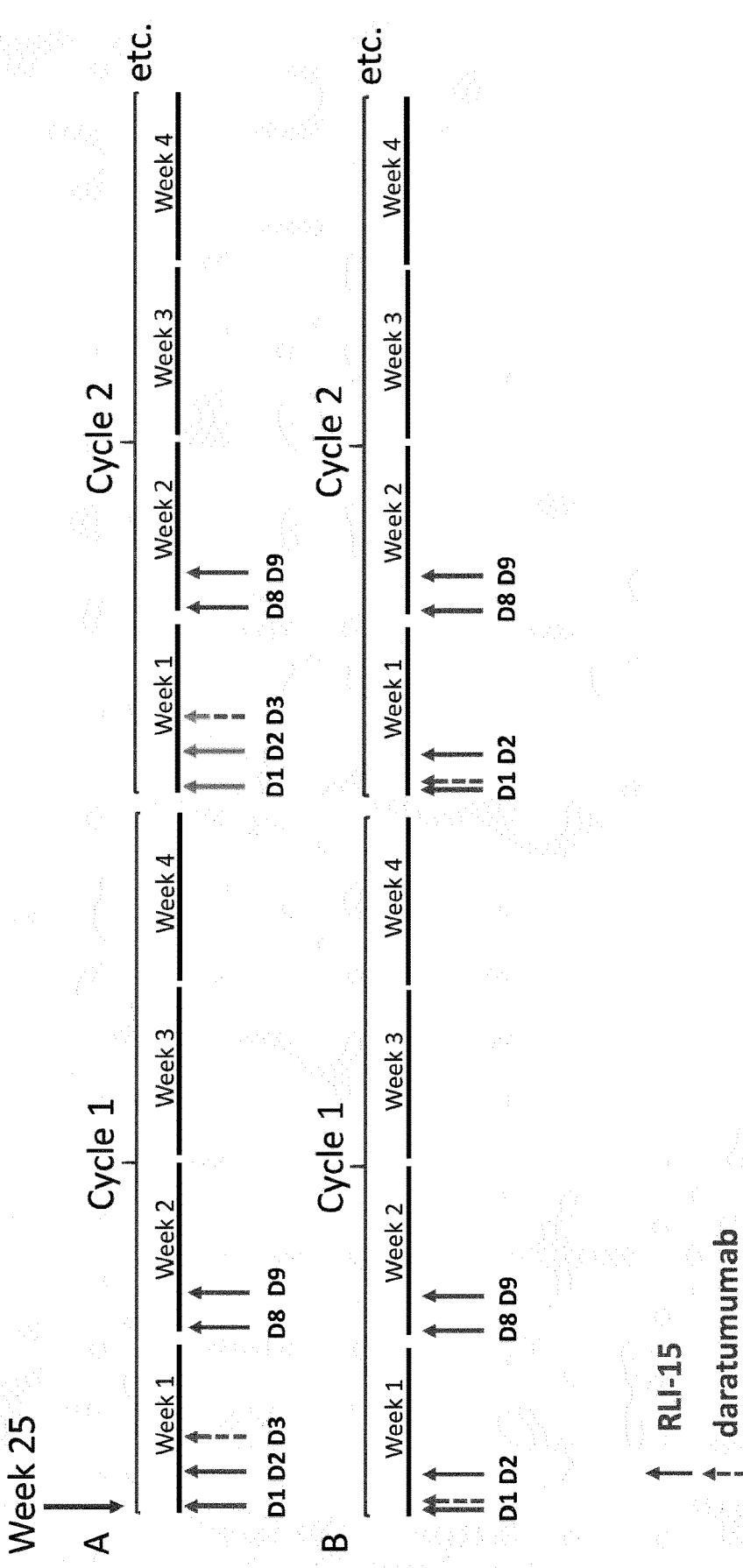

FIG. 15     2) Daratumumab -Week 25 onwards until disease progression: 16 mg/kg IV infusion every 4 weeks; first dose of every-4-week dosing schedule is given at Week 25

Figure 17A:
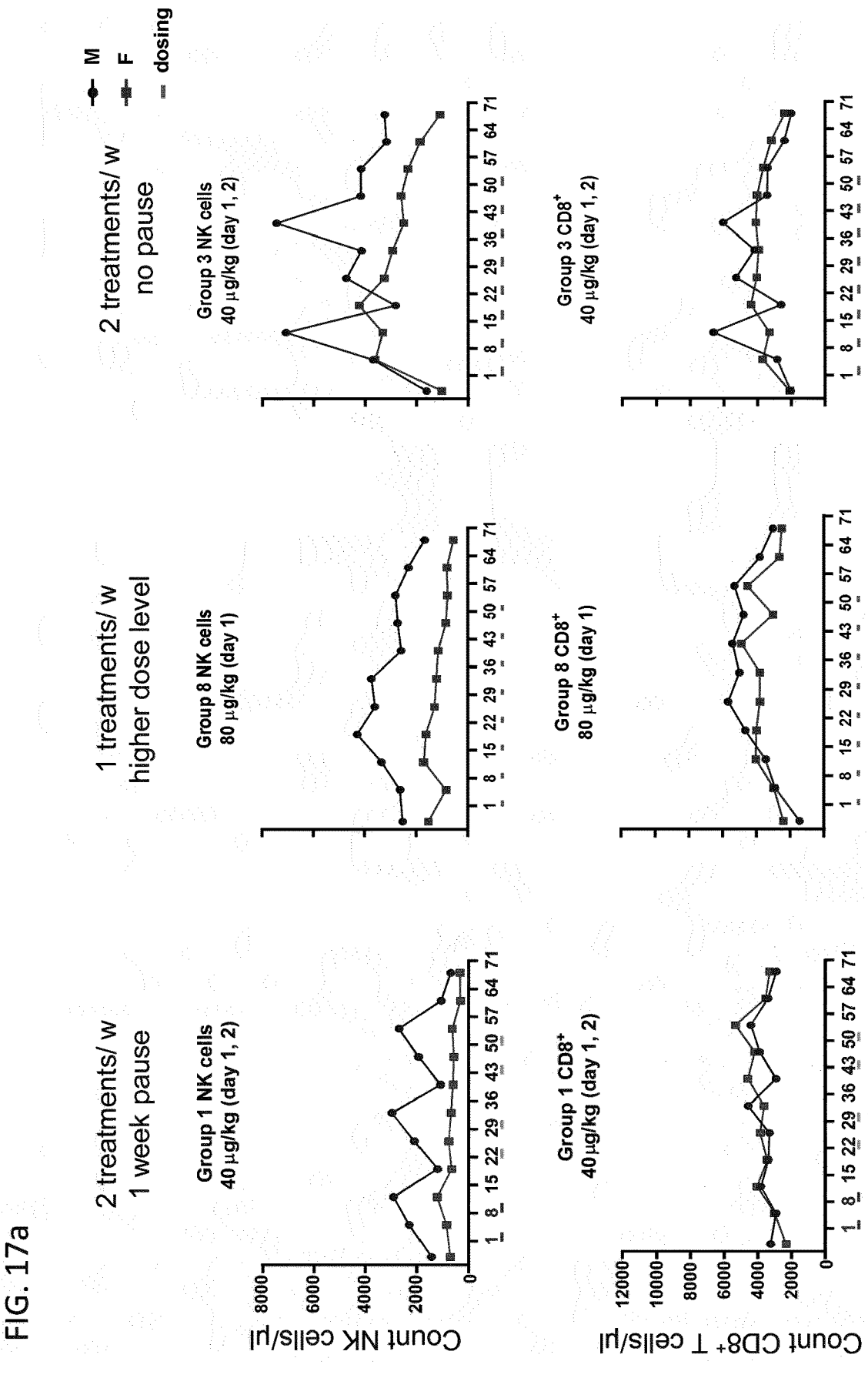

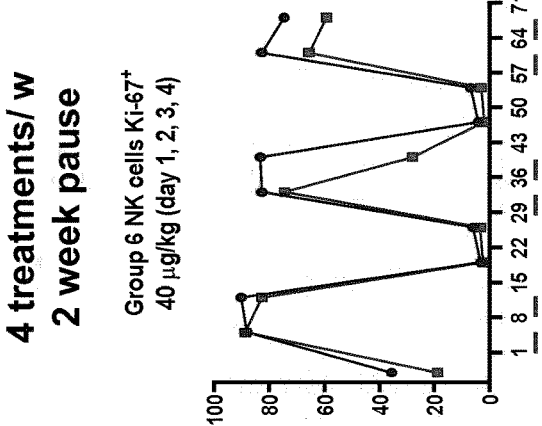
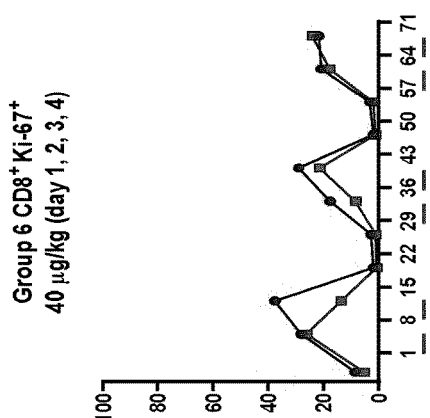
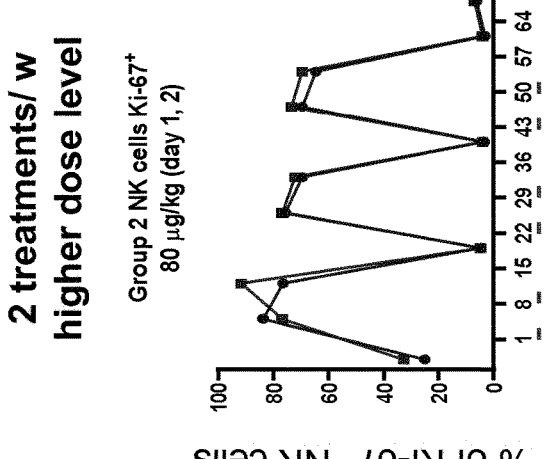
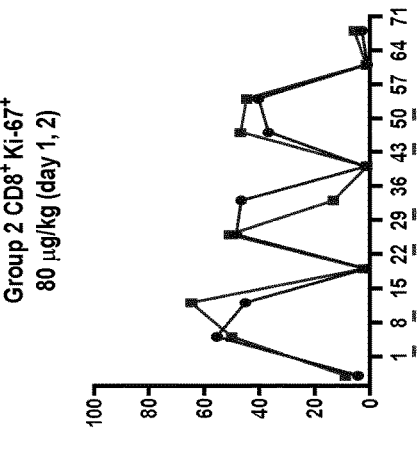
FIG. 17d

FIG. 21

IL-2/IL-15R BETA GAMMA AGONIST DOSING REGIMENS FOR TREATING CANCER OR INFECTIOUS DISEASES

PRIORITY CLAIM

This application claims priority to International Application No. PCT/EP2020/064132, filed May 20, 2020, which claims priority to European Application Nos. 19175436.5, filed May 20, 2019, and 19177064.3, filed May 28, 2019 wherein the contents of said applications are incorporated herein by reference in their entireties. The entire content of the ASCII text file entitled "MAI0013US_Sequence_ Listing.txt" created on Nov. 15, 2021, having a size of 17 kilobytes is incorporated herein by reference.

BACKGROUND OF THE INVENTION

Despite recent advances in the treatment of cancer and infectious diseases, there is still an unmet medical need for more effective and well-tolerated treatments. Immunotherapies, i.e. treatments that make use of the body's own immune system to help fighting the disease, aim at harnessing the power of the immune system to kill malignant tumor cells or infected cells, while leaving healthy tissues intact. Whereas the immune system has an inherent ability to find and eliminate malignancies, tumors and persistent infections have developed mechanisms to escape immune surveillance (Robinson and Schluns 2017). The potential reasons for immune tolerance include failed innate immune activation, the involvement of dense stroma as a physical barrier, and a possible contribution of immune suppressive oncogene pathways (Gajewski et al. 2013). One group of immunotherapies with some clinical success are cytokine treatments, more specifically interleukin 2 (IL-2), commercially available as aldesleukin/PROLEUKIN® (Prometheus Laboratories Inc.) and interleukin 15 (IL-15) therapies known to activate both the innate immune response through NK cells and the adaptive immune response through CD8[+] T cells (Steel et al. 2012, Conlon et al. 2019). While impressive tumor regression was observed with IL-2 therapy, responses are limited to small percentages of patients and carry with it a high level of even life-threatening toxicity. Further, IL-2 displayed not only immune-enhancing but also immune-suppressive activities through the induction of activation-induced cell death of T cells and the expansion of immunosuppressive regulatory T cells ($T_{regs}$). (Robinson and Schluns 2017)

Both IL-2 and IL-15 act through heterotrimeric receptors having α, β and γ subunits, whereas they share the common gamma-chain receptor ($\gamma_c$ or γ)—also shared with IL-4, IL-7, IL-9 and IL-21—and the IL-2/IL-15Rβ (also known as IL-2Rβ, CD122). As a third subunit, the heterotrimeric receptors contain a specific subunit for IL-2 or IL-15, i.e. the IL-2Rα (CD25) or the IL-15Rα (CD215). Downstream, IL-2 and IL-15 heterotrimeric receptors share JAK1 (Janus kinase 1), JAK 3, and STAT3/5 (signal transducer and activator of transcription 3 and 5) molecules for intracellular signaling leading to similar functions, but both cytokines also have distinct roles as reviewed in Waldmann (2015, see e.g. table 1) and Conlon (2019). Accordingly, the activation of different heterotrimeric receptors by binding of IL-2, IL-15 or derivatives thereof potentially leads to a specific modulation of the immune system and potential side effects.

Recently, the novel compounds were designed aiming at specifically targeting the activation of NK cells and CD8[+] T cells.

These are compounds targeting the mid-affinity IL-2/IL-15Rβγ, i.e. the receptor consisting of the IL-2/IL-15Rβ and the $\gamma_c$ subunits, which is expressed on NK cells, CD8[+] T cells, NKT cells and γδ T cells. This is critical for safe and potent immune stimulation mediated by IL-15 trans-presentation, whereas the designed compounds RLI-15, ALT-803 and hetIL-15 already contain (part of) the IL-15Rα subunit and therefore simulate transpresentation of the α subunit by antigen presenting cells. RLI-15 binds to the mid-affinity IL-15Rβγ only, as it comprises the covalently attached sushi+domain of IL-15Rα. In turn, RLI-15 does bind neither to IL-15Rα nor to IL-2Rα. Similarly, ALT-803 and hetIL-15 carry an IL-15Rα sushi domain or the soluble IL-15Rα, respectively, and therefore bind to the mid-affinity IL-15Rβγ receptor. However, due to their non-covalent binding there is a chance that the complex dissociates in vivo and thereby the dissociated fraction of the applied complex further exerts other binding (see below). Probability for dissociation is likely higher for ALT-803 vs. hetIL-15, as ALT-803 only comprises the sushi domain of IL-15Rα, which is known to mediate only partial binding to IL-15, whereas the sushi+ domain is required for full binding (Wei et al. 2001).

Another example of targeting mid-affinity IL-2/IL-15Rβ receptors is NKTR-214, whose hydrolysation to its most active 1-PEG-IL-2 state generates a species whose location of PEG chains at the IL-2/IL-2Rα interface interferes with binding to the high-affinity IL-2Rα, while leaving binding to the mid-affinity IL-2/IL-15Rβ unperturbed (Charych et al. 2016). Further, the mutant IL-2 IL2v with abolished binding to the IL-2Rα subunit is an example of this class of compounds (Klein et al. 2013, Bacac et al. 2016). The targeting of the mid-affinity IL-2/IL-15Rβγ receptors avoids liabilities associated with targeting the high-affinity IL-2 and IL-15 receptors such as T regulatory cells activation induced by IL-2 or vascular leakage syndrome which can be induced by high concentrations of soluble IL-2 or IL-15.

This is due to the fact that the IL-2Rαβγ high affinity receptor is additionally expressed on CD4[+] $T_{regs}$ and vascular endothelium and is activated by IL-2 cis-presentation. Therefore, compounds targeting (also) the high-affinity IL-2Rαβγ potentially lead to $T_{reg}$ expansion and vascular leak syndrome (VLS), as observed for native IL-2 or soluble IL-15 (Conlon et al. 2019). Potentially VLS can be also caused by the de-PEGylated NKTR-214. De-PEGylated NKT2-214 has however a short half-life and it needs to be seen in the clinical development whether at all or to which extent this side-effect plays a role.

The high-affinity IL-15Rαβγ receptors activated by IL-15 cis-presentation are constitutively expressed in T cell leukemia and upregulated on inflammatory NK cells, inflammatory CD8[+] T cells and Fibroblast-like synoviocytes (Kurowska et al. 2002, Perdreau et al. 2010), i.e. these cells also express the IL-15Rα subunit. Such activation should be avoided because of the IL-15 cis-presentation on these cells is involved in the development of T cell leukemia and exacerbation of the immune response, potentially triggering autoimmune diseases. Similarly, the high-affinity IL-15Rαβγ receptor is expressed on vascular endothelium and soluble IL-15 can also induce VLS. IL-15/IL-15Rα complexes do not bind to this high-affinity receptor as they already carry at least the sushi domain of the IL-15Rα, which sterically hinders the binding to the heterotrimeric IL-15Rαβγ receptor. These side effects triggered via engagement of high affinity IL-15Rαβγ receptors are triggered by native IL-15, but also by non-covalent IL-15/IL-15Rα complexes such as ALT-803 and hetIL-15, if disintegration of the complexes occurs in vivo.

Finally, the high-affinity IL-15Rα is constitutively expressed on myeloid cells, macrophages, B cells and neutrophils (Chenoweth et al. 2012) and may be activated by native IL-15 and again by non-covalent IL-15/IL-15Rα complexes such as ALT-803 and hetIL-15, if disintegration of the complexes occurs in vivo.

In summary, IL-15 has similar immune enhancing properties as IL-2, but it is believed to not share the immune-suppressive activities like activation of $T_{reg}$ cells and does not cause VLS in the clinic (Robinson and Schluns 2017), whereas drawbacks of IL-15 treatment include its short in vivo half-life and its reliance on trans-presentation by other cell types (Robinson and Schluns 2017). This leads to the development of engineered IL-2/IL-15Rβγ agonists, some of them recently entered clinical development.

Although high-dose IL-2 treatment is approved in renal cell carcinoma and metastatic melanoma (at 600,000 IU/kg administered by i.v. bolus over 15 min every 8 hours for a maximum of 14 doses, following 9 days of rest before the regimen is repeated if tolerated by the patient), IL-2 still continues to be investigated in order to define a lower-dose schedule that provides sufficient immune activation with a better tolerated safety profile, e.g. by infusion over 90 days at low-dose expand NK cells with intermediate pulses of IL-2 to provide activation of an expanded NK cell pool and many other low-dose i.v. or s.c. treatments usually given in combination with other immunotherapeutics have been assessed but with inconclusive results (Conlon et al. 2019). Low-dose s.c. regimens (1-30 million IU/m²/d) have been investigated because they may reduce toxicity but compromise efficacy (Fyfe et al. 1995) but preferentially activate $T_{regs}$. Therefore, low dose IL-2 is used in immunosuppressive treatments (Rosenzwajg et al. 2019).

Accordingly, administration, dosing and dosing schedules of the engineered IL-2/IL-15Rβγ agonists will be key for their clinical success, which is driven by multiple factors, for example related to efficacy, side effects, patient compliance and convenience e.g. in combinations with other drugs.

Recently, pharmacokinetics and pharmacodynamics of hetIL-15 in rhesus macaques were published (Bergamaschi et al. 2018). hetIL-15 was dosed s.c. at fixed doses of 0.5, 5 or 50 µg/kg in dosing cycles with administration on days 1, 3, 5, 8, 10 and 12 (cycle 1) and on days 29, 31, 33, 36, 38 and 40 (dosing cycle 2). Further, monkeys were dosed with a doubling step-dose regimen with injections on days 1, 3, 5, 8, 10 and 12 at doses of 2, 4, 8, 16, 32 and 64 µg/kg. Iv. administration leads to a peak of IL-15 plasma levels at 10 min after injection with a half-life of about 1.5 h, whereas s.c. administration of hetIL-15 resulted in a $T_{1/2}$, of about 12 h. It was shown that both AUC and $C_{max}$ were reduced between day 1 and 40 upon treatment with a fixed dose s.c., 2-fold and 4-fold at fixed dose of 5 µg/kg, and even 9-fold and 8-fold at a fixed dose of 50 µg/kg. The authors conclude that "the consumption of the administered hetIL-15 progressively increased during the treatment cycle, reflecting an increase in the pool of cells responding to IL-15" and that "the fixed-dose regimen provided an excess of IL-15 early in the 2-week cycle but not enough cytokine later in the treatment cycle". The authors therefore continued with an administration scheme consisting of 6 progressively doubling doses from 2 to 64 µg/kg of hetIL-15 over the course of two weeks, leading to a progressive increase in systemic exposure and comparable trough levels, overall interpreted to better match the increasing IL-15 need by the expanding pool of target cells during treatment. With respect to the proliferation of CD8+ T cells, the authors observed with the fixed-dose regimens a decline at day 15 for proliferating Ki67+CD8+ T cells, whereas macaques treated with the step-dose regiment showed high and comparable CD8+ T cell proliferation on day 8 and 15.

Most of the designed IL-2/IL-15Rβγ agonists aim for increasing their in vivo half-life either by fusing the IL-15, IL-2 or variant thereof to another protein, e.g. to the soluble IL-15Rα (hetIL-15, where the complexation with the receptor goes along with a considerable extension of the half-life), to add an Fc part of an antibody to the complex (ALT-803) or IL-15/IL-15Rα Fc fusions (P22339) disclosed in U.S. Pat. No. 10,206,980 and IL15/IL15Rα heterodimeric Fc-fusions with extended half-lives (Bernett et al. 2017) (WO 2014/145806), to a non-binding IgG (IgG-IL2v) or to an albumin binding domain (see WO 2018/151868A2). Other examples of IL-2/IL-15Rβγ agonists are CT101-IL2 (Ghasemi et al. 2016, Lazear et al. 2017), PEGylated IL-2 molecules like and NKTR-214 (Charych et al. 2016) and THOR-924 (Caffaro et al. 2019) (WO 2019/028419, WO 2019/028425), the polymer-coated IL-15 NKTR-255 (Miyazaki et al. 2018), NL-201/NEO-201 (Silva et al. 2019), RGD-targeted IL-15/IL-15Rα Fc complex (US 2019/0092830), RTX-240 by Rubius Therapeutics (red blood cells expressing an IL-15/IL-15Rα fusion protein, WO 2019/173798), and THOR-707 (Joseph et al. 2019). Further, targeted IL-2/IL-15Rβγ agonists, where the agonist is fused to a binding molecule targeting specific cells, e.g. tumor, tumor-microenvironment or immune cells, have an increased in vivo half-life (RG7813, RG7461, immunocytokines of WO 2012/175222A1, modulokines of WO 2015/018528A1 and KD033 by Kadmon, WO 2015/109124).

Studies indicated that ALT-803 has a 7.5-hour serum half-life in mice (Liu et al. 2018) and 7.2 to 8 h in cynomolgus monkeys (Rhode et al. 2016) compared with <40 minutes observed for IL-15 (Han et al. 2011). In the clinic, ALT-803 was administered i. v. or s.c. in a Phase I dose escalation trial weekly for 4 consecutive weeks, followed by a 2-week rest period for continued monitoring, for two 6-week cycles of therapy starting at 0.3 µg/kg up to 20 µg/kg. Results from the trial led to the selection of 20 µg/kg/dose s.c. weekly as the optimal dose and route of delivery for ALT-803 (Margolin et al. 2018).

NKTR-214 is described as a highly "combinable cytokine" dosed more like an antibody than a cytokine due to its long half-life in vivo. Its anticipated dosing schedule in humans is once every 21 days. Yet NKTR-214 provides a mechanism of direct immune stimulation characteristic of cytokines. PEGylation dramatically alters the pharmacokinetics of NKTR-214 compared with IL-2, providing a 500-fold increase in AUC in the tumor compared with an IL-2 equivalent dose. Pharmacokinetics of NKTR-214 were determined after i.v. administration in mice and resulted for the most active species of NKTR-214 (i.e. 2-PEG-IL2, 1-PEG-IL2, free IL2) in a gradually increase, reaching $C_{max}$ at 16 hours post dose and a decrease with $t_{1/2}$ of 17.6 hours (Charych et al. 2017). Based on the increased half-life due to PEGylation, NKTR-214 was tested in five dose regimens in combination with nivolumab in NCT02983045 (see www.clinicaltrials.gov)

0.006 mg/kg NKTR-214 every 3 weeks (q3w) with 240
        mg nivolumab every two weeks (q2w),
    0.003 mg/kg NKTR-214 q2w with 240 mg nivolumab
        q2w,
    0.006 mg/kg NKTR-214 q2w with 240 mg nivolumab
        q2w, 0.006 mg/kg NKTR-214 q3w with 360 mg nivolumab q3w, 0.009 mg/kg NKTR-214 q3w with 360 mg nivolumab q3w.

After completion of the first part of the study it was continued with a dose of 0.006 mg/kg NKTR-214 q3w with 360 mg nivolumab q3w.

Recently, IL-2/IL-15 mimetics have been designed by a computational approach, which is reported to bind to the qw for first 4 doses and q2w for remaining doses up to maximum 36 months with a starting dose of 10 mg and 15 mg for the second and following doses, q3w up to max. 36 months with a dose of 10 mg, qw for 4 weeks followed by q2w with a starting dose of 15 mg and 20 mg from the second administration onward, or q3w with a dose of 15 mg (see NCT03386721, www.clinicaltrials.gov).

TABLE 1

| In vivo half-life of IL-15 and IL-2/IL-15Rβγ agonists | | | | |
|---|---|---|---|---|
| | T ½ mouse s.c. | T ½ human | optimized human admin. | |
| IL-15 (rhIL-15) | <40 min | $T_{max}$ 4 h after s.c. bolus i.v. $T^{1/2}$ = 2.7 h | s.c. days 1-8 and 22-29, or i.v. continuous infusion for 5 or 10 consecutive days, or i.v. daily for 12 consecutive days | NCT03388632 NCT01572493 NCT01021059 (Han et al. 2011) (Miller et al. 2018) (Conlon et al. 2015) |
| ALT-803 | 7.5 h for i.v. versus 7.7 h for s.c. | s.c > 96 h, but not i.v. $C_{max}$ after 6 h, still detectable at 24 h | 20 µg/kg s.c. qw | (Romee et al. 2018) (Wrangle et al. 2018) |
| hetIL-15, NIZ985 | ~12 h | | 6 progressively doubling doses from 2 to 64 µg/kg over the course of 2 weeks 1 µg/kg (3× weekly; 2-weeks-on/2-weeks-off) | (Bergamaschi et al. 2018) (Conlon et al. 2019) |
| RLI-15 | 3.5 h (own data) | ND | not tested yet | |
| NKT-214 | multiple days | $T^{1/2}$ 20 h, $C_{max}$ 1-2 days post dose | 6 µg/kg i.v. q3w | (Charych et al. 2017) (Bentebibel et al. 2017) |
| NKTR-214 most active species | 17.6 h | | | (Charych et al. 2017) |
| RO687428 | | | ≥5 mg i.v. qw or q3w | NCT03386721 |

IL-2Rβγ heterodimer but have no binding site for IL-2Rα (Silva et al. 2019) and therefore also qualify as IL-2/IL-15Rβγ agonists. Due to their small size of about 15 kDa (see supplementary information FIG. S13) they are expected to have a rather short in vivo half-life.

Another example of such IL-2 based IL-2/IL-15Rβγ agonist is an IL-2 variant (IL2v) by Roche, which is used in fusion proteins with antibodies. RO687428, an example comprising IL2v, is administered in the clinic i.v.

on days 1, 15, 29, and once in 2 weeks from day 29 onwards with a starting dose of 5 mg and increased subsequently, or in a q3w schedule (see NCT03063762, www.clinicaltrials.gov), once weekly (qw) with a starting does of 5 mg as monotherapy, with a starting dose of 5 mg qw in combination with cetuximab and with a starting dose of 10 mg qw in combination with trastuzumab (see NCT02627274, www.clinicaltrials-.gov), or in combination with atezolizumab, qw for first 4 doses, and once in 2 weeks (q2w) for remaining doses up to maximum 36 months starting with a first dose of 10 mg and 15 mg for the second and following doses, However, already less than 15 min exposure of cells with IL-15 (at 10 ng/ml) expressing the receptor to native IL-15 leads to the maximal level of Stat5 activation and subsequent pharmacodynamic effects (Castro et al. 2011).

In summary, presently IL-2/IL-15Rβγ agonists are dosed in order to achieve a continuous availability of the molecule in the patient, either by continuous infusion of short-lived molecules or by extending drastically the half-life of IL-2/IL-15Rβγ agonists through PEGylation or fusion to Fc fragments or antibodies. This is in line with the common understanding that both the tumor homing and the in vivo anti-tumor activity of NK cells are dependent on the continuous availability of IL-2 or IL-15, whereas if NK cells are not frequently stimulated by IL-15, they rapidly die (Larsen et al. 2014). Further, such therapies focus very much at maximizing the CD8[+] T-cell expansion, whereas at the same time try to minimize the $T_{reg}$ expansion (Charych et al. 2013).

On the other hand, Frutoso et al. demonstrated in mice that two cycles of injection of IL-15 or IL-15 agonists resulted in a weak or even no expansion of NK cells in vivo in immunocompetent mice, whereas CD44[+] CD8[+] T cells were still responsive after a second cycle of stimulation with IL-15 or its agonists (Frutoso et al. 2018). Escalating the dose for the second cycle did not make a marked difference. Furthermore, NK cells extracted from mice after two cycles of stimulation had a lower IFN-γ secretion compared to after one cycle, which was equivalent to that of untreated mice (Frutoso et al. 2018). This phenomenon may be explained by the findings that prolonged stimulation of NK cells with a strong activation signal leads to a preferential accrual of mature NK cells with altered activation and diminished functional capacity (Elpek et al. 2010). Similarly, continuous treatment with IL-15 was described to exhaust human NK cells and this effect was brought into context with the influence of fatty acid oxidation on the activity of NK cells suggesting that induces of fatty acid oxidation have the potential to greatly enhance IL-15 mediated NK cell immunotherapies (Felices et al. 2018).

Therefore, despite recent advances in understanding the function of the IL-2/IL-15Rβγ agonists, it is still unclear how such IL-2/IL-15Rβγ agonists are optimally dosed and integrated into treatment regimens as a single agent or in combination with other treatments.

SUMMARY OF THE INVENTION

The inventors have surprisingly identified that a pulsed cyclic dosing as well as a pulsed dosing of an interleukin-2/interleukin-15 receptor βγ (IL-2/IL-15Rβγ) agonist in primates lead to an optimal activation of NK and CD8$^+$ T cells, i.e. that the administration of the IL-2/IL-15Rβγ agonist results in a marked increase of Ki-67$^+$ NK cells and CD8$^+$ T cells and/or an increase in NK cell and CD8$^+$ T cell numbers, which is repeated/maintained during multiple rounds of administration.

Accordingly, the present invention provides novel pulsed cyclic administration regimes and pulsed administration regimes for use in treating or managing cancer or infectious diseases in humans with IL-2/IL-15Rβγ agonists.

DEFINITIONS, ABBREVIATIONS AND ACRONYMS

"IL-2/IL-15Rβγ agonist" refers to complex of an IL-2 or IL-2 derivative or an IL-15 or IL-15 derivative targeting the mid-affinity IL-2/IL-15Rβγ and having a decreased or abandoned binding of the IL-2Rα or IL-15Rα. Decreased binding in this context means at least 50%, preferably at least 80% and especially at least 90% decreased binding to the respective Receptor a compared to the wild-type IL-15 or IL-2, respectively. As described and exemplified below, decreased or abandoned binding of IL-15 to the respective IL-15Rα, may be mediated by forming a complex (covalent or non-covalent) with an IL-15Rα, derivative, by mutations in the IL-15 leading to a decreased or abandoned binding, or by site-specific PEGylation or other post-translational modification of the IL-15 leading to a decreased or abandoned binding. Similarly, decreased or abandoned binding of IL-2 to the respective IL-2Rα may be mediated by mutations in the IL-2 leading to a decreased or abandoned binding, or by site-specific PEGylation or other post-translational modification of the IL-2 leading to a decreased or abandoned binding.

"Interleukin-2", "IL-2" or "IL2" refers to the human cytokine as described by NCBI Reference Sequence AAB46883.1 or UniProt ID P60568 (SEQ ID NO: 1). Its precursor protein has 153 amino acids, having a 20-aa peptide leader and resulting in a 133-aa mature protein. Its mRNA is described by NCBI GenBank Reference S82692.1.

"IL-2 derivative" refers to a protein having a percentage of identity of at least 92%, preferably of at least 96%, more preferably of at least 98%, and most preferably of at least 99% with the amino acid sequence of the mature human IL-2 (SEQ ID NO: 2). Preferably, an IL-2 derivative has at least about 0.1% of the activity of human IL-2, preferably at least 1%, more preferably at least 10%, more preferably at least 25%, even more preferably at least 50%, and most preferably at least 80%, as determined by a lymphocyte proliferation bioassay. As interleukins are extremely potent molecules, even such low activities as 0.1% of human IL-2 may still be sufficiently potent, especially if dosed higher or if an extended half-life compensates for the loss of activity. Its activity is expresses in International Units as established by the World Health Organization 1$^{st}$ International Standard for Interleukin-2 (human), replaced by the 2$^{nd}$ International Standard (Gearing and Thorpe 1988, Wadhwa et al. 2013). The relationship between potency and protein mass is as follows: 18 million IU PROLEUKIN=1.1 mg protein. As described above, mutations (substitutions) may be introduced in order to specifically link PEG to IL-2 for extending the half-life as done for THOR-707 (Joseph et al. 2019) (WO2019/028419A1) or for modifying the binding properties of the molecule, e.g. reduce the binding to the IL-2α receptor as done for IL2v (Klein et al. 2013, Bacac et al. 2016) (WO 2012/107417A1) by mutation of L72, F42 and/or Y45, especially F42A, F42G, F42S, F42T, F42Q, F42E, F42N, F42D, F42R, F42K, Y45A, Y45G, Y45S, Y45T, Y45Q, Y45E, Y45N, Y45D, Y45R, Y45K, L72G, L72A, L72S, L72T, L72Q, L72E, L72N, L72D, L72R, and L72K, preferably mutations F42A, Y45A and L72G. Various other mutations of IL-2 have been described: R38W for reducing toxicity (Hu et al. 2003) due to reduction of the vasopermeability activity (US 2003/0124678); N88R for enhancing selectivity for T cells over NK cells (Shanafelt et al. 2000); R38A and F42K for reducing the secretion of proinflammatory cytokines from NK cells ((Heaton et al. 1993) (U.S. Pat. No. 5,229,109); D20T, N88R and Q126D for reducing VLS (US 2007/0036752); R38W and F42K for reducing interaction with CD25 and activation of T$_{reg}$ cells for enhancing efficacy (WO 2008/003473); and additional mutations may be introduced such as T3A for avoiding aggregation and C125A for abolishing O-glycosylation (Klein et al. 2017). Other mutations or combinations of the above may be generated by genetic engineering methods and are well known in the art. Amino acid numbers refer to the mature IL-2 sequence of 133 amino acids.

"Interleukin-15", "IL-15" or "IL15" refers to the human cytokine as described by NCBI Reference Sequence NP_000576.1 or UniProt ID P40933 (SEQ ID NO: 3). Its precursor protein has 162 amino acids, having a long 48-aa peptide leader and resulting in a 114-aa mature protein (SEQ ID NO: 4). Its mRNA, complete coding sequence is described by NCBI GenBank Reference U14407.1. The IL-15Rα sushi domain (or IL-15Rα$_{sushi}$, SEQ ID NO: 6) is the domain of IL-15Rαwhich is essential for binding to IL-15.

"IL-15 derivative" or "derivative of IL-15" refers to a protein having a percentage of identity of at least 92%, preferably of at least 96%, more preferably of at least 98%, and most preferably of at least 99% with the amino acid sequence of the mature human IL-15 (114 aa) (SEQ ID NO: 4). Preferably, an IL-15 derivative has at least 10% of the activity of IL-15, more preferably at least 25%, even more preferably at least 50%, and most preferably at least 80%. More preferably, the IL-15 derivative has at least 0.1% of the activity of human IL-15, preferably 1%, more preferably at least 10%, more preferably at least 25%, even more preferably at least 50%, and most preferably at least 80%. As for IL-2 described above, interleukins are extremely potent molecules, even such low activities as 0.1% of human IL-15 may still be sufficiently potent, especially if dosed higher or if an extended half-life compensates for the loss of activity. Also for IL-15, a plethora of mutations has been described in order to achieve various defined changes to the molecule: D8N, D8A, D61A, N65D, N65A, Q108R for reducing binding to the IL-15Rβγβγ$_c$ receptors (WO 2008/143794A1); N72D as an activating mutation (in ALT-803); N1D, N4D, D8N, D3ON, D61N, E64Q, N65D, and Q108E to reduce the proliferative activity (US 2018/0118805); L44D, E46K, L47D, V49D, 150D, L66D, L66E, I67D, and I67E for reducing binding to the IL-15Rα (WO 2016/142314A1); N65K and L69R for abrogating the binding of IL-15Rb (WO 2014/207173A1); Q101D and Q108D for inhibiting the function of IL-15 (WO 2006/020849A2); S7Y, S7A, K10A, K11A for reducing IL-15Rβ binding (Ring et al. 2012); L45, S51, L52 substituted by D, E, K or R and E64, I68, L69 and N65 replaced by D, E, R or K for increasing the binding to the IL-15Rα (WO 2005/085282A1); N71 is replaced by S, A or N, N72 by S, A or N, N77 by Q, S, K, A or E and N78 by S, A or G for reducing deamidation (WO 2009/135031A1); WO 2016/060996A2 defines specific regions of IL-15 as being suitable for substitutions (see para. 0020, 0035, 00120 and 00130) and specifically provides guidance how to identify potential substitutions for providing an anchor for a PEG or other modifications (see para. 0021); Q108D with increased affinity for CD122 and impaired recruitment of CD132 for inhibiting IL-2 and IL-15 effector functions and N65K for abrogating CD122 affinity (WO 2017/046200A1); N1D, N4D, D8N, D3ON, D61N, E64Q, N65D, and Q108E for gradually reducing the activity of the respective IL-15/IL-15Rα complex regarding activating of NK cells and CD8 T cells (see FIG. 51, WO 2018/071918A1, WO 2018/071919A1). Additionally or alternatively, the artisan can easily make conservative amino acid substitutions.

The activity of both IL-2 and IL-15 can be determined by induction of proliferation of kit225 cells as described by Hori et al. (1987). Preferably, methods such as colorimetry or fluorescence are used to determine proliferation activation due to IL-2 or IL-15 stimulation, as for example described by Soman et al. using CTLL-2 cells (Soman et al. 2009). As an alternative to cell lines such as the kit225 cells, human peripheral blood mononuclear cells (PBMCs) or buffy coats can be used. A preferred bioassay to determine the activity of IL-2 or IL-15 is the IL-2/IL-15 Bioassay Kit using STAT5-RE CTLL-2 cells (Promega Catalog number CS2018B03/B07/B05).

IL-15 muteins can be generated by standard genetic engineering methods and are well known in the art, e.g. from WO 2005/085282, US 2006/0057680, WO 2008/143794, WO 2009/135031, WO 2014/207173, WO 2016/142314, WO 2016/060996, WO 2017/046200, WO 2018/071918, WO 2018/071919, US 2018/0118805. IL-15 derivatives may further be generated by chemical modification as known in the art, e.g. by PEGylation or other posttranslational modifications (see WO 2017/112528A2, WO 2009/135031).

"IL-2Rα" refers to the human IL-2 receptor α or CD25.

"IL-15Rα" refers to the human IL-15 receptor a or CD215 as described by NCBI Reference Sequence AAI21142.1 or UniProt ID Q13261 (SEQ ID NO: 5). Its precursor protein has 267 amino acids, having a 30-aa peptide leader and resulting in a 231-aa mature protein. Its mRNA is described by NCBI GenBank Reference HQ401283.1. The IL-15Rα sushi domain (or IL-15Rα$_{sushi}$, SEQ ID NO: 6) is the domain of IL-15Rα which is essential for binding to IL-15

(Wei et al. 2001). The sushi+ fragment (SEQ ID NO: 7) comprising the sushi domain and part of hinge region, defined as the fourteen amino acids which are located after the sushi domain of this IL-15Rα, in a C-terminal position relative to said sushi domain, i.e., said IL-15Rα hinge region begins at the first amino acid after said (C4) cysteine residue, and ends at the fourteenth amino acid (counting in the standard "from N-terminal to C-terminal" orientation). The sushi+ fragment reconstitutes full binding activity to IL-15 (WO 2007/046006).

"Receptor α" refers to the IL-2Rα or IL-15Rα.

"IL-15Rα derivative" refers to a polypeptide comprising an amino acid sequence having a percentage of identity of at least 92%, preferably of at least 96%, more preferably of at least 98%, and even more preferably of at least 99%, and most preferably 100% identical with the amino acid sequence of the sushi domain of human IL-15Rα (SEQ ID NO: 6) and, preferably of the sushi+ domain of human IL-15Rα (SEQ ID NO: 7). Preferably, the IL-15Rα derivative is a N- and C-terminally truncated polypeptide, whereas the signal peptide (amino acids 1-30 of SEQ ID NO: 5) is deleted and the transmembrane domain and the intracytoplasmic part of IL-15Rα is deleted (amino acids 210 to 267 of SEQ ID NO: 5). Accordingly, preferred IL-15Rα derivatives comprise at least the sushi domain (aa 33-93 but do not extend beyond the extracellular part of the mature IL-15Rα being amino acids 31-209 of SEQ ID NO: 5. Specific preferred IL-15Rα derivatives are the sushi domain of IL-15Rα (SEQ ID NO: 6), the sushi+ domain of IL-15Rα (SEQ ID NO: 7) and a soluble form of IL-15Rα (from amino acids 31 to either of amino acids 172, 197, 198, 199, 200, 201, 202, 203, 204 or 205 of SEQ ID NO: 5, see WO 2014/066527, (Giron-Michel et al. 2005)). Within the limits provided by this definition, the IL-15Rα, derivative may include natural occurring or introduced mutations. Natural variants and alternative sequences are e.g. described in the UniProtKB entry Q13261 (https:/www.uniprot.org/uniprot/Q13261). Further, the artisan can easily identify less conserved amino acids between mammalian IL-15Rα homologs or even primate IL-15Rα homologs in order to generate derivatives which are still functional. Respective sequences of mammalian IL-15Rα homologs are described in WO 2007/046006, page 18 and 19. Additionally or alternatively, the artisan can easily make conservative amino acid substitutions.

Preferably, an IL-15Rα derivative has at least 10% of the binding activity of the human sushi domain to human IL-15, e.g. as determined in (Wei et al. 2001), more preferably at least 25%, even more preferably at least 50%, and most preferably at least 80%.

"IL-2Rβ" refers to the human IL-Rβ or CD122.

"IL-2Rγ" refers to the common cytokine receptor γ or γ$_c$ or CD132, shared by IL-4, IL-7, IL-9, IL-15 and IL-21.

"RLI-15" refers to an IL-15/IL-15Rα complex being a receptor-linker-interleukin fusion protein of the human IL-15Rα sushi+ fragment with the human IL-15. Suitable linkers are described in WO 2007/046006 and WO 2012/175222.

"RLI2" or "SO-C101" are specific versions of RLI-15 and refer to an IL-15/IL-15Rα complex being a receptor-linker-interleukin fusion protein of the human IL-15Rα sushi+ fragment with the human IL-15 (SEQ ID NO: 9) using the linker with the SEQ ID NO: 8.

"ALT-803" refers to an IL-15/IL-15Rα complex of Altor BioScience Corp., which is a complex containing 2 molecules of an optimized amino acid-substituted (N72D) human IL-15 "superagonist", 2 molecules of the human IL-15α receptor "sushi" domain fused to a dimeric human IgG1 Fc that confers stability and prolongs the half-life of the IL-15$_{N72D}$:IL-15Rα$_{sushi}$-Fc complex (see for example US 2017/0088597).

"Heterodimeric IL-15:IL-Rα", "hetIL-15" or "NIZ985" refer to an IL-15/IL-15Rα complex of Novartis which resembles the IL-15, which circulates as a stable molecular complex with the soluble IL-15Rα, which is a recombinantly co-expressed, non-covalent complex of human IL-15 and the soluble human IL-15Rα (sIL-15Rα), i.e. 170 amino acids of IL-15Rα without the signal peptide and the transmembrane and cytoplasmic domain (Thaysen-Andersen et al. 2016, see e.g. table 1).

"IL-2/IL-2Rβγ agonists" refers to molecules or complexes which primarily target the mid-affinity IL-2/IL-15Rβγ receptor without binding to the IL-2Rα and/or IL-15Rα receptor, thereby lacking a stimulation of T$_{regs}$. Examples are IL-15 bound to at least the sushi domain of the IL-15Rα having the advantage of not being dependent on trans-presentation or cell-cell interaction, and of a longer in vivo half-life due to the increased size of the molecule, which have been shown to be significantly more potent that native IL-15 in vitro and in vivo (Robinson and Schluns 2017). Besides IL-15/IL-15Rα based complexes, this can be achieved by mutated or chemically modified IL-2, which have a markedly reduced or timely delayed binding to the IL-2α receptor without affecting the binding to the IL-2/15Rβ and γ$_C$ receptor.

"NKTR-214" refers to an IL-2/IL-15Rβγ agonist based on IL-2, being a biologic prodrug consisting of IL-2 bound by 6 releasable polyethylene glycol (PEG) chains (WO 2012/065086A1). The presence of multiple PEG chains creates an inactive prodrug, which prevents rapid systemic immune activation upon administration. Use of releasable linkers allows PEG chains to slowly hydrolyze continuously forming active conjugated IL-2 bound by 2-PEGs or 1-PEG. The location of PEG chains at the IL-2/IL-2Rα interface interferes with binding to high-affinity IL-2Rα, while leaving binding to low-affinity IL-2Rβ unperturbed, favoring immune activation over suppression in the tumor (Charych et al. 2016, Charych et al. 2017).

"IL2v" refers to an IL-2/IL-15Rβγ agonist based on IL-2 by Roche, being an IL-2 variant with abolished binding to the IL-2Rα subunit with the SEQ ID NO: 10. IL2v is used for example in fusion proteins, fused to the C-terminus of an antibody. IL2v was designed by disrupting the binding capability to IL-2Rα through amino acid substitutions F42A, Y45A and L72G (conserved between human, mouse and non-human primates) as well as by abolishing O-glycosylation through amino acid substitution T3A and by avoidance of aggregation by a C125A mutation like in aldesleukin (numbering based on UniProt ID P60568 excluding the signal peptide) (Klein et al. 2017). IL2v is used as a fusion partner with antibodies, e.g. with untargeted IgG (IgG-IL2v) in order to increase its half-life (Bacac et al. 2017). In RG7813 (or cergutuzumab amunaleukin, RO-6895882, CEA-IL2v) IL2v is fused to an antibody targeting carcinoembryonic antigen (CEA) with a heterodimeric Fc devoid of FcγR and C1q binding (Klein 2014, Bacac et al. 2016, Klein et al. 2017). And, in RG7461 (or RO6874281 or FAP-IL2v) IL2v is fused to the tumor specific antibody targeting fibroblast activation protein-alpha (FAP) (Klein 2014).

THOR-707 refers to an IL-2/IL-15Rβγ agonist based on a site-directed, singly PEGylated form of IL-2 with reduced/lacking IL2Rα chain engagement while retaining binding to the intermediate affinity IL-2Rβγ signaling complex (Joseph et al. 2019) (WO 2019/028419A1).

NL-201 refers to IL-2/IL-15Rβγ agonists, which is are computationally designed protein that mimics IL-2 to bind to the IL-2 receptor βγ$_c$ heterodimer (IL-2Rβγ$_c$) but has no binding site for IL-2Rα or IL-15Rα (Silva et al. 2019).

NKRT-255 refers to an IL-2/IL-15Rβγ agonist based on a PEG-conjugated human IL-15 that retains binding affinity to the IL-15Rα and exhibits reduced clearance to provide a sustained pharmacodynamic response (WO 2018/213341A1).

THOR-924, -908, -918 refer to IL-2/IL-15Rβγ agonists based on PEG-conjugated IL-15 with reduced binding to the IL-15Rα with a unnatural amino acid used for site-specific PEGylation (WO 2019/165453A1).

"Percentage of identity" between two amino acids sequences means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compare the local regions of similarity. The best sequences alignment to perform comparison can be realized, beside by a manual way, by using the global homology algorithm developed by Smith and Waterman (1981), by using the local homology algorithm developed by Needleman and Wunsch (1970), by using the method of similarities developed by Pearson and Lipman (1988), by using computer software using such algorithms (GAP, BESTFIT, BLAST P, BLAST N, FASTA, TFASTA in the Wisconsin Genetics software Package, Genetics Computer Group, 575 Science Dr., Madison, WI USA), by using the MUSCLE multiple alignment algorithms (Edgar 2004), or by using CLUSTAL (Goujon et al. 2010). To get the best local alignment, one can preferably use the BLAST software with the BLOSUM 62 matrix. The identity percentage between two sequences of amino acids is determined by comparing these two sequences optimally aligned, the amino acids sequences being able to encompass additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

Conservative amino acid substitutions refers to a substation of an amino acid, where an aliphatic amino acid (i.e. Glycine, Alanine, Valine, Leucine, Isoleucine) is substituted by another aliphatic amino acid, a hydroxyl or sulfur/selenium-containing amino acid (i.e. Serine, Cysteine, Selenocysteine, Threonine, Methionine) is substituted by another hydroxyl or sulfur/selenium-containing amino acid, an aromatic amino acid (i.e. Phenylalanine, Tyrosine, Tryptophan) is substituted by another aromatic amino acid, a basic amino acid (i.e. Histidine, Lysine, Arginine) is substituted by another basic amino acid, or an acidic amino acid or its amide (Aspartate, Glutamate, Asparagine, Glutamine) is replaced by another acidic amino acid or its amide.

"In vivo half-life" or T½ refers to the time required for a quantity of a drug to be reduced to half of its initial amount in vivo. The in vivo half-life of a particular drug can be determined in any mammal. For example, the in vivo half-life can be determined in humans, primates or mice. While the in vivo half-life determined in humans may considerably differ from the in vivo half-life in mice, i.e., the in vivo half-life in mice for a certain drug is commonly shorter than the in vivo half-life determined for the same drug in humans, such in vivo half-life determined in mice still gives an indication for a certain in vivo half-life in humans. Hence, from the in vivo half-life determined for a particular drug in mice, the in vivo half-life of the drug in humans can be extrapolated. This is particularly important since the direct determination of the in vivo half-life of a certain drug in humans is rarely possible due to prohibitions of experiments for merely scientific purposes involving humans. Alternatively, the half-life can be determined in primates (e.g. cynomolgus monkeys) which is more similar to the half-life in humans. More specifically, the "in vivo half-life", (terminal) plasma half-life or T½ is the half-life of elimination or half-life of the terminal phase, i.e. following administration the in vivo half-life is the time required for plasma/blood concentration to decrease by 50% after pseudo-equilibrium of distribution has been reached (Toutain and Bousquet-Melou 2004). The determination of the drug, here the IL-2/IL-15βγ agonist being a polypeptide, in the blood/plasma is typically done through a polypeptide-specific ELISA.

"Immune check point inhibitor", or in short "check point inhibitors", refers to a type of drug that blocks certain proteins made by some types of immune system cells, such as T cells, and some cancer cells. These proteins help keeping immune responses in check and can keep T cells from killing cancer cells. When these proteins are blocked, the "brakes" on the immune system are released and T cells are able to kill cancer cells better. Checkpoint inhibitors are accordingly antagonists of immune inhibitory checkpoint molecules or antagonists of agonistic ligands of inhibitory checkpoint molecules. Examples of checkpoint proteins found on T cells or cancer cells include PD-1/PD-L1 and CTLA-4/B7-1/B7-2 (definition of the National Cancer Institute at the National Institute of Health, see https://www.cancer.gov/publications/dictionaries/cancer-terms/def/immune-checkpoint-inhibitor), as for example reviewed by Darvin et al. (2018). Examples of such check point inhibitors are anti-PD-L1 antibodies, anti-PD-1 antibodies, anti-CTLA-4 antibodies, but also antibodies against LAG-3 or TIM-3, or blocker of BTLA currently being tested in the clinic (De Sousa Linhares et al. 2018). Further promising check point inhibitors are anti-TIGIT antibodies (Solomon and Garrido-Laguna 2018).

"anti-PD-L1 antibody" refers to an antibody, or an antibody fragment thereof, binding to PD-L1. Examples are avelumab, atezolizumab, durvalumab, KN035, MGD013 (bispecific for PD-1 and LAG-3).

"anti-PD-1 antibody" refers to an antibody, or an antibody fragment thereof, binding to PD-1. Examples are pembrolizumab, nivolumab, cemiplimab (REGN2810), BMS-936558, SHR1210, IBI308, PDR001, BGB-A317, BCD-100, JS001.

"anti-PD-L2 antibody" refers to an antibody, or an antibody fragment thereof, binding to anti-PD-L2. An example is sHIgM12.

"an anti-CTLA4 antibody" refers to an antibody, or an antibody fragment thereof, binding to CTLA-4. Examples are ipilimumab and tremelimumab (ticilimumab).

"anti-LAG-3" antibody refers to an antibody, or an antibody fragment thereof, binding to LAG-3. Examples of anti-LAG-3 antibodies are relatlimab (BMS 986016), Sym022, REGN3767, TSR-033, GSK2831781, MGD013 (bispecific for PD-1 and LAG-3), LAG525 (IMP701).

"anti-TIM-3 antibody" refers to an antibody, or an antibody fragment thereof, binding to TIM-3. Examples are TSR-022 and Sym023.

"anti-TIGIT antibody" refers to an antibody, or an antibody fragment thereof, binding to TIGIT. Examples are tiragolumab (MTIG7192A, RG6058) and etigilimab (WO 2018/102536).

"Therapeutic antibody" or "tumor targeting antibody" refers to an antibody, or an antibody fragment thereof, that has a direct therapeutic effect on tumor cells through binding of the antibody to the target expressed on the surface of the treated tumor cell. Such therapeutic activity may be due to receptor binding leading to modified signaling in the cell, antibody-dependent cellular cytotoxicity (ADCC), complement-dependent cytotoxicity (CDC) or other antibody-mediated killing of tumor cells.

"anti-CD38 antibody" refers to an antibody, or an antibody fragment thereof, binding to CD38, also known as cyclic ADP ribose hydrolase. Examples of anti-CD38 antibodies are daratumumab, isatuximab (SAR650984), MOR-202 (MOR03087), TAK-573 or TAK-079 (Abramson 2018) or GEN1029 (HexaBody®-DR5/DR5).

"about", when used together with a value, means the value plus/minus 10%, preferably 5% and especially 1% of its value.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

The term "at least one" such as in "at least one chemotherapeutic agent" may thus mean that one or more chemotherapeutic agents are meant. The term "combinations thereof" in the same context refers to a combination comprising more than one chemotherapeutic agents.

Technical terms are used by their common sense. If a specific meaning is conveyed to certain terms, definitions of terms will be given in the following in the context of which the terms are used.

"qxw", from Latin quaque/each, every for every x week, e.g. q2w for every second week.
"s.c." for subcutaneously.
"i.v." for intravenously.
"i.p." for intraperitoneally.

DESCRIPTION OF THE INVENTION

Pulsed Cyclic Dosing

In a first aspect, the present invention relates to an interleukin-2/interleukin-15 receptor βγ (IL-2/IL-15Rβγ) agonist for use in treating or managing cancer or infectious diseases, comprising administering the IL-2/IL-15Rβγ agonist to a human patient using a cyclical administration regimen, wherein the cyclical administration regimen comprises:

(a) first period of x days during which the IL-2/IL-15Rβγ agonist is administered at a daily dose on y consecutive days at the beginning of the first period followed by x-y days without administration of the IL-2/IL-15Rβγ agonist, wherein x is 5, 6, 7, 8, 9, 10, 11, 12, 13, 14, 15, 16, 17, 18, 19, 20 or 21 days, preferably, 7 or 14 days, and y is 2, 3 or 4 days, preferably 2 or 3 days;

(b) repeating the first period at least once; and (c) a second period of z days without administration of the IL-2/IL-15Rβγ agonist, wherein z is 5, 6, 7, 8, 9, 10, 11, 12, 13, 14, 15, 16, 17, 18, 19, 20, 21, 28, 35, 42, 49, 56, 63 or 70 days, preferably 7, 14, 21 or 56 days, more preferably 7 or 21 days. For illustration, a graphical representation of the dosing is depicted in FIG. 21. In a more preferred embodiment, y is 2 days and x is 7 days.

In one embodiment the present invention relates to an interleukin-2/interleukin-15 receptor βγ (IL-2/IL-15Rβγ) agonist for use in treating or managing cancer or infectious diseases, comprising administering the IL-2/IL-15Rβγ agonist to a human patient using a cyclical administration regimen, wherein the cyclical administration regimen comprises:

(a) first period of x days during which the IL-2/IL-15Rβγ agonist is administered at a daily dose on y consecutive days at the beginning of the first period followed by x-y days without administration of the IL-2/IL-15Rβγ agonist, wherein x is 14 or 21 days, preferably 14 days, and y is 2, 3 or 4 days, preferably 2 or 3 days;

(b) repeating the first period at least once; and (c) a second period of z days without administration of the IL-2/IL-15Rβγ agonist, wherein z is 7, 8, 9, 10, 11, 12, 13, 14, 15, 16, 17, 18, 19, 20, 21, 28, 35, 42, 49, 56, 63 or 70 days, preferably 7, 14, 21 or 56 days, more preferably 7 or 21 days. In a more preferred embodiment, x is 14 days, y is 2, 3 or 4 days and z is 14 days. Especially in the case of a longer pulse of 4 days the first period of x days may be required to be longer than 7 days, i.e. to stay in a weekly scheme 14 or 21 days.

In a second aspect, the present invention relates to an interleukin-2/interleukin-15 receptor βγ (IL-2/IL-15Rβγ) agonist for use in treating or managing cancer or infectious diseases, comprising administering the IL-2/IL-15Rβγ agonist to a human patient using a cyclical administration regimen, wherein the cyclical administration regimen comprises:

(a) a first period of x days during which the IL-2/1L-15Rβγ agonist is administered at a daily dose on y consecutive days at the beginning of the first period followed by x-y days without administration of the IL-2/IL-15Rβγ agonist, wherein x is 5, 6, 7, 8 or 9 days, and y is 2, 3 or 4 days;

(b) repeating the first period at least once; and (c) a second period of z days without administration of the IL-2/IL-15Rβγ agonist, wherein z is 5, 6, 7, 8, 9, 10, 11, 12, 13, 14, 15, 16, 17, 18, 19 or 20 days. For illustration, a graphical representation of the dosing is depicted in FIG. 21.

This administration scheme can be described as a "pulsed cyclic" dosing "pulsed" as the IL-2/IL-15Rβγ agonist is administered e.g. at day 1 and day 2 of a week activating and expanding both NK and CD8⁺ T cells (a "pulse"), followed by no administration of the agonist for the rest of the week (step (a). This on/off administration is repeated at least once, e.g. for two or three weeks (step (b)), followed by another period without an administration of the IL-2/1L-15Rβγ agonist, e.g. another week (step (c)). Accordingly, examples of a cycle are (a)-(a)-(c) ((a) repeated once) or (a)-(a)-(a)-(c) ((a) repeated twice). Pulsed dosing occurs in the first period according to step (a) and in the repetition of the first period in step (b). Step (a), (b) and (c) together, i.e., the pulsed dosing in combination with the second period without administration of the IL-2/IL-15Rβγ agonist, are referred to as one cycle or one treatment cycle. This whole treatment cycle (first periods and second period) may then be repeated multiple times.

The inventors surprisingly found that in cynomolgus monkeys the pulsed dosing of the IL-2/IL-15Rβγ agonist RLI-15/SO-C101 on consecutive days lead to a strong, dose dependent activation of NK cells and CD8⁺ T cells (measured by determining the expression of Ki67, i.e. becoming Ki67⁺) both for i.v. and s.c. administration. At the same time $T_{regs}$ were not induced. It was surprising that after a $1^{st}$ administration of an IL-2/IL-15Rβγ agonist in primates on day 1, a $2^{nd}$ administration of the same dose on day 2 lead to a further increase in activation of both NK cells and CD8⁺ T cells. A $4^{th}$ administration on day 4 did not result in a further increase of activation, but still kept the activation levels high. A rest period of several days was then sufficient to achieve similar levels of activation in a second pulse.

RLI-15 provides optimal activation of NK cells and CD8⁺ T cells with two consecutive daily doses per week in primates. This is surprising given the relatively short half-life of RLI-15, leading to high levels of proliferating NK cells and CD8⁺ T cells still 4 days after the first, and 3 days after the second dosing.

A long-term continuous stimulation of the mid-affinity IL-2/IL-15Rβγ receptor may not provide any additional benefit in the stimulation of NK cells and CD8⁺ T cells compared to relative short stimulation by two consecutive daily doses with a relative short-lived IL-2/IL-15Rβγ receptor agonist such as R11-15. To the contrary, continuous stimulation by too frequent dosing or agonists with significantly longer half-life may even cause exhaustion and anergy of the NK cells and CD8⁺ T cells in primates.

The pulsed cyclic dosing and the pulsed dosing provided herein is in contrast to previously described dosing regimens for IL-2/IL-15Rβγ agonist tested in primates and humans applying continuous dosing of such agonists, trying to optimize AUC and $C_{max}$ over time similar to a classical drug, i.e. aiming for constant drug levels and hence continuous stimulation of the effector cells.

For example, IL-2 and IL-15 are dosed continuously: IL-2 i. v. bolus over 15 min every 8 hours; and IL-15 s.c. days 1-8 and 22-29, or i. v. continuous infusion for 5 or 10 consecutive days, or i. v. daily for 12 consecutive days (see clinical trials: NCT03388632, NCT01572493, NCT01021059). The IL-2/IL-15Rβγ agonist hetIL-15 was dosed in primates continuously on days 1, 3, 5, 8, 10, 12 and 29, 31, 33, 36, 38 and 40 (i.e. always day 1, 3 and 5 of a week). A lack of responsiveness was tried to be overcome by increasing the dose of the IL-2/IL-15Rβγ agonist up to rather high doses of 64 μg/kg (Bergamaschi et al. 2018), much higher than tolerated in humans (Conlon et al. 2019). In humans hetIL-15 (NIZ985) was dosed at 0.25 to 4.0 μg/kg 2 weeks-on/2 weeks-off administered s.c. again three times a week (TIW) (Conlon et al. 2019). In comparison, the ALT-803 was administered in a human clinical trial once per week (on weeks 1 to 5 of four 6-week cycles) (Wrangle et al. 2018). And NKT-214 is dosed once every 3 weeks.

The finding of the inventors was further in contrast to report by Frutoso et al., where in a pulsed dosing in mice (day 1 and day 3 followed by a treatment break) the second stimulation with IL-15 or an IL-2/IL-15Rβγ agonist did not lead to a marked activation of NK cells in vivo (Frutoso et al. 2018).

In one embodiment the IL-2/IL-15Rβγ agonist is for use in the cyclic administration regimen, wherein x is 6, 7 or 8 days, preferably 7 days. For convenience reasons, it is advantageous that patients are treated in weekly rhythm, especially if such rhythm is to be repeated over many weeks, i.e. x is preferably 7 days, but one can reasonably assume that changing the rhythm to 6 or 8 days would not have a major impact on the treatment result making 6 or 8 days also preferred embodiments.

In another embodiment, the IL-2/IL-15Rβγ agonist is for use in the cyclic administration regimen, wherein y is 2 or 3 days, preferably 2 days. It was shown in the cynomolgus monkeys that optimal activation (measures as Ki67$^+$) of both NK cells and CD8$^+$ T cells can be reached by 2 daily administrations per week on 2 consecutive days, whereas 4 daily consecutive administrations within one week did not provide any additional benefit with respect to activated NK cells and CD8$^+$ T cells. In other words, the activation of NK cells and CD8$^+$ T cells reached a plateau between the $2^{nd}$ and the $4^{th}$ administration. Accordingly, 2 and 3, more preferably 2 consecutive daily administrations are preferred in order to minimize exposure of the patient to the drug, but still achieve high levels of activation of the effector cells.

In another embodiment the IL-2/IL-15Rβγ agonist is for use in the cyclic administration regimen, wherein z is 6, 7 or 8 days. In order to stay in a weekly rhythm for convenience of the patients, the period z, where no administration of the IL-2/IL-15Rβγ agonist occurs, is preferably 7 or 14 days, more preferably 7 days.

The dosing regimen according to the invention may be preceded by a pre-treatment period, where the IL-2/IL-15Rβγ agonist is dosed at a lower daily dose, administered less frequently or where an extended treatment break is applied in order to test the response of the patient or get the patient used to the treatment or prime the immune system for a subsequent higher immune cell response.

For example it is envisaged that there is one additional treatment cycle as pre-treatment with y days of treatment (e.g. 2 or 3 days) in the treatment period x (e.g. 7 days), whereas z is extended compared to the following treatment cycles (e.g. 14 days instead of 7 days).

In an especially preferred embodiment the IL-2/IL-15Rβγ agonist is for use in the cyclic administration regimen, wherein x is 7 days, y is 2 days and z is 7 days. This especially preferred treatment cycle of 2 administrations on 2 consecutive days, followed by 7-2=5 days without administration and therefore making a weekly cycle combines the minimal exposure of 2 administrations of the IL-2/IL-15Rβγ agonist achieving the maximum activation of the NK cells and CD8$^+$ T cells with the convenient weekly cycling for the patient.

In an especially preferred embodiment the IL-2/IL-15Rβγ agonist is for use in the cyclic administration regimen, wherein x is 7 days, y is 2, 3 or 4 days and z is 7 days. Whereas 2 administrations on 2 consecutive days already showed already maximum activation of NK cells and CD8+ cells, 4 administrations on 4 consecutive days maintained such activation for another two days without leading to a marked decrease of activated NK cells and CD8+ cells. Therefore, an alternative preferred treatment regimen is, wherein x is 7 days, y is 3 days and z is 7 days, i.e. 3 administrations on 3 consecutive days followed by 7-3=4 days without administration, which may be beneficial if a prolonged activation of the NK cells and CD8$^+$ T cells translates into higher efficacy. And, another alternative preferred treatment regimen is, wherein x is 7 days, y is 4 days and z is 7 days, i.e. 4 administrations on 4 consecutive days followed by 7-4=3 days without administration, which may be beneficial if a prolonged activation of the NK cells and CD8$^+$ T cells translates into higher efficacy.

In one embodiment, the IL-2/IL-15Rβγ agonist is for use in the cyclic administration regimen, wherein the daily dose is 0.1 µg/kg (0.0043 µM) to 50 µg/kg (2.15 µM) of the IL-2/IL-15Rβγ agonist.

In one embodiment the IL-2/IL-15Rβγ agonist is for use in the cyclic administration regimen, wherein the daily dose is 0.0043 µM to 2.15 µM of the IL-2/IL-15Rβγ agonist.

The present inventors could show a good correlation between RLI-15/SO-C101 (for which 1 µM equals 23 µg/kg) and NK and CD8$^+$ T cell proliferation in vitro for human NK cells and CD8$^+$ T cells and in vivo data obtained from cynomolgus monkeys. From this correlation, it is possible to predict the Minimal Anticipated Biologic Effect Level (MABEL) at about 0.25 µg/kg, the Pharmacologic Active Doses (PAD) at between about 0.6 µg/kg and 10 µg/kg together with the No Observed Adverse Effect Level (NOAEL) at about 25 µg/kg and the Maximum Tolerated Dose (MTD) at about 32 µg/kg for RLI-15 and IL-2/IL-15Rβγ agonists, preferably of an IL-2/IL-15Rβγ agonist with about the same molecular weight. These values equal a MABEL of about 0.011 µM of the IL-2/IL-15Rβγ agonist, a PAD at between about 0.026 µM and 0.43 µM of the IL-2/IL-15Rβγ agonist, a NOAEL at about 1.1 µM of the IL-2/IL-15Rβγ agonist and the MTD at about 1.38 µM of the IL-2/IL-15Rβγ agonist.

Considering potential deviations from the predictions, a starting dose of 0.1 µg/kg (0.0043 µM) for a clinical trial has been determined and the observed MTD in humans may be up to 50 µg/kg (2.15 µM). Preferably, the dose is between 0.25 µg/kg (0.011 µM) (MABEL) and 25 µg/kg (1.1 µM) (NOAEL), more preferably between 0.6 µg/kg (0.026 µM) and 10 µg/kg (0.43 µM) (PAD), more preferably from 1 µg/kg (0.043 µM) to 15 µg/kg (0.645 µM), and especially 2 (0.087 µM) µg/kg to 10 µg/kg (0.43 µM).

Accordingly, in another embodiment, the IL-2/IL-15Rβγ agonist is for use in the cyclic administration regimen, wherein the daily dose is 0.0043 µM to 2.15 µM of the IL-2/IL-15Rβγ agonist, preferably the dose is between 0.011 µM (MABEL) and 1.1 µM (NOAEL), and more preferably between 0.026 µM and 0.43 µM (PAD).

In a preferred embodiment the IL-2/IL-15Rβγ agonist is for use in the cyclic administration regimen, wherein the daily dose selected within the dose range of 0.1 to 50 µg/kg, preferably 0.25 to 25 µg/kg, more preferably 0.6 to 10 µg/kg and especially 2 to 10 µg/kg, is not substantially increased during the administration regimen, preferably wherein the dose is maintained during the administration regime. Surprisingly, the administration regimen according to the invention showed repeated activation of NK cells and CD8$^+$ T cells and did not require a dose increase over time. This has not been observed for example in the dose regimen used for hetIL-15, which was compensated by progressively doubling doses from 2 to 64 µg/kg (Bergamaschi et al. 2018). Therefore, it is an important advantage that the selected daily dose within the range of 0.1 to 50 µg/kg does not have to be increased within repeating the first period of administration, or from one cycle to the next. This enables repeated cycles of the treatment without running the risk of getting into toxic doses or that the treatment over time becomes ineffective. Further, maintaining the same daily dose during the administration regimen ensures higher compliance as doctors or nurses do not need to adjust the doses from one treatment to another.

In one embodiment, the IL-2/IL-15Rβγ agonist is for use in the cyclic administration regimen, wherein the daily dose is 3 μg/kg (0.13 μM) to 20 μg/kg (0.87 μM), preferably 6 μg/kg (0,26 μM) to 12 μg/kg (0.52 μM) of the IL-2/IL-15Rβγ agonist.

In one embodiment the IL-2/IL-15Rβγ agonist is for use in the cyclic administration regimen, wherein the daily dose is a fixed dose independent of body weight of 7 μg to 3500 μg (0.30 mol to 150 mol), preferably 17.5 μg to 1750 μg (0.76 mol to 76 mol), more preferably 42 μg to 700 μg (1.8 mol to 30 mol) and especially 140 μg to 700 μg (6.1 mol to 30 mol).

In one embodiment the IL-2/IL-15Rβγ agonist is for use in the cyclic administration regimen, wherein the daily dose is increased during the administration regime. As the IL-2/IL-15Rβγ agonist leads to an expansion of the cells expressing the IL-2/IL-15Rβγ receptor and to an enhanced expression of the receptor on the surface, equal doses of the agonist will over time lead to a decreased plasma concentration of the agonist, as more agonist molecules will be bound to the cells. In order to compensate for the molecules being more and more captured by the target cells, the daily dose is preferably increased during the administration regime.

Such increase of the daily dose may preferably occur after each period of x days. Typically, such increases can best be operationally be managed if increases occur after each pulse of x days. Especially CD8$^+$ T cells appear to be lose sensitivity to stimulation by the IL-2/IL-15Rβγ agonist after a pulse treatment of x days. Accordingly, it is preferred the increase the daily dose after each pulse of x days (until the upper limit of a tolerated daily dose is reached).

In one embodiment, the next treatment cycle starts again at the initial daily dose and is increased again after each pulse of x days (see FIG. 21, option A). Alternatively, the next treatment cycle starts with the same daily dose as the last daily (increased) dose of the previous pulse of x days) (see (see FIG. 21, option B).

In one embodiment, the daily dose is increased by about 20% to about 100%, preferably by about 30% to about 50% after each period of x days in order to compensate for the expansion of the target cells.

Such increases would be limited by an upper limit, which cannot be exceeded due to e.g. dose limiting toxicities. Given the binding of the agonist to the target cells, this upper limit is however expected to dependent on the number of target cells, i.e. a patient with an expanded target cell compartment is expected to tolerate a higher dose of the agonist compared to an (untreated) patient with a lower number of target cells. Still, it is assumed that upper limit of a tolerated daily dose after dose increases is 50 μg/kg (2.15 μM), preferably 32 μg/kg (1.4 μM) and especially 20 μg/kg (0.87 μM).

In another embodiment, the daily dose is increased only once after the first period of x days, preferably by about 20% to about 100%, preferably by about 30% to about 50% after the first period of x days. Already one increase of the daily dose may reach the upper limit of a tolerated daily dose and further, during the z days without administration of the IL-2/IL-15Rβγ agonist levels of NK cells and CD8+ cells are expected to go back to nearly normal levels making one increase sufficient.

In another embodiment, the daily dose is increased after each daily dose within the pulse period y. Preferred embodiments are that for the next treatment period x within the same cycle, the next daily dose may then be further increased (see FIG. 21, option C) or continue at the same daily dose level as the last daily dose of the previous treatment period x (see FIG. 21, option D). Between treatment cycles, the daily dose may always start again at the initial dose level (see FIG. 21, option C and B) or continue at the increased dose level from the first treatment day of the preceding treatment period x (see FIG. 21, option E). Again, such increases would be limited by an upper limit, which cannot be exceeded due to e.g. dose limiting toxicities. Given the binding of the agonist to the target cells, this upper limit is however expected to dependent on the number of target cells, i.e. a patient with an expanded target cell compartment is expected to tolerate a higher dose of the agonist compared to an (untreated) patient with a lower number of target cells. Still, it is assumed that upper limit of a tolerated daily dose after dose increases is 50 μg/kg (2.15 μM), preferably 32 μg/kg (1.4 μM) and especially 20 μg/kg (0.87 μM).

In one embodiment the IL-2/IL-15Rβγ agonist is for use wherein the daily dose is administered in a single injection. Single daily injections are convenient for patients and healthcare providers and are therefore preferred.

However, given the short half-life of the molecule and the hypothesis that the activation of the immune cells being dependent on the increase of IL-2/IL-15Rβγ agonists rather than on continuous levels of such agonist, it is another preferred embodiment that the daily dose is split into 2 or 3 individual doses that are administered within one day, wherein the time interval between administration of the individual doses is at least about 4 h and preferably not more than 12 h (dense pulsed cyclic dosing). It is expected that the same amount of the agonist—split into several doses and administered during the day is more efficacious in stimulating in human patients NK cells and especially CD 8$^+$ cells, the latter showing a lower sensitivity for the stimulation, than administered only in a single injection. This has surprisingly been observed in mice. Practically, such multiple dosing should be able to be integrated into the daily business of hospitals, doctor's practice or outpatient settings and therefore, 2 to 3 equal doses administered during business hours including shifts between 8 and 12 hours would still be conveniently manageable, with 8 or 10 h intervals being preferred as the maximum time difference between first and last dose. Accordingly, it is a preferred embodiment that the daily dose is split into 3 individual doses that are administered within one day, wherein the time interval between administration of the individual doses is about 5 to about 7 h, preferably about 6 hours. This means that a patient could be dosed e.g. at 7 am, 2 pm and 7 pm every day (with 6-hour intervals), or at 7 am, 1 pm and 6 pm (with 5-hour intervals). In another preferred embodiment, the daily dose is split into 2 individual doses that are administered within one day, wherein the time interval between administration of the individual doses is about 6 h to about 10 h, preferably 8 h. In the case of 2 doses, a patient could be dosed e.g. at 8 am and 4 pm (with an 8-hour interval). Given the daily routine of hospitals, the intervals between the administrations may vary within a day or from day to day.

In another preferred embodiment, the IL-2/IL-15Rβγ agonist is for use in the cyclic administration regimen, wherein the IL-2/IL-15Rβγ agonist is administered subcutaneously (s.c.) or intraperitoneally (i.p.), preferably s.c. The inventors observed in a cynomolgus study that s.c. administration was more potent than i.v. administration with regards to activation of NK cells and CD8$^+$ T cells. I.p. administration has similar pharmacodynamics effects as s.c. administration. Therefore, i.p. administration is another preferred embodiment, especially for cancers originating from organs in the peritoneal cavity, e.g. ovarian, pancreatic, colorectal, gastric and liver cancer as well as peritoneal metastasis owing to locoregional spread and distant metastasis of extraperitoneal cancers.

In another embodiment, the IL-2/IL-15Rβγ agonist is for use in the cyclic administration regimen, wherein administration of the IL-2/IL-15Rβγ agonist in step (a) results in an increase of the % of Ki-67$^+$ NK of total NK cells in comparison to no administration of the IL-2/IL-15Rβγ agonist, and wherein administration of the IL-2/IL-15Rβγ agonist in step (b) results in a Ki-67$^+$ NK cell level that is at least 70% of the of the Ki-67$^+$ NK cells of step (a). Ki-67 is a marker for proliferating cells and therefore percentage of Ki-67$^+$ NK cell of total NK cells is a measure to determine the activation state of the respective NK cell population. It was surprisingly shown that repeating daily consecutive administrations after x-y days without administration of the agonist lead again to a strong activation of NK cells, which was at least 70% of the level of activation of the NK cells during the first period with daily administrations for x days (step a). The level of NK cell activation is measured as % of Ki-67$^+$ NK cells of total NK cells.

Still, in another embodiment the IL-2/IL-15Rβγ agonist is for use in the cyclic administration regimen, wherein the IL-2/IL-15Rβγ agonist administration results in maintenance of NK cell numbers or preferably an increase of NK cell numbers to at least 110% as compared to no administration of IL-2/IL-15Rβγ agonist after at least one repetition of the first period, preferably after at least two repetitions of the first period. Alternatively or additionally to measuring the NK cell activation, also total numbers of NK cells matter and it was shown that repeating daily consecutive administrations after x-y days without administration of the agonist lead on average to an increase in total numbers of NK cells over one or two repetitions of the first period (a). In absolute numbers the IL-2/IL-15Rβγ agonist administration resulted in NK cell numbers of at least about $1.1 \times 10^3$ NK cells/μl after at least one repetition of the first period, preferably after at least two repetitions of the first period.

In another embodiment the IL-2/IL-15Rβγ agonist is for use in the cyclic administration regimen, wherein the cyclic administration of is repeated over at least 3 cycles, preferably 5 cycles, more preferably at least 10 cycles and even more preferably until disease progression. Given the inventors' finding that, after an initial strong activation of NK cells and CD8$^+$ T cells in the phase 1 of the pharmacokinetic and pharmacodynamics study in the cynomolgus monkey by 4 consecutive daily administrations, followed by a treatment break of 18 days, NK cells and CD8$^+$ T cells can again be strongly activated, it can be reasonably concluded that the 2 or 3 repetitions of the daily administrations on consecutive days can be again repeated after a treatment break. Accordingly, repetition of at least 3 cycles, preferably 5 cycles or preferably at least 10 cycles for boosting the immune system are foreseen, e.g. for infectious diseases. As tumors often develop resistance to most treatment modalities, for the treatment of tumors it is especially foreseen to repeat cycles until disease progression.

The IL-2/IL-15Rβγ agonist is for use in the cyclic administration regimen, wherein the cancer is a hematological cancer or a solid cancer. As the mode of action of these agonists is an activation of the innate immune response through activation of NK cells and an activation of the adaptive immune response through activation of CD8$^+$ T cells, it is generally assumed that these agonists have great potential to treat both (advanced) solid tumors and hematological malignancies as tested already in numerous murine cancer models and a number of clinical trials in various tumor indications (Robinson and Schluns 2017). Accordingly, IL-2/IL-15Rβγ agonists were tested in colorectal cancer, melanoma, renal cell carcinoma, adenocarcinoma, carcinoid tumor, leiomyosarcoma, breast cancer, ocular melanoma, osteosarcoma, thyroid cancer, cholangiocarcinoma, salivary gland cancer, adenoid cystic carcinoma, gastric cancer, head and neck squamous cell carcinoma, ovarian cancer, urothelial cancer (Conlon et al. 2019). ALT-803 was tested in AML and MDS as examples for hematological malignancies (Romee et al. 2018). Especially advanced tumor diseases such as metastatic tumors patients may preferably profit from such treatment. In this respect ALT-803 has been tested accordingly in metastatic non-small cell lung cancer (Wrangle et al. 2018). The planned phase 1/1b clinical trial with SO-C101 (see example 9) will be open for patients having renal cell carcinoma, non-small cell lung cancer, small-cell lung cancer, bladder cancer, melanoma, Merkel-cell carcinoma, skin squamous-cell carcinoma, microsatellite instability high solid tumors, triple-negative breast cancer, mesothelioma, thyroid cancer, thymic cancer, cervical cancer, biliary track cancer, hepatocellular carcinoma, ovarian cancer, gastric cancer, head and neck squamous-cell carcinoma, and anal cancer. Examples of hematological cancers are leukemias such as acute lymphoblastic leukemia (ALL), acute myelogenous leukemia (AML), chronic lymphocytic leukemia (CLL), Chronic myelogenous leukemia (CML) and acute monocytic leukemia (AMoL), lymphomas such as Hodkin's lymphomas, Non-Hodkin's lymphomas, and myelomas.

Accordingly, renal cell carcinoma, non-small cell lung cancer, small-cell lung cancer, bladder cancer, melanoma, Merkel-cell carcinoma, skin squamous-cell carcinoma, microsatellite instability high solid tumors, triple-negative breast cancer, mesothelioma, thyroid cancer, thymic cancer, cervical cancer, biliary track cancer, hepatocellular carcinoma, ovarian cancer, gastric cancer, head and neck squamous-cell carcinoma, and anal cancer, and ALL, AML, CLL, CML, AMoL, Hodkin's lymphomas, Non-Hodkin's lymphomas, and myelomas are preferred cancer indications.

In another embodiment, the IL-2/IL-15Rβγ agonist is for use in the cyclic administration regimen, wherein the IL-2/IL-15Rβγ agonist has an in vivo half-life of 30 min to 24 h, preferably 1 h to 12 h, more preferably of 2 h to 6 h. Preferably, the in vivo half-life is the in vivo half-life as determined in mouse of 30 min to 12 h, more preferably 1 h to 6 h. In another preferred embodiment, the in vivo half-life is the in vivo half-life as determined in cynomolgus or macaques of 1 h to 24 h, more preferably of 2 h to 12 h. In another embodiment the in vivo half-life as determined in cynomolgus monkeys is 30 min to 12 hours, more preferably 30 min to 6 hours.

Pharmacokinetic and pharmacodynamic properties of the IL-2/IL-15Rβγ agonists of the invention depend on the in vivo half-life of such agonists. Due to various engineering techniques the in vivo half-life has been increased, e.g. by creating larger proteins by fusion to an Fc part of an antibody (e.g. ALT-803, RO687428) or antibodies (RG7813, RG7461, immunocytokines of WO 2012/175222A1, WO 2015/018528A1, WO 2015/109124) or PEGylation (NKT-214). However, a too long half-life may actually stimulate NK cells for too long, leading to a preferential accrual of mature NK cells with altered activation and diminished functional capacity (Elpek et al. 2010, Felices et al. 2018).

Therefore, the preferred IL-2/IL-15Rβγ agonist has an in vivo half-life of 30 min to 24 h, preferably 1 h to 12 h, more preferably of 2 h to 6 h, or preferably 30 min to 12 hours, more preferably 30 min to 6 hours. Preferably, this in vivo half-life refers to the half-life in humans. However, as the determination of the in vivo half-life in humans, if not published, may be unethical to determine, it is also preferred to use the in vivo half-life of mice or primates such as cynomolgus monkeys or macaques. Given the generally shorter half-life in mice, the in vivo half-life as determined in mouse is preferably. 30 min to 12 h, more preferably 1 h to 6 h or 30 min to 6 h, and the in vivo half-life as determined in cynomolgus or macaques of 1 h to 24 h, more preferably of 2 h to 12 h or 30 min to 6 h.

In another embodiment, the IL-2/IL-15Rβγ agonist is for use in the cyclic administration regimen, wherein the IL-2/IL-15Rβγ agonist is at least 70% monomeric, preferably at least 80% monomeric. Aggregates of such agonists may also have an impact on the pharmacokinetic and pharmacodynamic properties of the agonists and therefore should be avoided in the interest of reproducible results.

In another preferred embodiment, the IL-2/IL-15Rβγ agonist is for use in the cyclic administration regimen, wherein the IL-2/IL-15Rβγ agonist is an interleukin 15 (IL-15)/interleukin-15 receptor alpha (IL-15Rα) complex. IL-15/IL-15Rα complexes, i.e. complexes (covalent or non-covalent) comprising an IL-15 or derivative thereof and at least the sushi domain of the IL-15Rα or derivative thereof They target the mid-affinity IL-2/IL-15Rβγ, i.e. the receptor consisting of the IL-2/IL-15Rβ and the $\gamma_c$ subunits, which is expressed on NK cells, CD8$^+$ T cells, NKT cells and γδ T cells. These complexes are well-known in the art and their binding capabilities are well understood, whereas other attempts by modifying IL-2 to reduce/abandon IL-2Rα binding or synthetic approaches may face unpredictable risks. Preferably, the complex comprises a human IL-15 or a derivative thereof and the sushi domain of IL-15Rα (SEQ ID NO: 6), the sushi+ domain of IL-15Rα (SEQ ID NO: 7) or a soluble form of IL-15Rα (from amino acids 31 to either of amino acids 172, 197, 198, 199, 200, 201, 202, 203, 204 or 205 of SEQ ID NO: 5, see WO 2014/066527, (Giron-Michel et al. 2005)).

In a more preferred embodiment, the IL-15/IL-15Rα complex is a fusion protein comprising the human IL-15Rα sushi domain or derivative thereof, a flexible linker and the human IL-15 or derivative thereof, preferably wherein the human IL-15Rα, sushi domain comprises the sequence of SEQ ID NO: 6, more preferably comprising the sushi+ fragment (SEQ ID NO: 7), and wherein the human IL-15 comprises the sequence of SEQ ID NO: 4. Such fusion protein is preferably in the order (from N- to C-terminus) IL-15Rα-linker-IL-15 (RLI-15). An especially preferred IL-2/IL-15Rβγ agonist is the fusion protein designated RLI2 (SO-C101) having the sequence of SEQ ID NO: 9.

In another embodiment, the IL-2/IL-15Rβγ agonist is for use in the cyclic administration regimen, wherein a further therapeutic agent is administered in combination with the IL-2/IL-15Rβγ agonist. In the past years, cancer therapies are typically combined with existing or new therapeutic agents in order to tackle tumors through multiple mode of actions. At the same time, it is difficult or unethical to replace established therapies by new therapies, so typically new therapies are combined with the standard of care in order to achieve an additional benefit for the patient. Accordingly, also for the provided dosing regimens, these have to be combined with regimens of other therapeutic drugs. The further therapeutic agent and the IL-2/IL-15Rβγ agonist may be administered on the same days and/or on different days. Administration on the same day typically is more convenient for the patients as it minimizes visits to the hospital or doctor. On the other hand, scheduling the administration for different days may become important for certain combinations, where there may be an unwanted interaction between the agonist of the invention and another drug.

When it is stated "administered in combination" this typically does not mean that the two agents are co-formulated and co-administered, but rather one agent has a label that specifies its use in combination with the other. So, for example the IL-2/IL-15Rβγ agonist is for use wherein the use in treating or managing cancer or infectious diseases, comprising simultaneously, separately, or sequentially administering of the IL-2/IL-15Rβγ agonist and a further therapeutic agent, or vice e versa. But nothing in this application should exclude that the two combined agents are provided as a bundle or kit, or even are co-formulated and administered together where dosing schedules match.

As the typical clinical development path is the combination with standard of care, the administration of the combination agent is maintained and therefore is independent of the administration regimen of the IL-2/IL-15Rβγ agonist.

In another embodiment, the IL-2/IL-15Rβγ agonist is for use in the cyclic administration regimen, wherein the further therapeutic agent is an immune checkpoint inhibitor (or in short checkpoint inhibitor) or a therapeutic antibody.

Preferably, the checkpoint inhibitor or the therapeutic antibody is administered at the beginning of each period (a) of each cycle. In order to warrant high compliance with the timely dosing of the therapeutic agents and to minimize procedures, the treatment cycles of the agonist and the checkpoint inhibitor or the therapeutic antibody are ideally started together, e.g. in the same week. Depending on potential interactions between the agonist and the combined antibody, this may be the same day, or at different days in the same week. For example, expanding the NK cells and CD8$^+$ T cells first for 1, 2, 3 or 4 days before adding the checkpoint inhibitor or the therapeutic antibody may result in improved efficacy of the treatment.

In one embodiment, the IL-2/IL-15Rβγ agonist is for use, wherein the x days and z days are adapted that an integral multiple of x days+z days (n×x+z with n∈{2, 3, 4, 5, . . . }) equal the days of one treatment cycle of the checkpoint inhibitor or the therapeutic antibody, or, if the treatment cycle of the checkpoint inhibitor or the therapeutic antibody changes over time, equal to each individual treatment cycle of the checkpoint inhibitor or the therapeutic antibody.

For example, checkpoint inhibitors or therapeutic antibody are typically dosed every 3 or every 4 weeks. For example, the treatment schedule of the IL-2/IL-15Rβγ agonist of the present inventions matches with the treatment schedule of a checkpoint inhibitor, if both the IL-2/IL-15Rβγ agonist and the checkpoint inhibitor are administered at the beginning of the first period (a) (treatment period x), preferably at the first day of the first period (a), and the checkpoint inhibitor or therapeutic antibody is not further administered for the rest of the treatment cycle. For every following treatment cycle the check point inhibitor or therapeutic antibody is then again administered at the beginning, preferably on the first day, of period (a). Accordingly, if x is 7 (i.e. a week) and (a) is repeated once (so the integral multiple n is 2) and z is 7, the checkpoint inhibitor or therapeutic antibody would be administered every 3 weeks (2×7+7=3 weeks), or, if x is 7 and (a) is repeated twice (so the integral multiple n is 3) and z is 7, the checkpoint inhibitor or therapeutic antibody would be administered every 4 weeks (3×7+7=4 weeks). In case of a 6-week schedule of the checkpoint inhibitor or therapeutic antibody, the agonist may either be scheduled as to 3 week cycles (2×7+7) or one 6 week cycle (5×7+7 or 4×7+14). In case the treatment regimen of the checkpoint inhibitor or therapeutic antibody is changed over time, typically, the rhythm of the schedules is adapted by extending the period z to synchronize the rhythms, e.g. extending z=7 to z=14.

In a preferred embodiment, the checkpoint inhibitor may be an anti-PD-1 antibody, an anti-PD-L1 antibody, an anti-PD-L2 antibody, an anti-LAG3, an anti-TIM-3, an anti-CTLA4 antibody or an anti-TIGIT antibody, preferably an anti-PD-L1 antibody or an anti-PD-1 antibody. These antibodies have in common that they block/antagonize cellular interactions that block or downregulate immune cells, especially T cells from killing cancer cells, accordingly these antibodies are all antagonistic antibodies. Examples of anti-PD-1 antibodies are pembrolizumab, nivolumab, cemiplimab (REGN2810), BMS-936558, SHR1210, IBI308, PDR001, BGB-A317, BCD-100 and JS001; examples of anti-PD-L1 antibodies are avelumab, atezolizumab, durvalumab, KN035 and MGD013 (bispecific for PD-1 and LAG-3); an example for PD-L2 antibodies is sHIgM12; examples of anti-LAG-3 antibodies are relatlimab (BMS 986016), Sym022, REGN3767, TSR-033, GSK2831781, MGD013 (bispecific for PD-1 and LAG-3) and LAG525 (IMP701); examples of anti-TIM-3 antibodies are TSR-022 and Sym023; examples of anti-CTLA-4 antibodies are ipilimumab and tremelimumab (ticilimumab); examples of anti-TIGIT antibodies are tiragolumab (MTIG7192A, RG6058) and etigilimab.

Especially preferred is the combination of the IL-2/IL-15Rβγ agonist, especially SO-C101, for use in the cyclic administration regimen with pembrolizumab. Presently, pembrolizumab is administered every 3 weeks. Accordingly, it is a preferred embodiment that the agonist is administered in a 3-week cycle as well, i.e. x is 7 days and repeated twice with y being 2, 3 or 4 days, and z is 7 days. In one embodiment, pembrolizumab is either administered at the first day of each treatment cycle as is the agonist, or at any other day within such treatment cycle, preferably at day 3, day 4 or day 5 of such treatment cycle in order to allow for an expansion/activation of NK cells and CD8$^+$ T cells prior to the addition of the checkpoint inhibitor. In vitro experiments of present invention have shown that both concomitant and sequential treatment result in a marked increase of IFNγ production from PBMCs, showing. Recently, the label of pembrolizumab has been broadened to allow also for administration every 6 weeks. Compared to the schedules described in this section above, the schedule of the agonist would preferably adapted by either having two 3 week cycles (e.g. x=7 repeated once, z=7) or by having a 6 week cycle (e.g. x=7 repeated 4 times with z=7 or x=7 repeated 3 times with z=14).

In a preferred embodiment, the therapeutic antibody or tumor targeting antibody may be selected from an anti-CD38 antibody, an anti-CD19 antibody, an anti-CD20 antibody, an anti-CD30 antibody, an anti-CD33 antibody, an anti-CD52 antibody, an anti-CD79B antibody, an anti-EGFR antibody, an anti-HER2 antibody, an anti-VEGFR2 antibody, an anti-GD2 antibody, an anti-Nectin 4 antibody and an anti-Trop-2 antibody , preferably an anti-CD38 antibody. Such therapeutic antibody or tumor targeting antibody may be linked to a toxin, i.e. being an antibody drug conjugate. The therapeutic antibodies exert a direct cytotoxic effect on the tumor target cell through binding to the target expressed on the surface of the tumor cell. The therapeutic activity may be due to the receptor binding leading to modified signaling in the cell, antibody-dependent cellular cytotoxicity (ADCC), complement-dependent cytotoxicity (CDC) or other antibody-mediated killing of tumor cells. For example, the inventors have shown that the IL-2/IL-15Rβγ agonist RLI-15/SO-C101 synergizes with an anti-CD38 antibody (daratumumab) in tumor cell killing of Daudi cells in vitro both in a sequential and a concomitant setting, which was confirmed in a multiple myeloma model in vivo. Accordingly, anti-CD38 antibodies are especially preferred. Examples of anti-CD38 antibodies are daratumumab, isatuximab (SAR650984), MOR-202 (MOR03087), TAK-573 or TAK-079 or GEN1029 (HexaBody®-DR5/DR5), whereas most preferred is daratumumab. Preferably, daratumumab is administered according to its label, especially preferred via i.v. infusion and/or according to the dose recommended by its label, preferably at a dose of 16 mg/kg.

In a preferred embodiment, the IL-2/IL-15Rβγ agonist is for use, wherein an anti-CD38 antibody, preferably daratumumab, is administered in combination with the IL-2/IL-15Rβγ agonist, wherein (i) the anti-CD38 antibody is administered once a week for a first term of 8 weeks, (ii) followed by a second term consisting of 4 sections of 4 weeks (16 weeks), wherein during each 4 week section the anti-CD38 antibody is administered weekly in the first 2 weeks of the section followed by 2 weeks of no administration, (iii) followed by a third term with administration of the anti-CD38 antibody once every 4 weeks until disease progression. Therefore, it is preferred that the anti-CD38 antibody is administered once weekly for an initial 8 weeks, followed by 16 weeks of 2 treatments once per week and 2 weeks of treatment break, and thereafter once every 4 weeks until disease progression. Aligned to the treatment schedule of the IL-2/1L-15Rβγ agonist starting counting with day of the first treatment with the agonist, in weeks with anti-CD38 antibody administration, the anti-CD38 antibody is administered on the 1$^{st}$ day (concomitant treatment) or the 3$^{rd}$ day (sequential treatment) of the week. A treatment schedule with x=7 repeated once and z=14 matches with the first term of 8 weeks anti-CD38 treatment (see FIG. 13 A or B), followed by the second term with x=7 repeated once and z=14 (see FIG. 14 A or B) and followed by the third term with x=7 repeated once and z=14 (see FIG. 15 A or B). Alternatively, the agonist schedule may be x=7 repeated twice and z=7 to match the 4-week rhythm of the anti-CD38 antibody.

An example of an anti-CD19 antibody is Blinatumomab (bispecific for CD19 and CD3), for an anti-CD20 antibody are Ofatumumab and Obinutuzumab, an anti-CD30 antibody is Brentuximab, an anti-CD33 antibody is Gemtuzumab, for an anti-CD52 antibody is Alemtuzumab, an anti-CD79B antibody is Polatuzumab, for an anti-EGFR antibody is Cetuximab, an anti-HER2 antibody is Trastuzumab, an anti-VEGFR2 antibody is Ramucirumab, an anti-GD2 antibody is Dinutuximab, an anti-Nectin 4 antibody is Enfortumab and an anti-Trop-2 antibody is Sacituzumab.

Examples of aligned dosing schedules are the combination of SO-C101 with Ramucirumab, which is infused every 2 to 3 weeks depending on the indication. For a 3 week cycle of Ramucirumab, SO-C101 may be administered with x=7 repeated once and z=7. For two 2 week cycles of Ramucirumab, SO-C101 may be administered with x=7 repeated twice and z=7.

Pulsed Dosing

Another embodiment relates to an IL-2/IL-15Rβγ agonist for use in treating or managing cancer or infectious diseases, comprising administering the IL-2/1L-15Rβγ agonist according to the following administration regimen comprising (i) administration of the IL-2/1L-15Rβγ agonist to a human patient at a daily dose on a first number of consecutive days; and (ii) a second number of days without administration of the IL-2/IL-15Rβγ agonist, wherein the first number is 2, 3 or 4 days and the second number is 3, 4 or 5 days wherein the first number and second add up to 7 days.

This administration scheme can be described as a "pulsed" dosing—"pulsed" as the IL-2/1L-15Rβγagonist is administered e.g. at day 1 and day 2 of a week activating and expanding both NK and CD8⁺ T cells (a "pulse"), followed by no administration of the agonist for the rest the week. This pulsed dosing administration regimen is repeated at least once, preferably at least twice, more preferably at least 4 times, most preferably until disease progression. Preferably, the first number of days and the second number of days are 7 days in total (2+5, 3+4 or 4+3 days), such first number of days and second number of days being a cycle for the pulsed cyclic regime.

The embodiments described above for the pulsed cyclic dosing apply for the pulsed dosing as far as they do not relate to cyclic dosing. This particularly applies to embodiments relating to the dose of the IL-2/IL-15Rβγ agonist to be administered, the way of administration (e.g., s.c. or i.p.), the effects on NK cell activation and NK cell numbers, the conditions to be treated, the half-life of the IL-2/IL-15Rβγ agonist, the IL-2/IL-15Rβγ agonist and the co-administration of checkpoint inhibitors.

Preferably, the IL-2/IL-15Rβγ agonist is for use in the pulsed dosing regimen, wherein the daily dose is 0.1 µg/kg (0.0043 µM) to 50 µg/kg (2.15 µM), preferably 0.25 µg/kg (0.011 µM) to 25 µg/kg (1.1 µM), more preferably 0.6 µg/kg (0.026 µM) to 10 µg/kg (0.43 µM) and especially 2 µg/kg (0.087 µM) to 10 µg/kg (0.43 µM), preferably wherein the daily dose selected within the dose range of 0.1 µg/kg (0.0043 µM) to 50 µg/kg (2.15 µM) is not substantially increased during the administration regimen, preferably wherein the dose is maintained during the administration regimen. It is further preferred that the daily dose is 3 µg/kg (0.13 µM) to 20 µg/kg (0.87 µM), preferably 6 µg/kg (0.26 µM) to 12 µg/kg (0.52 µM).

In another embodiment, the pulsed dosing applies a daily dose, wherein the daily dose is a fixed dose independent of body weight of 7 µg to 3500 µg, preferably 17.5 µg to 1750 µg, more preferably 42 µg to 700 µg and especially 140 µg to 700 µg.

In another embodiment, the pulsed dosing applies daily doses, wherein the daily dose is increased during the administration regimen. Preferably, the daily dose is increased after each period of x days. In a further embodiment, the daily dose is increased by 20% to 100%, preferably by 30% to 50% after each period of x days.

In another embodiment, the daily dose is increased once after the first cycle. Preferably, the daily dose is increased by 20% to 100%, preferably by 30% to 50% after the first cycle.

In one embodiment of the pulsed dosing, the daily dose is administered in a single injection.

In an alternative embodiment of the pulsed dosing, the daily dose is split into 2 or 3 individual doses that are administered within one day, wherein the time interval between administration of the individual doses is at least about 4 h and preferably not more than 14 h. Preferably, the daily dose is split into 3 individual doses that are administered within one day, wherein the time interval between administration of the individual doses is about 5 to about 7 h, preferably about 6 h. Or, also preferred, the daily dose is split into 2 individual doses that are administered within one day, wherein the time interval between administration of the individual doses is about 6 h to about 10 h, preferably about 8 h.

In another embodiment, of the pulsed dosing, the IL-2/IL-15Rβγ agonist is administered subcutaneously (s.c.) or intraperitoneally (i.p.), preferably s.c.

Preferably, as further described above, administration of the IL-2/IL-15Rβγ agonist in step (a) results in (1) an increase of the % of Ki-67⁺ NK of total NK cells in comparison to no administration of the IL-2/IL-15Rβγ agonist, and wherein administration of the IL-2/IL-15Rβγ agonist in step (b) results in a Ki-67⁺ NK cell level that is at least 70% of the of the Ki-67⁺ NK cells of step (a), or (2) maintenance of NK cell numbers or preferably an increase of NK cell numbers to at least 110% as compared to no administration of IL-2/IL-15Rβγ agonist after at least one repetition of the first period, preferably after at least two repetitions of the first period, and/or (3) NK cell numbers of at least $1.1 \times 10^3$ NK cells/µl after at least one repetition of the first period, preferably after at least two repetitions of the first period.

It is further preferred for the pulsed dosing that the cyclic administration is repeated over at least 5 cycles, preferably 8 cycles, more preferably at least 15 cycles and even more preferably until disease progression.

In another embodiment for the pulsed dosing regimen the IL-2/IL-15Rβγ agonist has an in vivo half-life of 30 min to 24 h, preferably 1 h to 12 h, more preferably of 2 h to 6 h. In another embodiment the in vivo half-life is 30 min to 12 hours, more preferably 30 min to 6 hours, preferably as determined in cynomolgus monkeys.

In another embodiment for the pulsed dosing regimen, the IL-2/IL-15Rβγ agonist is an interleukin 15 (IL-15)/interleukin-15 receptor alpha (IL-15Rα) complex, preferably a fusion protein comprising the human IL-15Rα sushi domain or derivative thereof, a flexible linker and the human IL-15 or derivative thereof, preferably wherein the human IL-15Rα sushi domain comprises the sequence of SEQ ID NO: 6, and wherein the human IL-15 comprises the sequence of SEQ ID NO: 4, more preferably wherein the IL-15/IL-15Rα complex is SEQ ID NO: 9.

Further, IL-2/IL-15Rβγ agonist for use in the pulsed dosing may be administered in combination with a further therapeutic agent. Preferably, the further therapeutic agent and the IL-2/IL-15Rβγ agonist are administered on the same days and/or on different days. Further it is preferred that the administration of the further therapeutic agent occurs according to an administration regimen that is independent of the administration regimen of the IL-2/IL-15Rβγ agonist.

In one embodiment of the pulsed dosing regimen, the further therapeutic agent is selected from a checkpoint inhibitor or a therapeutic antibody.

Preferably, the checkpoint inhibitor is selected from an anti-PD-1 antibody, an anti-PD-L1 antibody, an anti-PD-L2 antibody, an anti-LAG-3 antibody, an anti-TIM-3 antibody, an anti-CTLA4 antibody or an anti-TIGIT antibody, preferably an anti-PD-L1 antibody or an anti-PD-1 antibody.

And preferably, the therapeutic antibody is selected from an anti-CD38 antibody, an anti-CD19 antibody, an anti-CD20 antibody, an anti-CD30 antibody, an anti-CD33 antibody, an anti-CD52 antibody, an anti-CD79B antibody, an anti-EGFR antibody, an anti-HER2 antibody, an anti-VEGFR2 antibody, an anti-GD2 antibody, an anti-Nectin 4 antibody and an anti-Trop-2 antibody, preferably an anti-CD38 antibody, preferably an anti-CD38 antibody Preferably, the IL-2/IL-15Rβγ agonist is for use, wherein an anti-CD38 antibody is administered once weekly for an initial 8 weeks, followed by 16 weeks of 2 treatments once per week and 2 weeks of treatment break, and thereafter once every 4 weeks until disease progression. For example the first number is 2 days and the second number is 5 days, and the anti-CD38 antibody is administered once per week on each $3^{rd}$ day of a week or on each $1^{st}$ day of a week; and wherein the treatment is continued for 8 weeks. Or, the first number is 2 days and the second number is 5 days, and the anti-CD38 antibody being administered for 16 weeks once per week on the $3^{rd}$ day of each $1^{st}$ week and $2^{nd}$ week of each 4-week cycle, or on the $1^{st}$ day of each $1^{st}$ week and $2^{nd}$ week of each 4-week cycle, and followed by the anti-CD38 antibody being administered until disease progression once per week on the 3' day of each $1^{st}$ week of each 4-week cycle, or on the $1^{st}$ day of each $1^{st}$ week of each 4-week cycle.

The anti-CD38 antibody is preferably daratumumab, MOR202, isatuximab, GEN1029, TAK-573 or TAK-079, more preferably the anti-CD38 antibody is daratumumab. Preferably daratumumab is administered via i.v. infusion at the dose recommended according to its label, preferably with the dose of 16 mg/kg.

Dense Pulsed Dosing

In another aspect of the invention an interleukin-2/interleukin-15 receptor βγ (IL-2/IL-15Rβγ) agonist is for use in treating or managing cancer or infectious diseases, comprising administering the IL-2/IL-15Rβγ agonist to a human patient using a dense pulsed administration regimen, wherein the dense administration regimen comprises ("dense pulsed"):

(a) a first period of x days during which the IL-2/IL-15Rβγ agonist is administered at a daily dose on y consecutive days at the beginning of the first period followed by x-y days without administration of the IL-2/IL-15Rβγ agonist, wherein x is 5, 6, 7, 8, 9, 10, 11, 12, 13, 14, 15, 16, 17, 18, 19, 20 or 21 days, preferably, 7 or 14 days, and y is 2, 3 or 4 days, preferably 2 or 3 days;

(b) repeating the first period at least once; and wherein the daily dose is split into 2 or 3 individual doses that are administered within one day, wherein the time interval between administration of the individual doses is at least about 4 h and preferably not more than 12 h.

Preferably, the administration regimen further comprises (c) a second period of z days without administration of the IL-2/IL-15Rβγ agonist ("dense pulsed cyclic"), wherein z is 5, 6, 7, 8, 9, 10, 11, 12, 13, 14, 15, 16, 17, 18, 19, 20, 21, 28, 35, 42, 49, 56, 63 or 70 days, preferably 7, 14, 21 or 56 days, more preferably 7 or 21 days.

It is expected that the same amount of the agonist—split into several doses and administered during the day—is more efficacious in stimulating NK cells and especially CD $8^+$ cells, the latter showing a lower sensitivity for the stimulation, than administered only in a single injection.

Such multiple dosing should be able to be integrated into the daily business of hospitals, doctor's practice or outpatient settings and therefore, 2 to 3 equal doses administered during business hours including shifts between 8 and 12 hours would still be conveniently manageable, with 8 or 10 h intervals being preferred as the maximum time difference between first and last dose. Accordingly, it is a preferred embodiment that the daily dose is split into 3 individual doses that are administered within one day, wherein the time interval between administration of the individual doses is about 5 to about 7 h, preferably about 6 hours. This means that a patient could be dosed e.g. at 7 am, 2 pm and 7 pm every day (with 6-hour intervals), or at 7 am, 1 pm and 6 pm (with 5 hour intervals). In another preferred embodiment, the daily dose is split into 2 individual doses that are administered within one day, wherein the time interval between administration of the individual doses is about 6 h to about 10 h, preferably 8 h. In the case of 2 doses, a patient could be dosed e.g. at 8 am and 4 pm (with an 8-hour interval). Given the daily routine of hospitals, the intervals between the administrations may vary within a day or from day to day. Surprisingly, in mice the same amount (about 40 μg/kg) of SO-C101 split into 3 doses (13 μg/kg) administered during the day lead to a drastic increase of $CD8^+$ T cell counts as well as $Ki67^+$ CD8 T cells as a measure for proliferating $CD8^+$ T cells, and even have the amount split into 3×7 μg/kg still showed much higher expansion and activation of $CD8^+$ T cells (see FIG. 19).

Accordingly, it is a preferred embodiment that the daily dose is split into 3 individual doses that are administered within one day, wherein the time interval between administration of the individual doses is about 5 to about 7 h, preferably about 6 hours. This means that a patient could be dosed e.g. at 7 am, 2 pm and 7 pm every day (with 6-hour intervals), or at 7 am, 1 pm and 6 pm (with 5 hour intervals). In another preferred embodiment, the daily dose is split into 2 individual doses that are administered within one day, wherein the time interval between administration of the individual doses is about 6 h to about 10 h, preferably 8 h. In the case of 2 doses, a patient could be dosed e.g. at 8 am and 4 pm (with an 8-hour interval). Given the daily routine of hospitals, the intervals between the administrations may vary within a day or from day to day.

The embodiments herein above for the pulsed cyclic dosing apply for the dense pulsed (and the dense pulsed cyclic dosing as a sub form of the dense pulsed dosing). This particularly applies to embodiments relating to the dose of the IL-2/IL-15Rβγ agonist to be administered, the way of administration (e.g., s.c. or i.p.), the effects on NK cell activation and NK cell numbers, the conditions to be treated, the half-life of the IL-2/IL-15Rβγ agonist, the IL-2/IL-15Rβγ agonist and the co-administration of checkpoint inhibitors.

Preferably, the IL-2/IL-15Rβγ agonist is for use in the dense pulsed or dense pulsed cyclic dosing regimen, wherein the daily dose is 0.1 μg/kg (0.0043 μM) to 50 μg/kg (2.15 μM), preferably 0.25 μg/kg (0.011 μM) to 25μg/kg (1.1 μM), more preferably 0.6 μg/kg (0.026 μM) to 10 μg/kg (0.43 μM) and especially 2 μg/kg (0.087 μM) to 10 μg/kg (0.43 μM), preferably wherein the daily dose selected within the dose range of 0.1 μg/kg (0.0043 μM) to 50 μg/kg (2.15 μM) is not substantially increased during the administration regimen, preferably wherein the dose is maintained during the administration regimen. It is further preferred that the daily dose is 3 μg/kg (0.13 μM) to 20 μg/kg (0.87 μM), preferably 6 μg/kg (0.26 μM) to 12 μg/kg (0.52 μM).

In another embodiment, the dense pulsed dosing applies a daily dose, wherein the daily dose is a fixed dose independent of body weight of 7 μg to 3500 μg, preferably 17.5 μg to 1750 μg, more preferably 42 μg to 700 μg and especially 140 μg to 700 μg.

In another embodiment, the dense pulsed dosing applies daily doses, wherein the daily dose is increased during the administration regimen. Preferably, the daily dose is increased after each period of x days. In a further embodiment, the daily dose is increased by 20% to 100%, preferably by 30% to 50% after each period of x days.

In another embodiment, the daily dose is increased once after the first cycle. Preferably, the daily dose is increased by 20% to 100%, preferably by 30% to 50% after the first cycle.

In another embodiment, of the dense pulsed dosing, the IL-2/IL-15Rβγ agonist is administered subcutaneously (s.c.) or intraperitoneally (i.p.), preferably s.c.

Preferably, as further described above, administration of the IL-2/IL-15Rβγ agonist in step (a) results in (1) an increase of the % of Ki-67$^+$ NK of total NK cells in comparison to no administration of the IL-2/IL-15Rβγ agonist, and wherein administration of the IL-2/IL-15Rβγ agonist in step (b) results in a Ki-67$^+$ NK cell level that is at least 70% of the of the Ki-67$^+$ NK cells of step (a), or (2) maintenance of NK cell numbers or preferably an increase of NK cell numbers to at least 110% as compared to no administration of IL-2/IL-15Rβγ agonist after at least one repetition of the first period, preferably after at least two repetitions of the first period, and/or (3) NK cell numbers of at least $1.1 \times 10^3$ NK cells/µl after at least one repetition of the first period, preferably after at least two repetitions of the first period.

It is further preferred for the dense pulsed cyclic dosing that the cyclic administration is repeated over at least 5 cycles, preferably 8 cycles, more preferably at least 15 cycles and even more preferably until disease progression.

In another embodiment for the dense pulsed dosing regimen the IL-2/IL-15Rβγ agonist has an in vivo half-life of 30 min to 24 h, preferably 1 h to 12 h, more preferably of 2 h to 6 h.

In another embodiment for the dense pulsed dosing regimen, the IL-2/IL-15Rβγ agonist is an interleukin 15 (IL-15)/interleukin-15 receptor alpha (IL-15Rα) complex, preferably a fusion protein comprising the human IL-15Rα sushi domain or derivative thereof, a flexible linker and the human IL-15 or derivative thereof, preferably wherein the human IL-15Rα sushi domain comprises the sequence of SEQ ID NO: 6, and wherein the human IL-15 comprises the sequence of SEQ ID NO: 4, more preferably wherein the IL-15/IL-15Rα complex is SEQ ID NO: 9.

Further, IL-2/IL-15Rβγ agonist for use in the dense pulsed dosing may be administered in combination with a further therapeutic agent. Preferably, the further therapeutic agent and the IL-2/IL-15Rβγ agonist are administered on the same days and/or on different days. Further it is preferred that the administration of the further therapeutic agent occurs according to an administration regimen that is independent of the administration regimen of the IL-2/IL-15Rβγ agonist.

In one embodiment of the dense pulsed dosing regimen, the further therapeutic agent is selected from a checkpoint inhibitor or a therapeutic antibody.

Preferably, the checkpoint inhibitor is selected from an anti-PD-1 antibody, an anti-PD-L1 antibody, an anti-PD-L2 antibody, an anti-LAG-3 antibody, an anti-TIM-3 antibody, an anti-CTLA4 antibody or an anti-TIGIT antibody, preferably an anti-PD-L1 antibody or an anti-PD-1 antibody.

And preferably, the therapeutic antibody is selected from an anti-CD38 antibody, an anti-CD19 antibody, an anti-CD20 antibody, an anti-CD30 antibody, an anti-CD33 antibody, an anti-CD52 antibody, an anti-CD79B antibody, an anti-EGFR antibody, an anti-HER2 antibody, an anti-VEGFR2 antibody, an anti-GD2 antibody, an anti-Nectin 4 antibody and an anti-Trop-2 antibody, preferably an anti-CD38 antibody, preferably an anti-CD38 antibody.

Another embodiment of the present invention is a kit of parts comprising several doses of the IL-2/IL-15Rβγ agonist of the invention, an instruction for administration of such IL-2/IL-15Rβγ agonist in the cyclic administration regimens according to any embodiment above and optionally an administration device for the IL-2/IL-15Rβγ agonist.

Another embodiment of the present invention is a kit of parts comprising several doses of the IL-2/IL-15Rβγ agonist of the invention, an instruction for administration of such IL-2/IL-15Rβγ agonist in the pulsed administration regimens according to any embodiment above and optionally an administration device for the IL-2/IL-15Rβγ agonist.

Another embodiment of the present invention is a kit of parts comprising several doses of the IL-2/IL-15Rβγ agonist of the invention, an instruction for administration of such IL-2/IL-15Rβγ agonist in the dense pulsed administration regimens according to any embodiment above and optionally an administration device for the IL-2/IL-15Rβγ agonist.

Another embodiment is the use of an IL-2/IL-15Rβγ agonist in the manufacture of a kit of parts for the treatment of cancer or an infectious disease, wherein the kit of parts comprises: several doses of the IL-2/IL-15Rβγ agonist of the invention, an instruction for administration of such IL-2/IL-15Rβγ agonist in the cyclic administration regimen according to any embodiment above and optionally an administration device for the IL-2/IL-15Rβγ agonist.

Another embodiment is the use of an IL-2/IL-15Rβγ agonist in the manufacture of a kit of parts for the treatment of cancer or an infectious disease, wherein the kit of parts comprises: several doses of the IL-2/IL-15Rβγ agonist of the invention, an instruction for administration of such IL-2/IL-15Rβγ agonist in the pulsed administration regimen according to any embodiment above and optionally an administration device for the IL-2/IL-15Rβγ agonist.

Another embodiment is the use of an IL-2/IL-15Rβγ agonist in the manufacture of a kit of parts for the treatment of cancer or an infectious disease, wherein the kit of parts comprises: several doses of the IL-2/IL-15Rβγ agonist of the invention, an instruction for administration of such IL-2/IL-15Rβγ agonist in the dense pulsed administration regimen according to any embodiment above and optionally an administration device for the IL-2/IL-15Rβγ agonist.

In a preferred embodiment the kit further comprises a checkpoint inhibitor and an instruction for use of the checkpoint inhibitor or the therapeutic antibody.

The invention also involves methods of treating cancer and infectious diseases involving the above described pulsed cyclic, pulsed and dense pulsed dosing regimens, as well as methods for stimulating NK cells and/or CD8$^+$ T cells involving the above described pulsed cyclic, pulsed and dense pulsed dosing regimens.

Dense Dosing

In another aspect of the invention an interleukin-2/interleukin-15 receptor βγ (IL-2/IL-15Rβγ) agonist is for use in treating or managing cancer or infectious diseases, comprising administering the IL-2/IL-15Rβγ agonist to a human patient using a dense administration regimen, wherein the dense administration regimen comprises administering a daily dose to a patient, wherein the daily dose is split into 2 or 3 individual doses that are administered within one day, wherein the time interval between administration of the individual doses is at least about 4 h and preferably not more than 12 h.

The time interval between administration of the individual doses may be as described for the above embodiments. The amount of the IL-2/IL-15Rβγ agonist may also be as described for the above embodiments.

FIGURES

FIG. 1: Pharmacodynamic study in Cynomolgus monkeys: In Phase 1, RLI-15/SO-C101 was administered i.v. as a 60-minute infusion or s.c. by injection in cynomolgus monkeys (groups as depicted in Table 2, 2 animals per group) daily on day 1 to day 4 at the indicated doses (details see dosing schedule (A), left part). Proliferating Ki67$^+$ NK cells (B) and proliferating Ki67$^+$CD8$^+$ T cells (C) were determined on day 5 by immunofluorescence analysis.

In Phase 2, after a two-week washout period, the cynomolgus monkeys were dosed i.v. as a 60-minute infusion or s.c. on study day D22 (1 Admin), on days D22, D23 (2 Admin), or D22-D25 (4 Admin) in groups as depicted in (A) and Table 3.

(D) Flow cytometry analyses were performed 5 days after the first administration on D26. The fraction of Ki67-positive cells was determined in the CD3$^-$CD8$^+$CD45$^+$ (NK cells) and CD3$^+$CD8$^+$CD45$^+$ (CD8$^+$ T cells) cell fractions. Data were collected from group 1 (1 Admin), groups 4, 5, 7 (pooled, 2 Admin) and group 6 (4 Admin).

(E) Increase in total lymphocyte, CD8$^+$ T cell and NK cell counts in cynomolgus following s.c. administration for the 2 Admin (group 5) during phase 1 (4 daily administration at D1, D2, D3 and D4, 10 μg/kg RLI s.c.) and phase 2 (2 consecutive daily administrations over three consecutive weeks, D22, D23, D29, D30, D36 and D37, shown by arrows, 15 μg/kg s.c.) with a rest period of two weeks in-between phase 1 and phase 2. Lymphocyte analysis was performed on day 5 of each dosing week. Lymphocyte counts were determined during hematology assessment, CD8$^+$ T cells and NK cells were determined by flow cytometry and multiplication of their relative proportion within CD45$^+$ cells with total white blood cell counts.

(F)-(I) Cell activation is shown by flow cytometry data (Ki67$^+$ NK cells and Ki67$^+$ CD8$^+$ T cells) (F, H, left panels) each in percent of all NK cells or CD8$^+$ T cells, respectively and cell activation by recalculation of NK and CD8$^+$ T cells obtained by flow cytometry analyses to hematology assessment of cell counts (G, I right panels) of animals 69 and 70 (Group 5)

(J)-(Q) Comparison of two administrations (L,M, P, Q) with four administration (J, K, N,O) each in week 1 and week 3 of Phase 2 (Groups 3 and 4) for NK cells (J, K, L, M) and CD8$^+$ T cells (N, O, P, Q).

FIG. 2: RLI-15/SO-C101 was administered s.c. at dose of 100 μg/kg on 4 consecutive days per week (D1-D4, D8-11, D15-D18 and D22-D25) by injection in cynomolgus monkeys (2 animals). Cell expansion measured by flow cytometry as cell counts (10$^3$/μl) of NK cells (triangles), CD8$^+$ T cells (circles, dotted line) and total lymphocytes (circles, solid line) are depicted over time (days).

Figure 3:
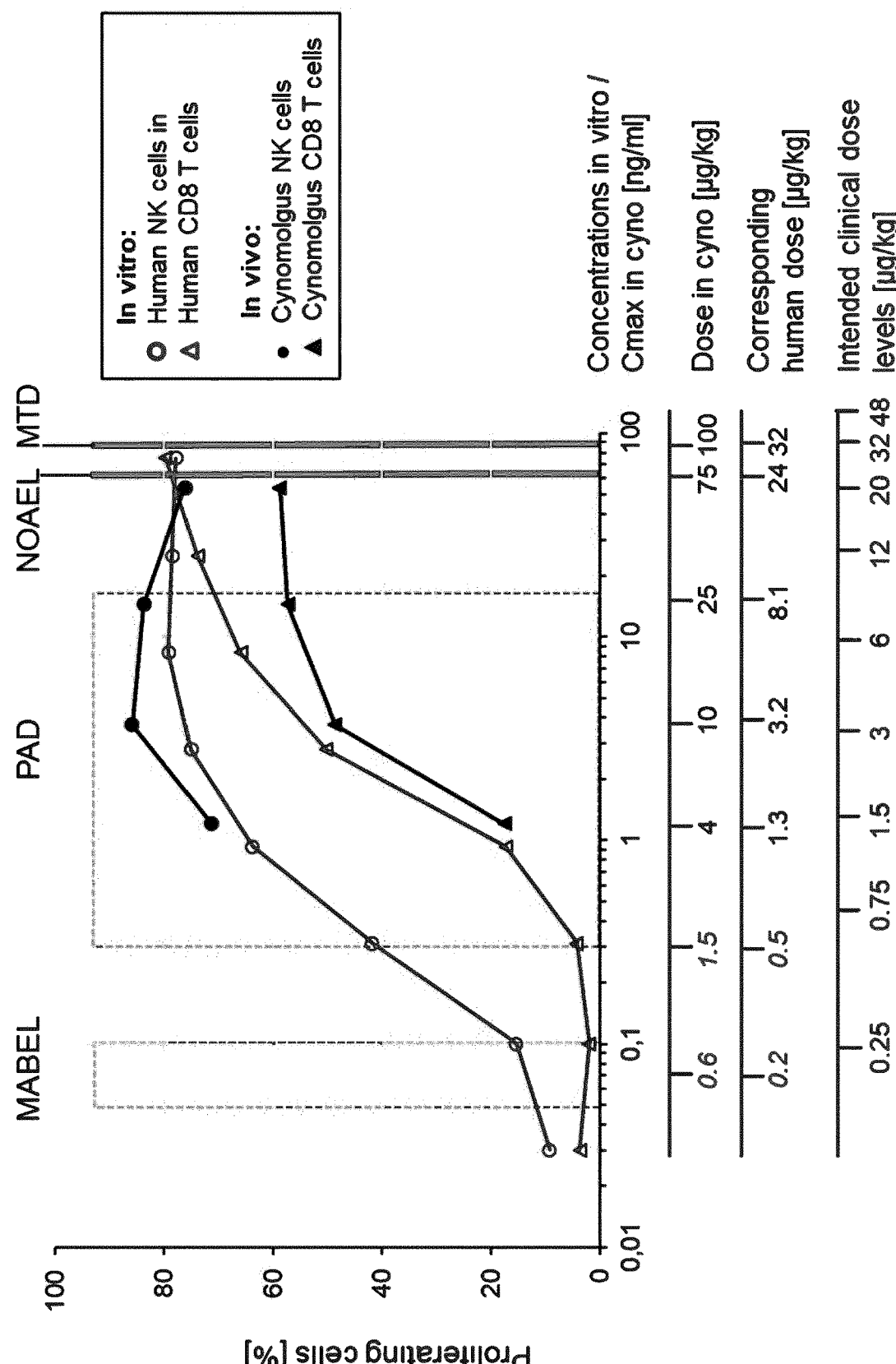

FIG. 3: Dose relationship of RLI-15/SO-C101 mediated NK and CD8$^+$ T cell activation for human/in vitro to cynomolgus/in vivo (including pharmacodynamics and pharmacokinetics) and the $C_{max}$ observed in vivo. In vivo doses are shown according to the $C_{max}$ achieved. Data obtained from flow cytometry on NK and CD8$^+$ T cell proliferation (CFSE stained proliferating cells) induced by RLI-15 in vitro stimulation of human PBMC (7 days) and in vivo cynomolgus monkey treatment with RLI-15 (4 consecutive days s.c., FACS at day 5) were correlated. Similarly, concentrations used in vitro and obtained from PK studies in cynomolgus monkeys are incorporated into X axis. Human equivalent doses were calculated by allometric scaling using 3.1 as factor. MABEL: Minimal Anticipated Effect Level, PAD: Pharmacologic Active Dose Range, NOAEL: No Adverse Effect Level, MTD: Maximum Tolerated Dose.

Figure 4:
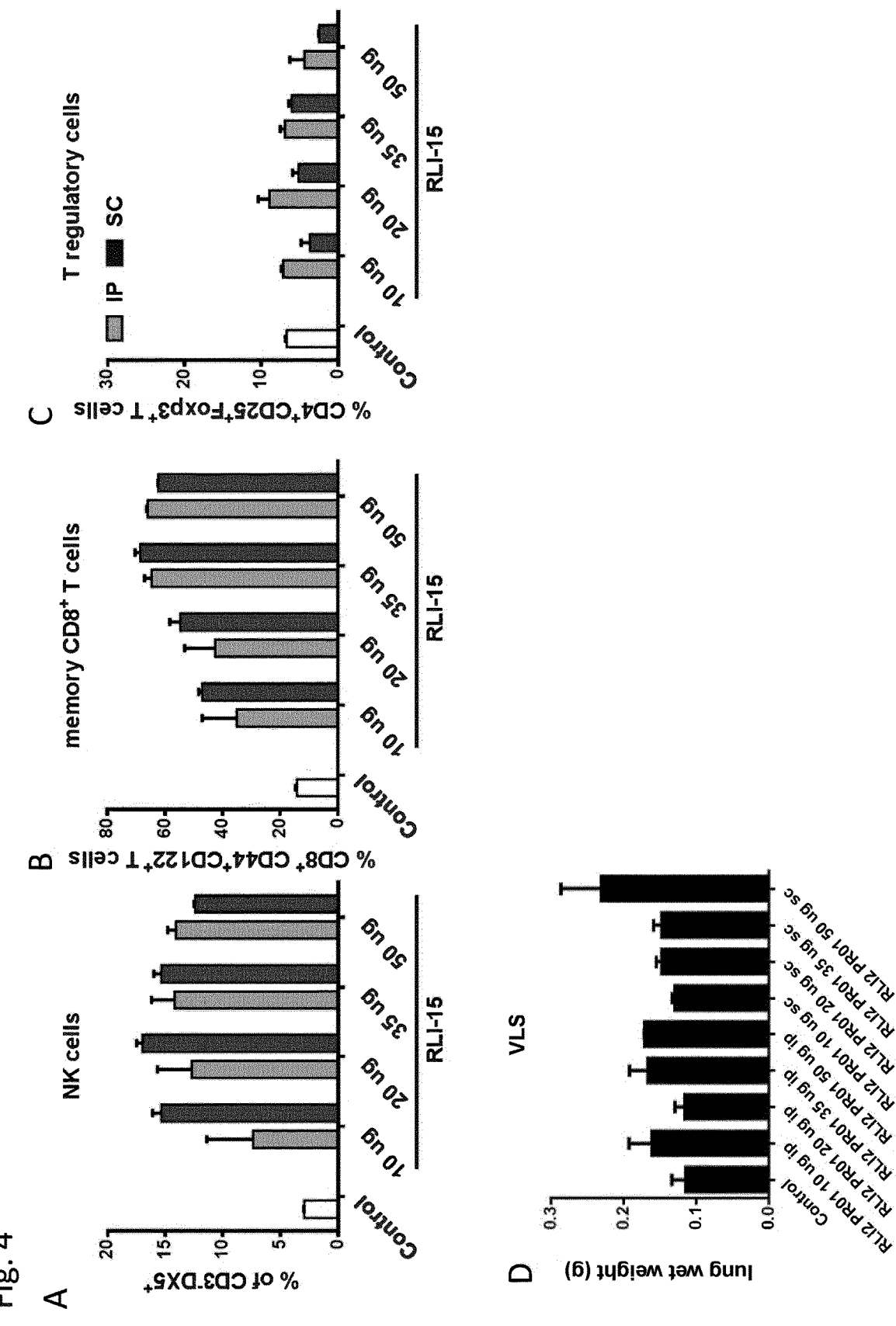

FIG. 4: Concentration dependent RLI-15-induced expansion of NK cells, memory CD8$^+$ T cells and T regulatory cells. The pharmacodynamics of RLI-15/SO-C101 in vivo in mouse was tested using various RLI-15 concentrations (10, 20, 35 and 50 μg/dose) injected s.c. or i.p. once daily for 4 consecutive days (2 animals per group). The relative expansion of (A) NK cells (CD3$^-$, CD49b/DX5$^+$), (B) memory CD8$^+$ T cells (CD8$^+$ CD44$^+$ CD122$^+$ T cells) and (C) T regulatory cells (CD4$^+$CD25$^+$FoxP3$^+$ T cells) was determined by flow cytometry from splenocytes on day 5; (control—non-treated mice). Lung wet weight was determined as a measure for Vascular Leak Syndrome (VLS) evaluated at day 5 (D).

Figure 5:
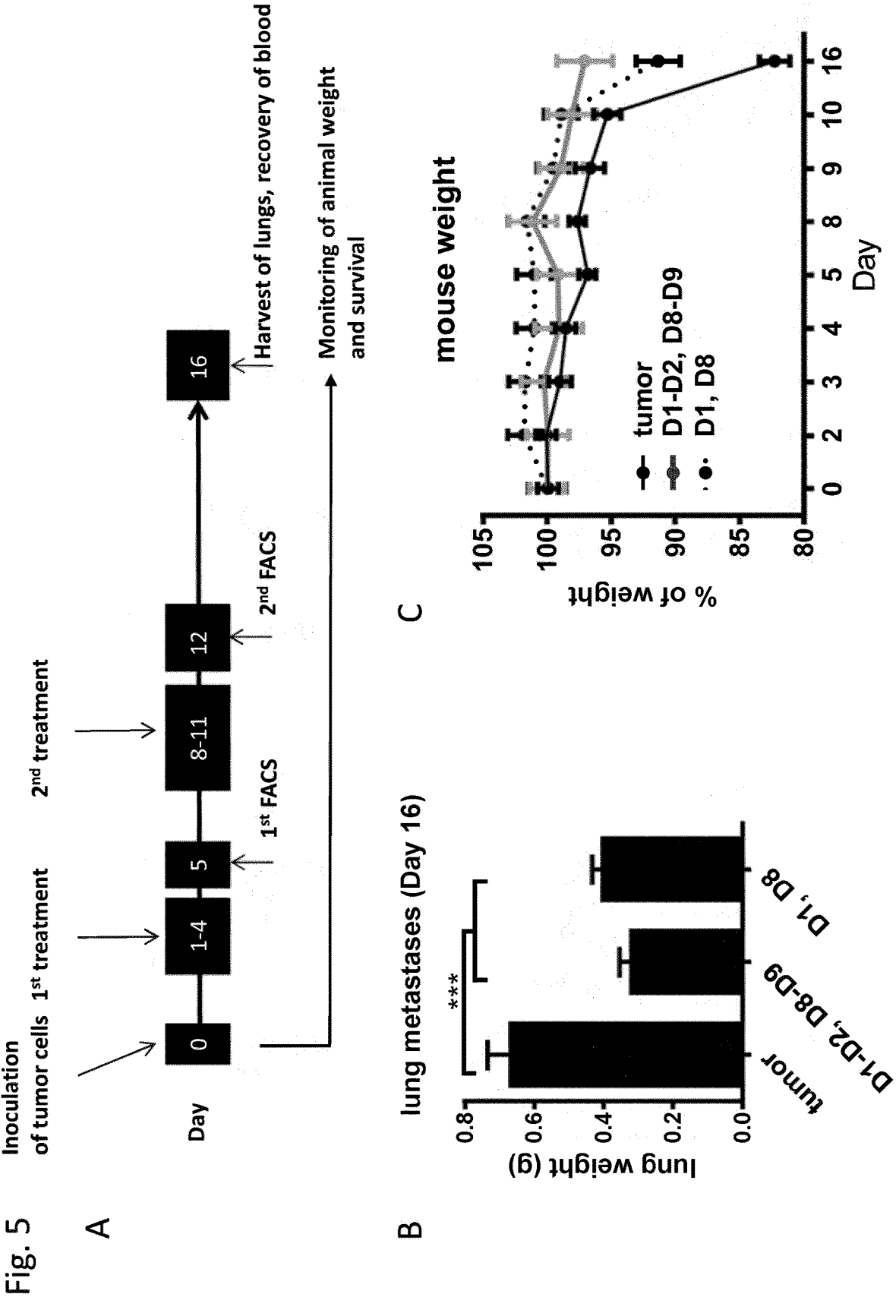
Figure 5:
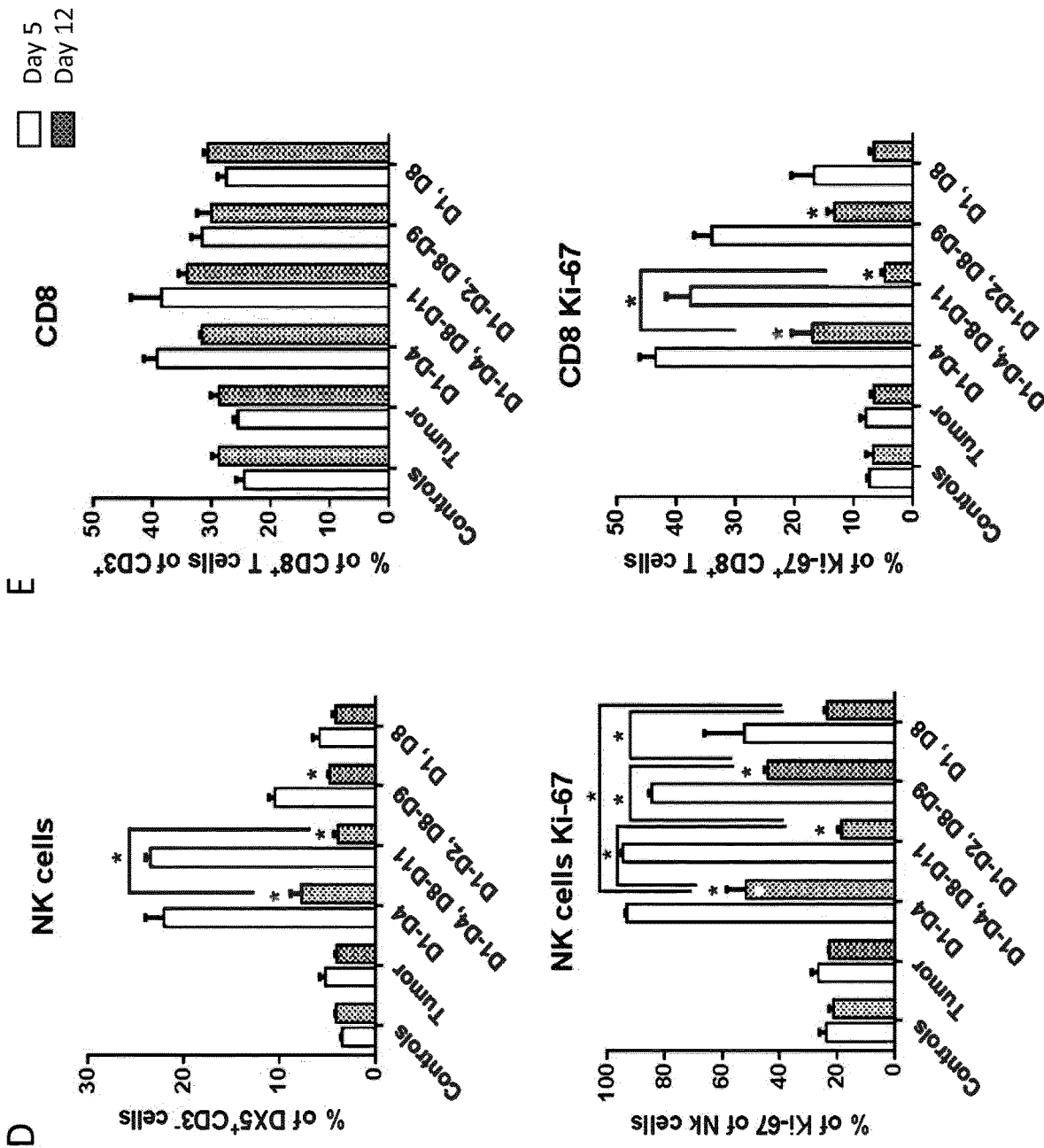

FIG. 5: The evaluation of an RUT-IS-induced anti-metastatic effect in RENCA mouse tumor model after i.p. administration. (A) The experimental scheme. RLI-15/SO-C101 was administered according to provided schedules once daily i.p. after Renca tumor cells had been injected i.v. on day 0. Spleens for FACS analysis of immune cells were taken at days 5 and day 12 for pharmacodynamics. Animal weight and survival was monitored until day 16. On day 16 mice were sacrificed and lungs were taken for the analysis of the metastatic burden. (B) The lung weight (as a surrogate for a metastatic burden) in g was evaluated on day 16 for the given treatment groups. (C) The evaluation of the weight of the mice during the course of RLI-15 treatment in RENCA tumor model at selected days. Data were normalized to 100% of average weight in each group at Day 0. Solid black line with lowest endpoint: tumor; dotted black line with second lowest endpoint: D1+D8; grey line with third-lowest endpoint running most of time a bit above the solid black line: D1-D2+D8-D9.

On day 5 and day 12 after the initiation of the RLI-15 treatment splenocytes were analyzed for the relative expansion of NK cells and Ki-67$^+$ NK cells (dividing NK cells) (D) and CD8$^+$ T cells of CD3$^+$ cells and Ki-67$^+$ CD8$^+$ T cells of CD8$^+$ cells (dividing CD8$^+$ T cells) (E); Controls=naïve—tumor-free, untreated; Tumor=tumor bearing mice, untreated; other groups: tumor bearing mice treated with once daily doses of RLI-15 at indicated days.

Figure 6:
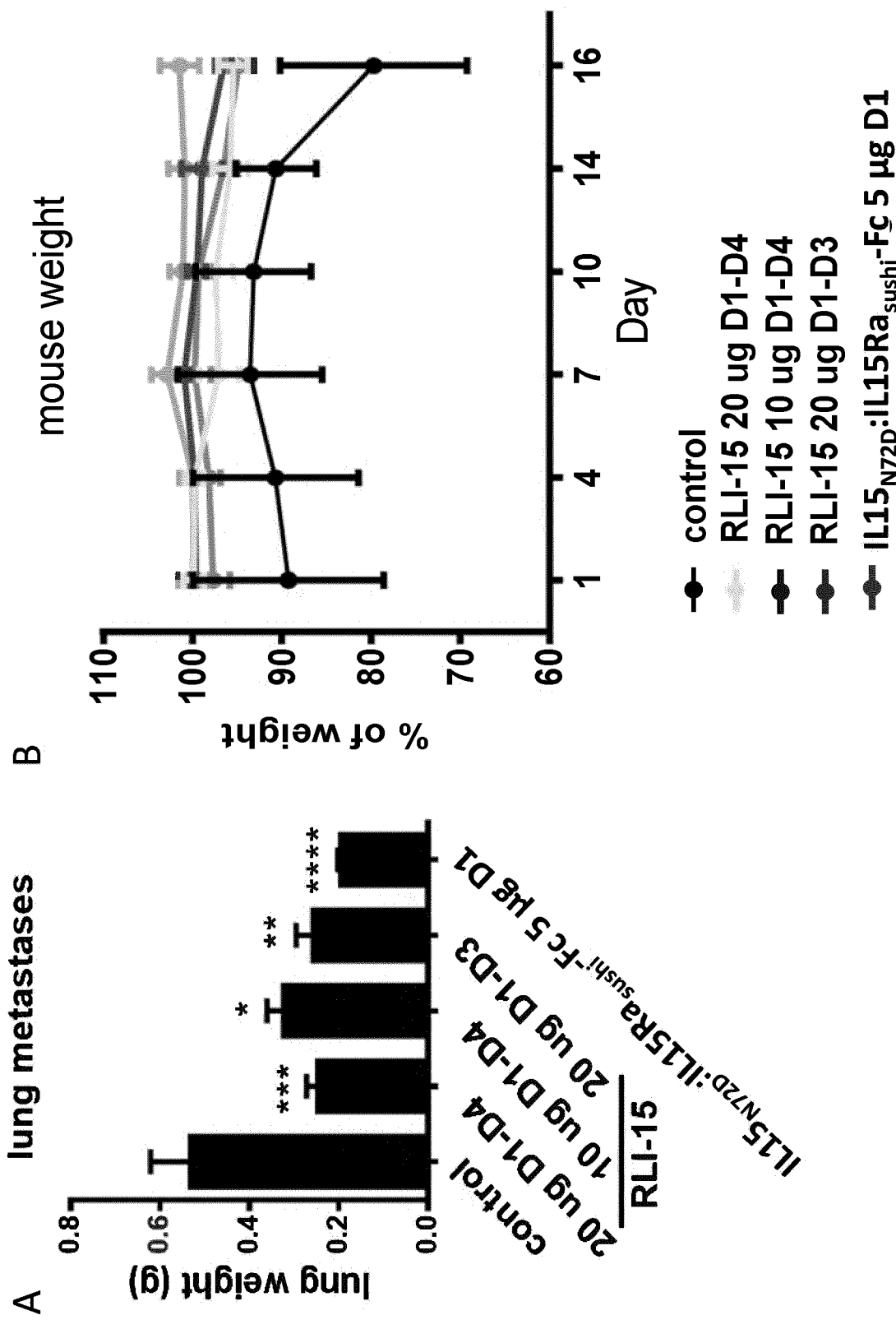

FIG. 6: The evaluation of an RLI-15-induced anti-metastatic effect in RENCA mouse tumor model after s.c. administration in comparison to IL15$_{N72D}$:IL15Ra$_{sushi}$-Fc. 10 μg or 20 μg of RLI-15/SO-C101 or 5 μg of IL15$_{N72D}$:IL15Ra$_{sushi}$-Fc was administered according to provided schedules once daily s.c. after Renca tumor cells had been injected i. v. on day 0. Animal weight and survival was monitored until day 16. On day 16 mice were sacrificed and lungs harvested for further analysis. (A) The lung weight (as a surrogate for a metastatic burden) in g was evaluated on day 16 for the given treatment groups. (B) The evaluation of the weight of the mice during the course of the treatment in RENCA tumor model at selected days. Data were normalized to 100% of average weight in each group at Day 0. Black line with lowest endpoint: tumor; red line with second lowest endpoint and second lowest starting point: RLI-15 20 μg at D1-D3; blue line with second highest end point: RLI-15 10 μg at D1-D4; green line with second lowest end point and second lowest interim points: RLI-15 20 μg at D1-D4; orange line with highest endpoint: IL15$_{N72D}$:IL15Ra$_{sushi}$-Fc 5 μg at D1.

Figure 7:
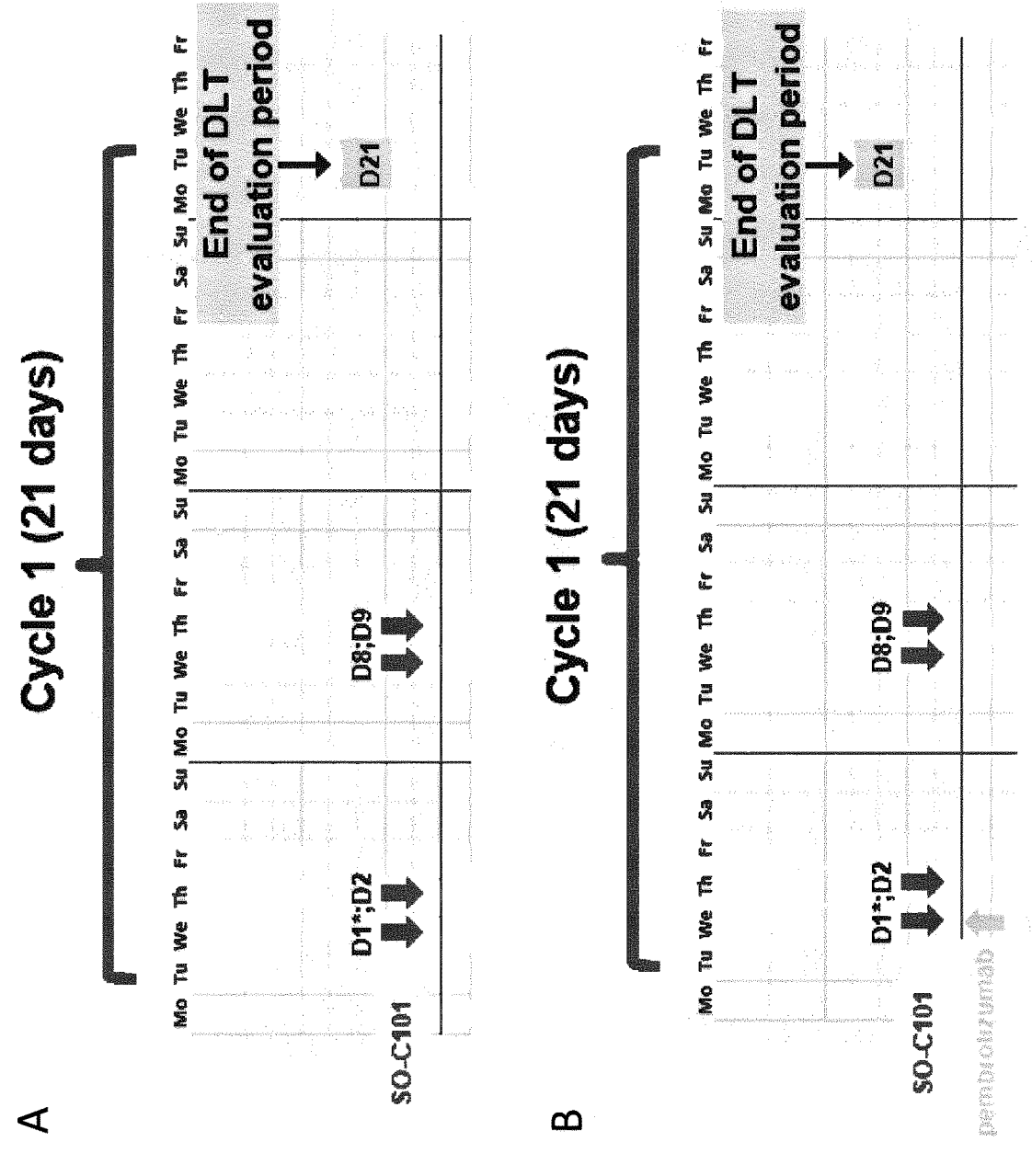

FIG. 7: Dosing schedule of first-in-human clinical trial. *±1 day; DLT dose-limiting toxicity;

(A) Part A: SO-C101 dosing schedule (B) Part B: SO-C101 in combination with pembrolizumab dosing schedule.

Figure 8:
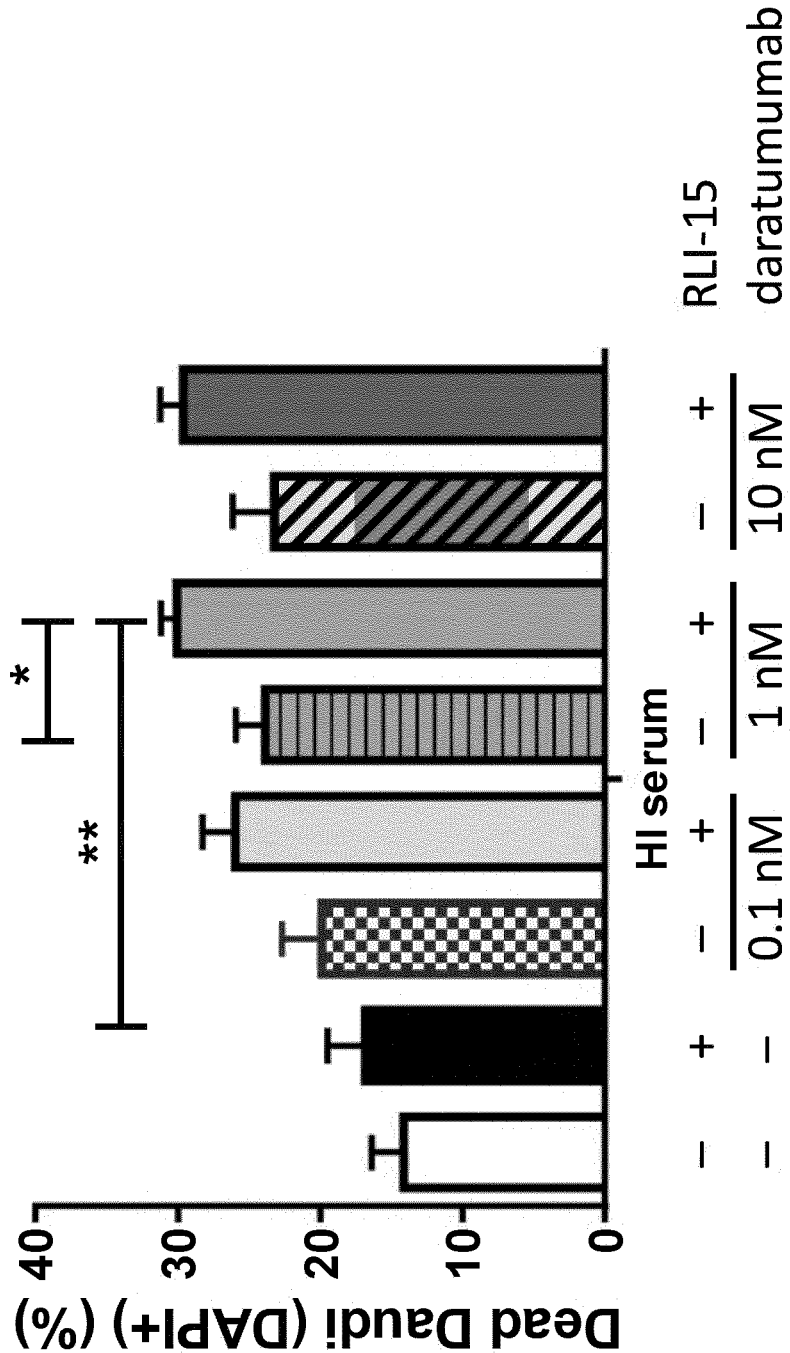

FIG. 8: Tumor cell killing in vitro by concomitant combination of RLI-15 and daratumumab. Human PBMC of 5 healthy donors were co-cultivated with Daudi tumor cells in the absence (−) or presence (+) of RLI-15/SO-C101 (RLI 1 nM), and/or increasing concentrations of daratumumab (0, 0.1 nM, 1 nM or 10 nM DAR) for 20 h at 37° C. The percentage of dead Daudi tumor cells are shown as measured by DAPI$^+$ staining by flow cytometry. The results were considered statistically significant if $p<0.05$ (*), $p<0.01$ (**).

Figure 9:
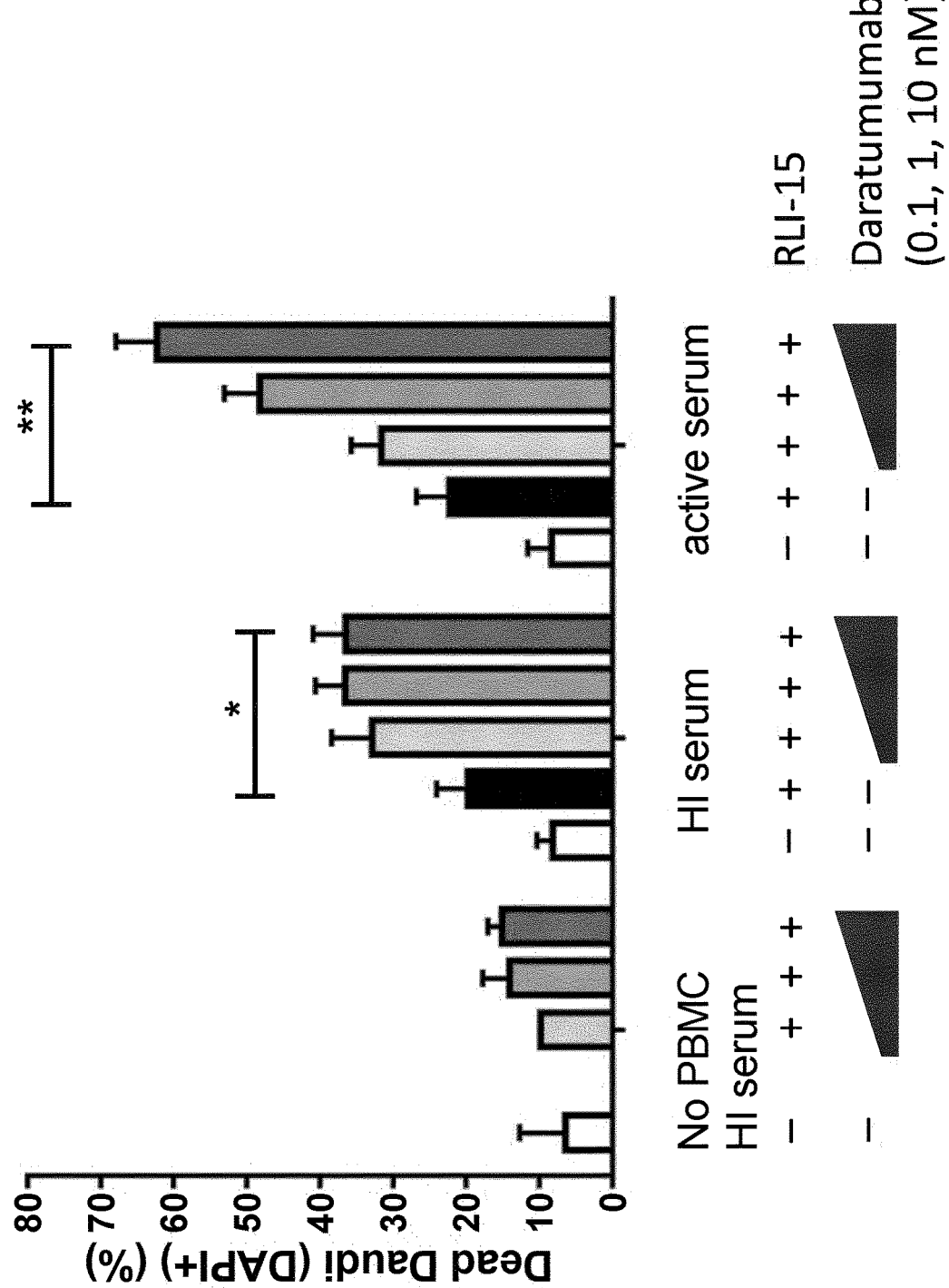

FIG. 9: Tumor cell killing in vitro by sequential combination of RLI-15 and daratumumab. Human PBMC of 6 healthy donors were incubated with or without RLI-15/SO-C101 (1 nM) for 48 h in vitro at 37° C. in either heat inactivated (HI) or active serum. Subsequently the stimulated hPBMC were co-cultivated with Daudi tumor cells in the absence (−) or presence (+) of the increasing amounts of daratumumab (0, 0.1 nM, 1 nM or 10 nM DAR) for 4 h at 37° C. The percentage of dead Daudi tumor cells are shown measured by DAPI$^+$ staining by flow cytometry. The results were considered statistically significant if $p<0.05$ (*), $p<0.01$ (**).

FIG. 10: Anti-tumor efficacy in vivo as shown by a concomitant combination of RLI-15 and daratumumab. CB17 SCID Mice were inoculated s.c. with $1\times10^7$ RPMI8226 myeloma cells. Treatment started with either saline (10 µl/g. s.c. at days 0, 1, 2 and 3), RLI-15/SO-C101 (1 mg/kg s.c. at days 0, 1, 2 and 3), daratumumab (20 mg/kg i.p. at day 4), or RLI-15/SO-C101 and daratumumab at the above stated concentrations and days.

(A) Tumor volume in mm$^3$ in dependence of time in days starting at day 0, when s.c. administration with saline or RLI-15 started (day 0=day of randomization into groups where the tumor volume was ~100 mm$^3$). Saline control group (black circles on solid line), RLI-15/SO-C101 treatment group (black circles on dotted line), daratumumab treatment group (grey circles on dotted line) and RLI-15+daratumumab combination group (grey circles on solid line)

(B) Mice with rejected tumors in % in dependence of time in days starting at day 0, when s.c. administration of saline or RLI-15 started. Saline control group (black solid line—not visible as on x-axis), RLI-15 treatment group (black dotted line), daratumumab treatment group (grey dotted line—not visible as on x-axis) and RLI-15+daratumumab combination group (grey solid line).

FIG. 11: Anti-tumor efficacy in vivo as shown by a sequential combination of RLI-15 and daratumumab. CB17 SCID Mice were inoculated s.c. with $1\times10^7$ RPMI8226 myeloma cells. Treatment started with either saline (10 µl/g. s.c. at days 0, 1, 2 and 3), RLI-15/SO-C101 (1 mg/kg s.c. at days 7, 8, 9 and 10), daratumumab (20 mg/kg i.p. at day 0), or RLI-15/SO-C101 and daratumumab at the above stated concentrations and days.

(A) Tumor volume in mm$^3$ in dependence of time in days starting at day 0, when s.c. administration of saline or i.p. administration of daratumumab started (day 0=day of randomization into groups where the tumor volume was ~100 mm$^3$). Saline control group (black circles on solid line), RLI-15 treatment group (black circles on dotted line), daratumumab treatment group (grey open circles on dotted line) and RLI-15+daratumumab combination group (grey circles on solid line)

(B) Mice with rejected tumors in % in dependence of time in days starting at day 0, when s.c. administration of saline or daratumumab started. Saline control group (black solid line—not visible as on x-axis), RLI-15 treatment group (black dotted line—not visible as on x-axis), daratumumab treatment group (grey dotted line) and RLI-15+daratumumab combination group (grey solid line).

Figure 12:
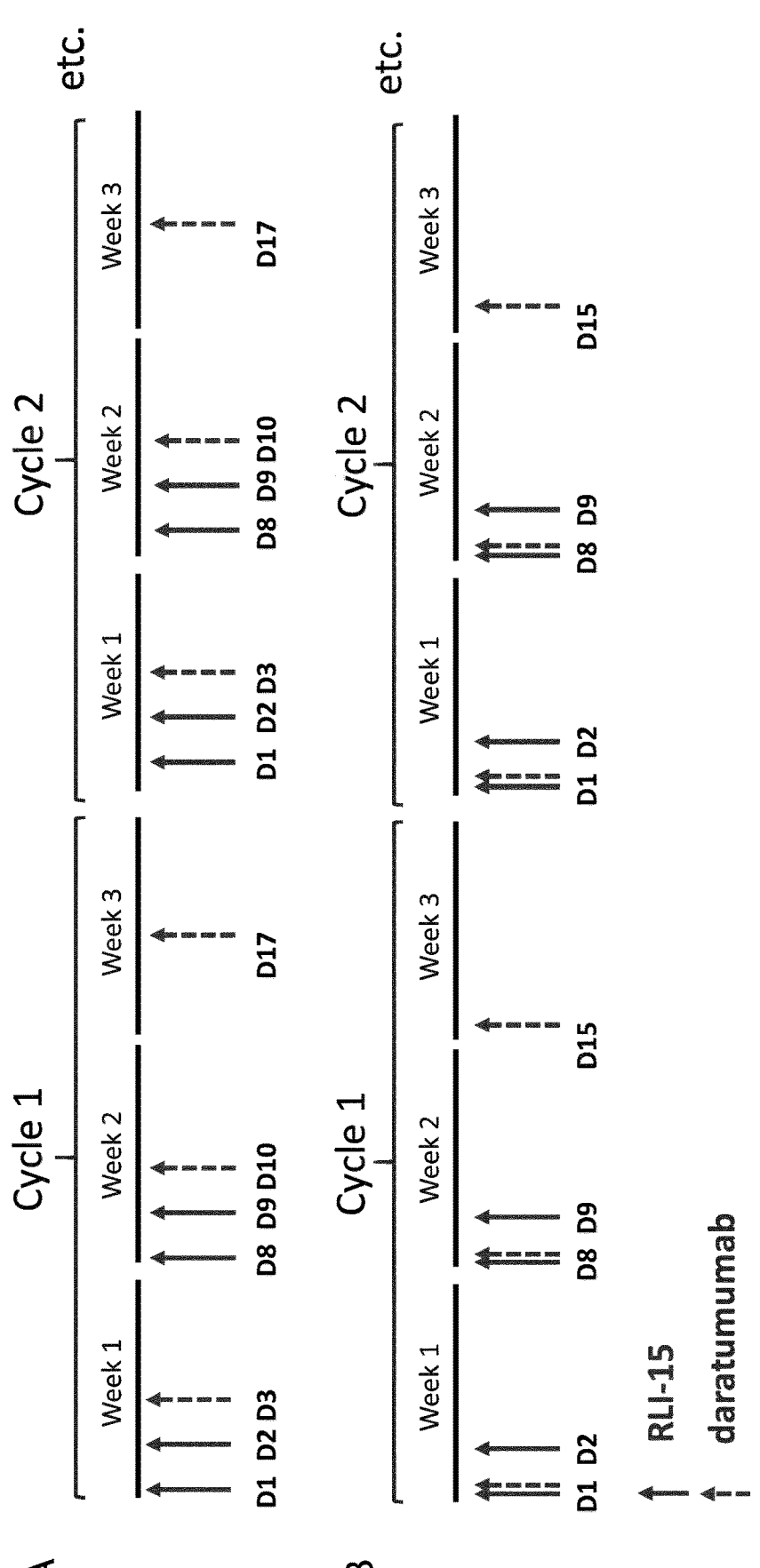

FIG. 12: Dosing schedule of clinical trial for RLI-15/SO-C101 in combination with daratumumab; RLI-15—s.c. at dose determined in first-in-human clinical trial (solid arrow for day of administration); daratumumab—16 mg/kg i.v. infusion once weekly for 8 weeks (total of 8 doses, dotted arrow for day of administration):

(A) combination schedule with RLI-15 administered at D1+D2 and D8+D9 and daratumumab administered at D3, D10 and D17 of a 3-week cycle.

(B) combination schedule with RLI-15 administered at D1+D2 and D8+D9 and daratumumab administered at D1, D8 and D15 of a 3-week cycle.

Figure 13:
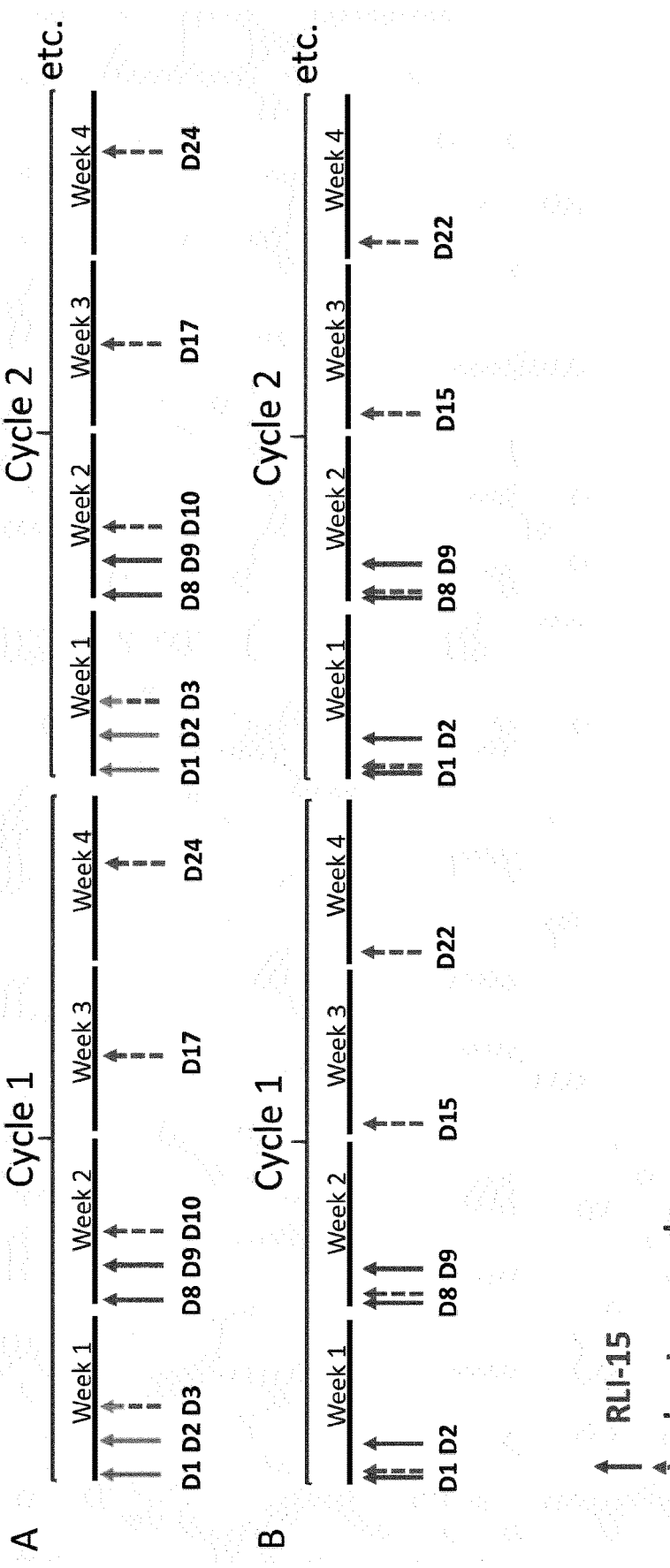

FIG. 13: Dosing schedule of clinical trial for RLI-15/SO-C101 in combination with daratumumab; RLI-15—s.c. at dose determined in first-in-human clinical trial (solid arrow for day of administration); daratumumab—16 mg/kg i.v. infusion once weekly for 8 weeks (total of 8 doses, dotted arrow for day of administration):

(A) combination schedule with RLI-15 administered at D1+D2 and D8+D9 and daratumumab administered at D3, D10, D17 and D24 of a 4-week cycle.

(B) combination schedule with RLI-15 administered at D1+D2 and D8+D9 and daratumumab administered at D1, D8, D15 and D22 of a 4-week cycle.

Figure 14:
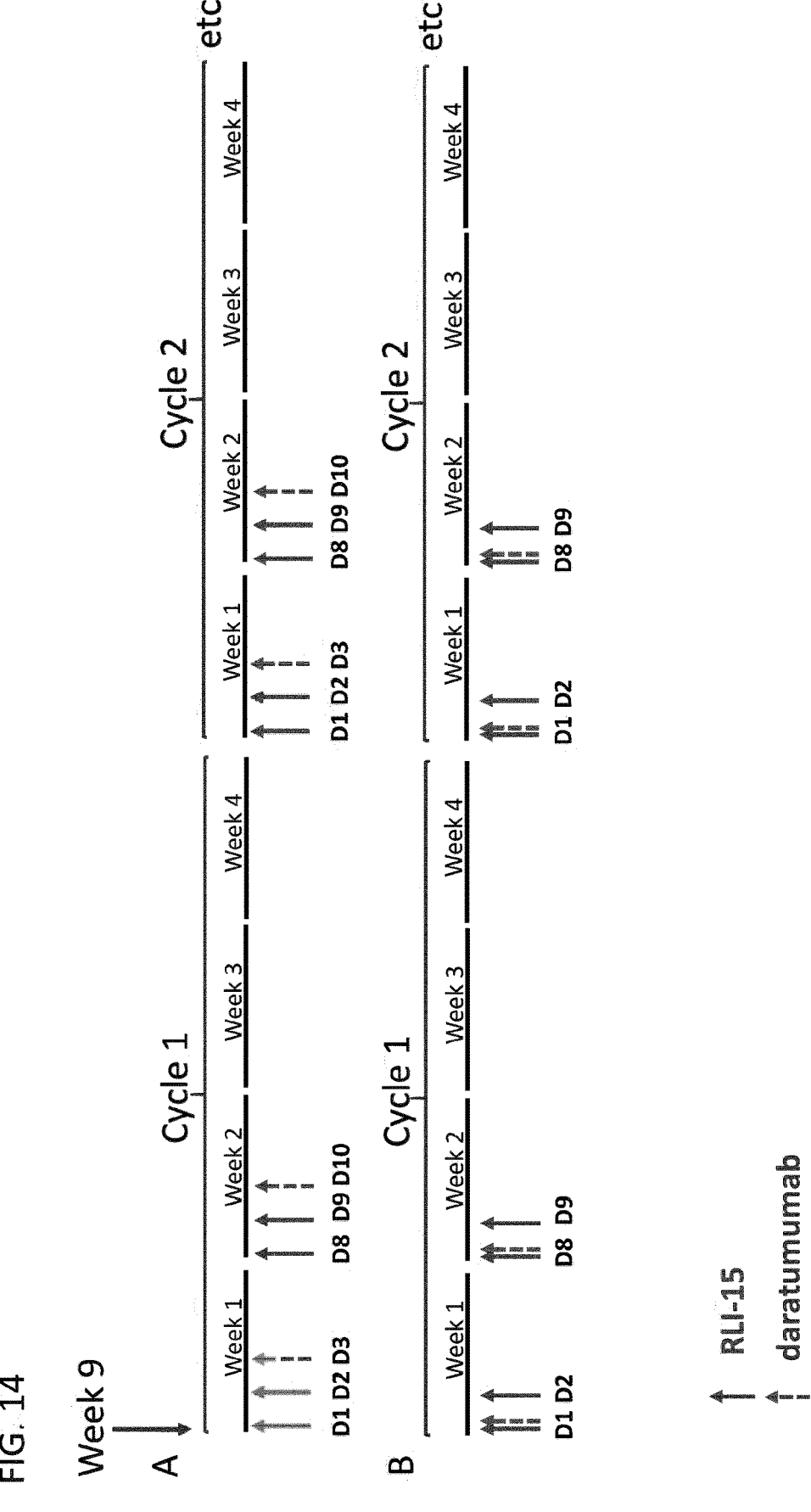

FIG. 14: Dosing schedule of clinical trial for RLI-15/SO-C101 in combination with daratumumab for weeks 9 to 24; RLI-15—s.c. at dose determined in first-in-human clinical trial (solid arrow for day of administration); daratumumab—16 mg/kg i. v. infusion twice in 4 weeks (total of 8 doses starting at week 9 of overall treatment, dotted arrow for day of administration):

(A) combination schedule with RLI-15 administered at D1+D2 and D8+D9 and daratumumab administered at D3 and D10 of a 4-week cycle.

(B) combination schedule with RLI-15 administered at D1+D2 and D8+D9 and daratumumab administered at D1 and D8 of a 4-week cycle.

FIG. 15: Dosing schedule of clinical trial for RLI-15/SO-C101 in combination with daratumumab for weeks 25 onwards until disease progression; RLI-15—s.c. at dose determined in first-in-human clinical trial (solid arrow for day of administration); daratumumab—16 mg/kg i.v. infusion once in 4 weeks (starting at week 25 of overall treatment, dotted arrow for day of administration):

(A) combination schedule with RLI-15 administered at D1+D2 and D8+D9 and daratumumab administered at D3 of a 4-week cycle.

(B) combination schedule with RLI-15 administered at D1+D2 and D8+D9 and daratumumab administered at D1 of a 4-week cycle.

Figure 16:
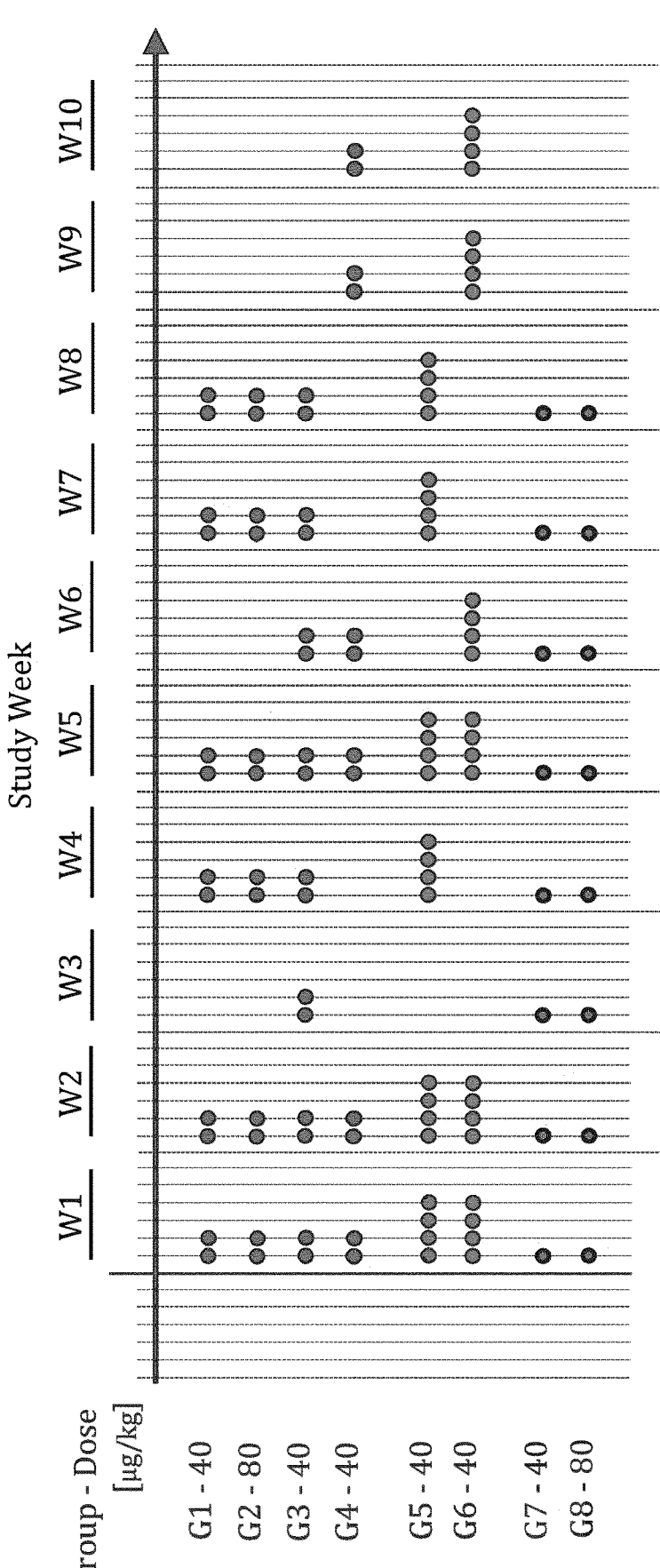

FIG. 16: Pharmacodynamic study of RLI-15/SO-C101 in Cynomolgus monkeys: Dosing schedules of groups G1 to G8 as administered in study weeks W1 to W10. Each dot stands for a single administration of a daily dose of 40 to 80 µg/kg of RLI-15/SO-C101 as indicated.

Figure 17B:
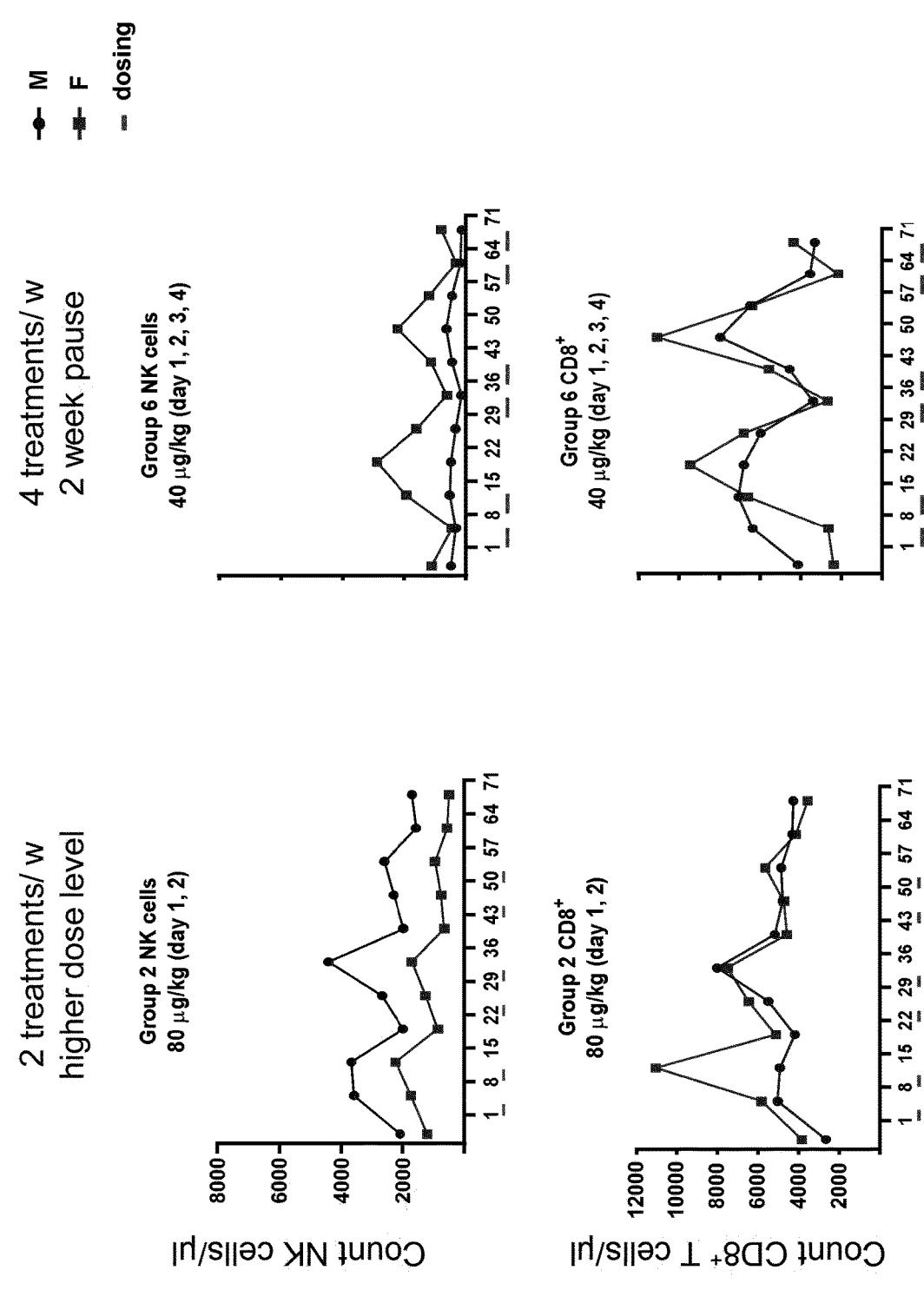
Figure 17C:
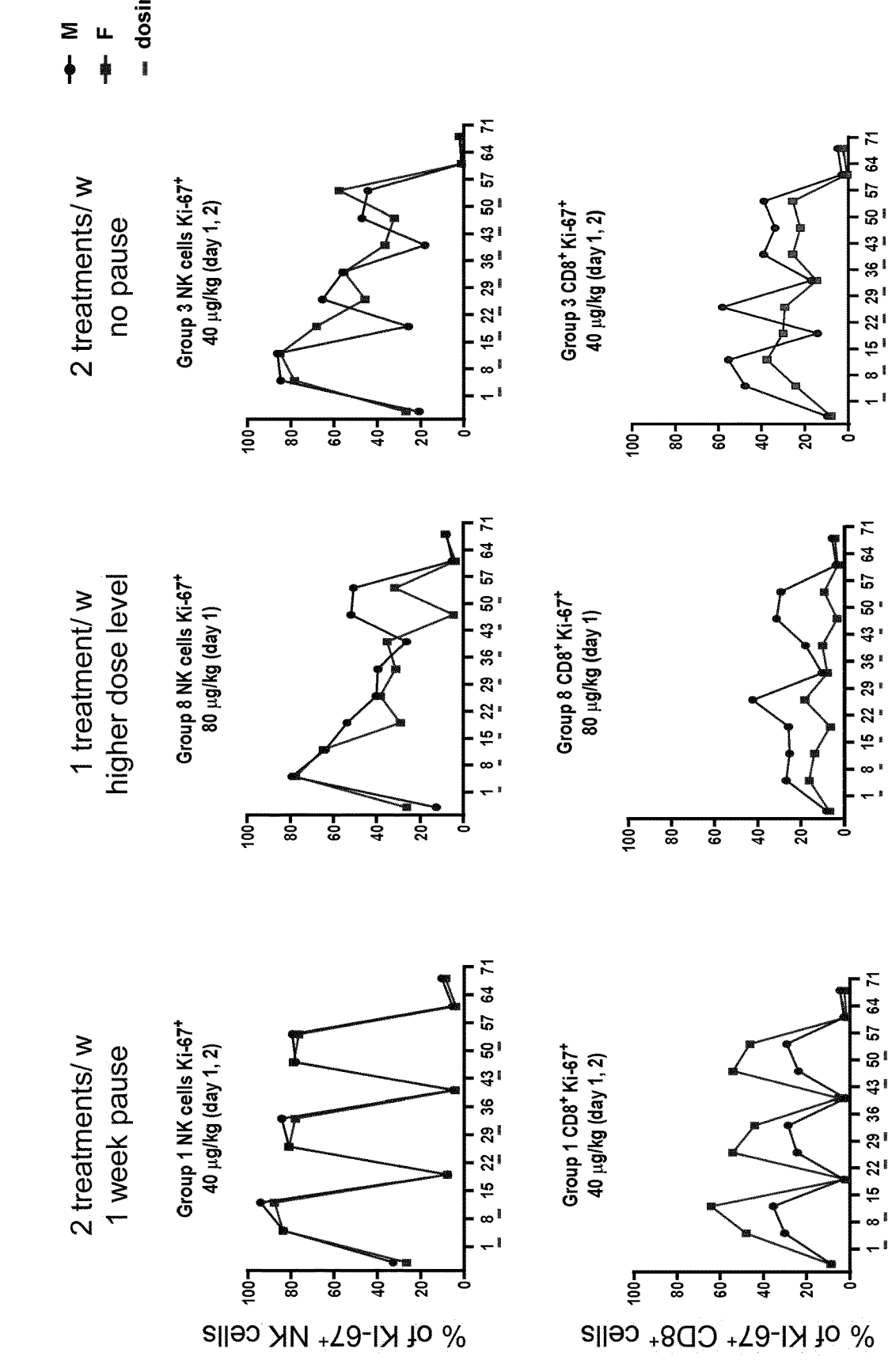

FIG. 17: a) and b) Time courses in days of NK cell counts and CD8$^+$ T cell counts in cells/µl of provided treatment groups 1, 8, 3, 2 and 6 for the male (filled circle) and female (filled square) are shown; days of dosing are underlined. c) and d) Time courses in days of percent Ki67+ NK cells and Ki67+ CD8+ T cells of provided treatment groups 1, 8, 3, 2 and 6 for the male (filled circle) and female (filled square) are shown; days of dosing are underlined.

Figure 18:
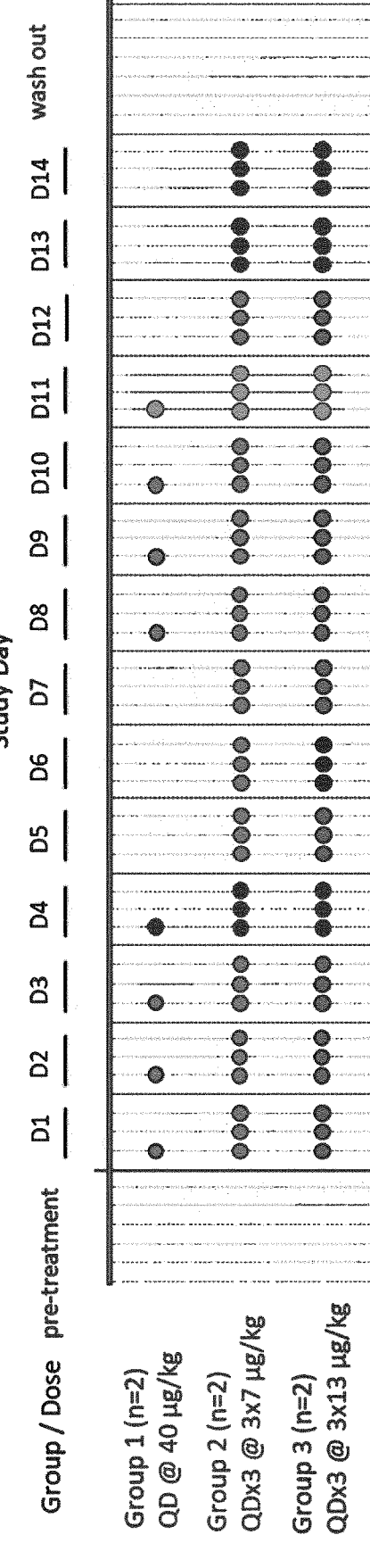

FIG. 18: Pharmacodynamic study of RLI-15/SO-C101 in Cynomolgus monkeys for the investigation of sustained exposure through 3 dosings per day: Dosing schedules of groups Group 1, Group 2 and Group 3 as administered during study days D1 to D14. Each dot stands for a single administration of a dose of 7 to 40 µg/kg of RLI-15/SO-C101 as indicated.

Figure 19:
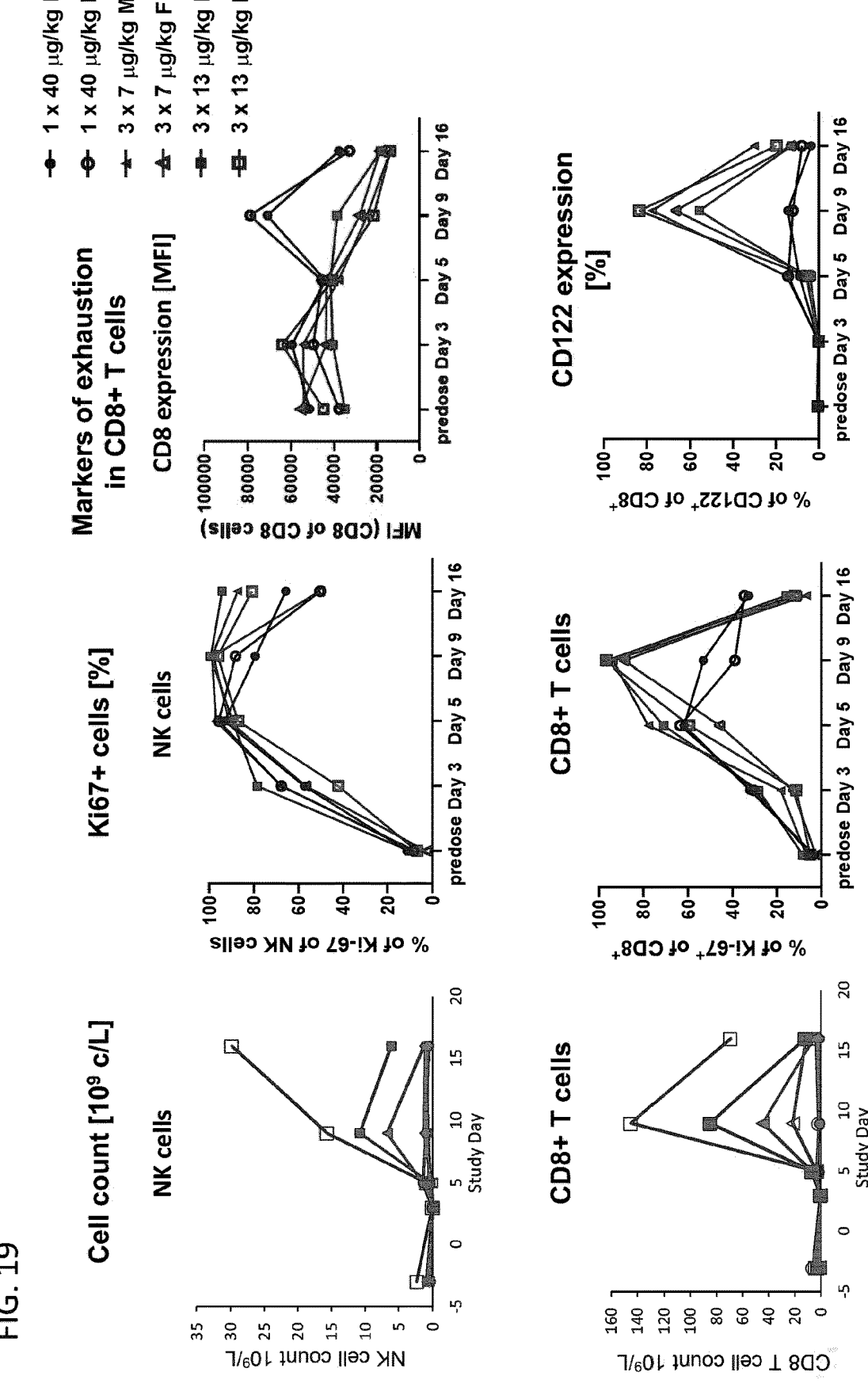

FIG. 19: Time courses in days of NK cell counts and CD8+ T cell counts in 10^9 cells/l (left panels), Ki67+ NK cells and CD8+ T cells (middle panels), CD8 expression by CD8+ T cells as Mean Fluorescent Intensity (upper right panel) and percentage of CD122+ cells of CD8+ cells (lower right panel) for the treatment Group 1 (circles, 1×40 µg/kg), Group 2 (triangles, 3×7 µg/kg) and Group 3 (squares, 3×13 µg/kg), whereas the filled circle/triangle/square shows the male animal and the open circle/triangle/square shows the female animal.

Figure 20:
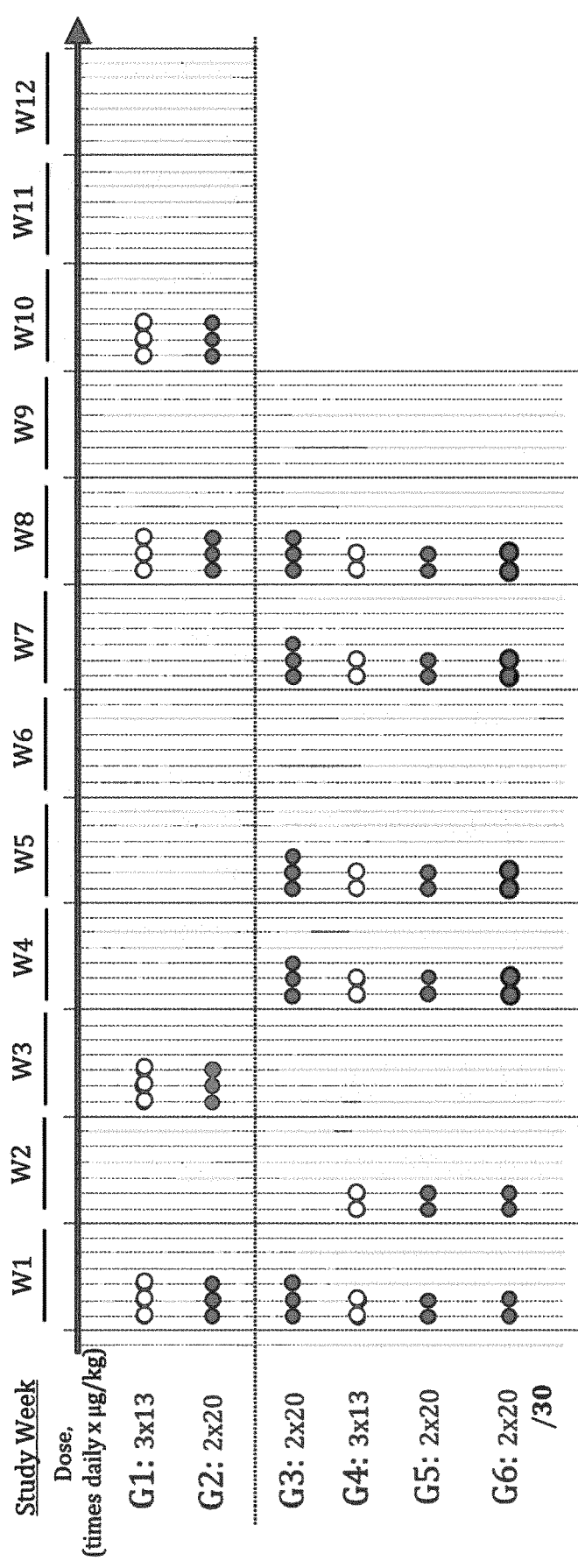

FIG. 20: Pharmacodynamic study of RLI-15/SO-C101 in Cynomolgus monkeys: Dosing schedules of groups G1 to G6 as administered in study weeks W1 to W10 for G3 to G6/W12 for G1 and G2. Each dot stands for a daily dose split into 2 or 3 administrations (filled circles: 2 administrations in 8 h intervals; open circles: 3× administrations in 6 h intervals) at a daily dose of 13 to 30 µg/kg as indicated. For G1 to G6 there is no increase of the daily dose over the study duration. For G6 the initial daily dose is 20 µg/kg administered at day 1 and 2 of week 1 and 2, and the daily dose is increased to 30 µg/kg at day 1 and 2 of weeks 4, 5 and 7, 8 (enlarged filled cycles).

Figure 21:
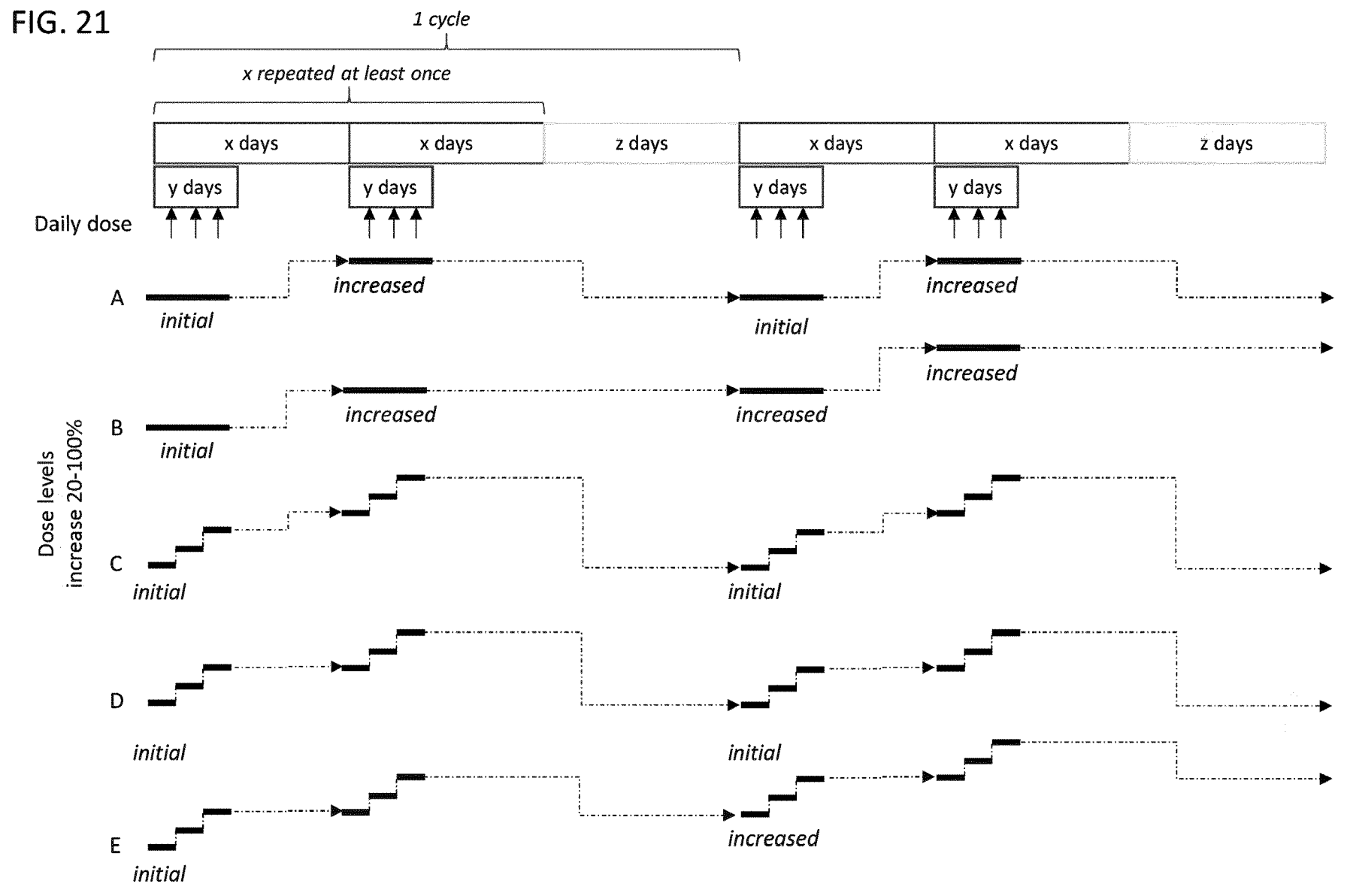

FIG. 21: Graphical representation of the pulsed cyclic administration regimens. A to E depict various scenarios of an increase of the daily dose: A—after the first treatment period x of each treatment cycle, whereas each treatment cycle starts again at the initial dose; B—after each treatment period x of each treatment cycle, whereas the daily dose is not increased after the break z; C—after each day of treatment within each treatment period x, wherein each treatment cycle starts again at the initial dose; D—after each day of treatment within each treatment period x, wherein the daily dose is not increased from one treatment period x to the next within a cycle and wherein each treatment cycle starts again at the initial dose; E—after each day of treatment within each treatment period x, wherein the daily dose is not increased from one treatment period x to the next within a cycle and wherein the daily dose of the first treatment period x of a new cycle starts at the daily dose of day 1 of the previous treatment period x.

```
                              Sequences

SEQ ID NO: 1 - human IL-2
   1   MYRMQLLSCI ALSLALVTNS APTSSSTKKT QLQLEHLLLD LQMILNGINN YKNPKLTRML
  61   TFKFYMPKKA TELKHLQCLE EELKPLEEVL NLAQSKNFHL RPRDLISNIN VIVLELKGSE
 121   TTFMCEYADE TATIVEFLNR WITFCQSIIS TLT
 153

SEQ ID NO: 2 - mature human IL-2
                              APTSSSTKKT QLQLEHLLLD LQMILNGINN YKNPKLTRML
  61   TFKFYMPKKA TELKHLQCLE EELKPLEEVL NLAQSKNFHL RPRDLISNIN VIVLELKGSE
 121   TTFMCEYADE TATIVEFLNR WITFCQSIIS TLT
 153

SEQ ID NO: 3 - human IL-15
   1   MRISKPHLRS ISIQCYLCLL LNSHFLTEAG IHVFILGCFS AGLPKTEANW VNVISDLKKI
 061   EDLIQSMHID ATLYTESDVH PSCKVTAMKC FLLELQVISL ESGDASIHDT VENLIILANN
 121   SLSSNGNVTE SGCKECEELE EKNIKEFLQS FVHIVQMFIN TS
 162

SEQ ID NO: 4 - mature human IL-15
                                                            NW VNVISDLKKI
 061   EDLIQSMHID ATLYTESDVH PSCKVTAMKC FLLELQVISL ESGDASIHDT VENLIILANN
 121   SLSSNGNVTE SGCKECEELE EKNIKEFLQS FVHIVQMFIN TS
 162

SEQ ID NO: 5 - human IL-15Rα
   1   MAPRRARGCR TLGLPALLLL LLLRPPATRG ITCPPPMSVE HADIWVKSYS LYSRERYICN
  61   SGFKRKAGTS SLTECVLNKA TNVAHWTTPS LKCIRDPALV HQRPAPPSTV TTAGVTPQPE
 121   SLSPSGKEPA ASSPSSNNTA ATTAAIVPGS QLMPSKSPST GTTEISSHES SHGTPSQTTA
 181   KNWELTASAS HQPPGVYPQG HSDTTVAIST STVLLCGLSA VSLLACYLKS RQTPPLASVE
 241   MEAMEALPVT WGTSSRDEDL ENCSHHL SEQ ID NO: 6 - sushi domain of IL-15Rα
       CPPPMSVE HADIWVKSYS LYSRERYICN SGFKRKAGTS SLTECVLNKA TNVAHWTTPS
       LKC SEQ ID NO: 7 - sushi + fragment of IL-15Rα
       ITCPPPMSVE HADIWVKSYS LYSRERYICN SGFKRKAGTS SLTECVLNKA TNVAHWTTPS
       LKCIRDPALV HQRPAPP SEQ ID NO: 8 - linker
       SGG SGGGGSGGGS GGGGSGG SEQ ID NO: 9 - RLI2
 001   ITCPPPMSVE HADIWVKSYS LYSRERYICN SGFKRKAGTS SLTECVLNKA TNVAHWTTPS
 061   LKCIRDPALV HQRPAPPSGG SGGGGSGGGS GGGGSGGNWV NVISDLKKIE DLIQSMHIDA
```

-continued

Sequences

```
121  TLYTESDVHP SCKVTAMKCF LLELQVISLE SGDASIHDTV ENLIILANNS LSSNGNVTES
181  GCKECEELEE KNIKEFLQSF VHIVQMFINT S
211

SEQ ID NO: 10 - IL2v
  1                        APASSSTKKT QLQLEHLLLD LQMILNGINN YKNPKLTRML
 41  TAKFAMPKKA TELKHLQCLE EELKPLEEVL NGAQSKNFHL RPRDLISNIN VIVLELKGSE
101  TTFMCEYADE TATIVEFLNR WITFAQSIIS TLT

SEQ ID NO: 11 - Leader peptide of (IL-15N72D)2:IL-15Rαsushi-Fc:
     METDTLLLWV LLLWVPGSTG SEQ ID NO: 12 - IL-15Rαsushi(65aa)-Fc (IgG1 CH2-CH3):
  1  ITCPPPMSVE HADIWVKSYS LYSRERYICN SGFKRKAGTS SLTECVLNKA TNVAHWTTPS
 61  LKCIREPKSC DKTHTCPPCP APELLGGPSV FLFPPKPKDT LMISRTPEVT CVVVDVSHED
120  PEVKFNWYVD GVEVHNAKTK PREEQYNSTY RVVSVLTVLH QDWLNGKEYK CKVSNKALPA
180  PIEKTISKAK GQPREPQVYT LPPSRDELTK NQVSLTCLVK GFYPSDIAVE WESNGQPENN
240  YKTTPPVLDS DGSFFLYSKL TVDKSRWQQG NVFSCSVMHE ALHNHYTQKS LSLSPGK SEQ ID NO: 13 - IL-15N72D
                                                            NW VNVISDLKKI
061  EDLIQSMHID ATLYTESDVH PSCKVTAMKC FLLELQVISL ESGDASIHDT VENLIILAND
121  SLSSNGNVTE SGCKECEELE EKNIKEFLQS FVHIVQMFIN TS
```

EXAMPLES

1. Flow Cytometry

Antibodies for Mouse Experiments

For Teff Panel

| Antigen | Fluorophore | Clone | Manufacturer | Dilution |
|---|---|---|---|---|
| CD3 | PE-Cy7 ® | 145-2C11 | eBioscience ™ | 1:40 |
| CD4 | PerCP | RM4-5 | BD Pharmingen | 1:100 |
| CD8 | V500 | 53-6.7 | BD Horizon | 1:80 |
| CD44 | APC | IM7 | eBioscience ™ | 1:500 |
| CD122 | ef450 | TM-b1 | eBioscience ™ | 1:100 |
| NKG2D | PE | CX5 | eBioscience ™ | 1:40 |
| PD-1 | FITC | J43 | eBioscience ™ | 1:40 |
| Live/dead | Viab.Dye 780 | | eBioscience ™ | |
| Ki67 | A700 | SolA15 | eBioscience ™ | 0.35 μl/well |

For Treg/NK Cell Panel

| Antigen | Fluorophore | Clone | Manufacturer | Dilution |
|---|---|---|---|---|
| CD45 | FITC | 30-F11 | eBioscience ™ | 1:100 |
| CD3 | PE-Cy7 ® | 145-2C11 | eBioscience ™ | 1:40 |
| CD8 | V500 | 53-6.7 | BD Horizon | 1:80 |
| CD4 | PerCP | RM4-5 | BD Pharmingen | 1:100 |
| CD49b | ef450 | DX5 | eBioscience ™ | 1:20 |
| CD25 | APC | PC61.5 | eBioscience ™ | 1:300 |
| Live/dead | Viab.Dye 780 | | eBioscience ™ | |
| Ki67 | A700 | SolA15 | eBioscience ™ | 0.35 μl/well |
| FoxP3 | PE | FJK-15s | eBioscience ™ | 1 μl/well |

Antibodies for Cynomolgus Experiments

For T Eff Panel

| Antigen | Fluorophore | Clone | Manufacturer | μl/well |
|---|---|---|---|---|
| CD45 | PE-Cy7 ® | D058-1283 | BD biosciences | 2 |
| CD3 | APC-Cy7 ® | SP34-2 | BD biosciences | 2 |

-continued

| Antigen | Fluorophore | Clone | Manufacturer | μl/well |
|---|---|---|---|---|
| CD4 | V450 | L200 | BD biosciences | 2 |
| CD8 | HV605 | SK1 | BD biosciences | 2 |
| CD28 | APC | CD28.2 | BD biosciences | 2 |
| CD95 | FITC | DX2 | BD biosciences | 2 |
| CD122 | PE | Mik-β2 | BD biosciences | 2 |
| Fix. Viab | eFluor ® 506 | | eBioscience ™ | 0.5 |
| Ki-67 | A700 | B56 | BD biosciences | 2 |

For T Regs/NK Cells Panel

| Antigen | Fluorophore | Clone | Manufacturer | μl/well |
|---|---|---|---|---|
| CD45 | PE-Cy7 ® | D058-1283 | BD biosciences | 2 |
| CD3 | APC-Cy7 ® | SP34-2 | BD biosciences | 2 |
| CD4 | V450 | L200 | BD biosciences | 2 |
| CD8 | HV605 | SK1 | BD biosciences | 2 |
| CD20 | PE | 2H7 | BD biosciences | 2 |
| CD25 | APC | CD25-4E3 | BD biosciences | 2 |
| Fix. Viab | eFluor ® 506 | | eBioscience ™ | 0.5 |
| FoxP3 | A488 | 206D | Biolegend ® | 2 |
| Ki-67 | A700 | B56 | BD biosciences | 2 |

Monkey Blood Processing for PBMC

10 μl of blood was measured directly with DAPI by flow cytometry for viability detection (2 μl of DAPI/well, +190 μl of PBS+EDTA). 300 μl of fresh blood was incubated with 6 ml of red blood cell lysis buffer (BioLegend®, 10× buffer diluted in dH$_2$O to 1×) for 15 minutes (to obtain PBMC), protected from light, and centrifuged and 2× washed with 10 ml FACS Buffer (PBS, Lonza®+2% fetal bovine serum (U.S.), heat inactivated, Sigma Aldrich®). Centrifugation was conducted at 300 g for 5 min at 4° C. The cell suspension was resuspended in 0.5 ml FACS Buffer and 10 μl of cell suspension was measured with DAPI by flow cytometry to detect viability after red blood cell lysis (+90 μl FACS buffer, +1.2 μl DAPI). The cell suspension was seeded in to a 96V well plate with 2 wells per one sample, cells were centrifuged in the 96V plate (2200 rpm, 2 min. 4° C.) and stained by flow cytometry.

Flow Cytometry (FACS) Staining for Cynomolgus
Studies

Extracellular antigens (CD antigens) were stained using
the above flow cytometry panels—½ Teff panel, ½ Tregs/
NK panel—with a mixture of the appropriate extracellular
antibodies and fixable viability dye in FACS buffer (pre-
pared 50 μl/sample) for 30 min at 4° C. to prevent the
exposure to the light. Samples were washed twice with
FACS buffer and centrifuged at 2200 rpm and 4° C. for 2
min. Cells were fixed with 100 μl/well fixation buffer (1
fixation concentrate:3 fixation diluent) for 20 min at 4° C.
After the fixation procedure cells were permeabilized in
Perm. Buffer—1:9 in dH$_2$O for 5 min. at RT and centrifuged
at 2200 rpm and 4° C. for 2 min.

Intracellular antigens (Ki67 and FoxP3) were stained
using the above flow cytometry panels—½ Teff panel, ½
Tregs panel—with a mixture of the appropriate intracellular
antibodies plus 3 μl of rat serum/well in permeabilization
buffer (prepared 50 μl/sample) for 30 min at 4° C. to
prevented the exposure to the light. Samples were washed
twice with FACS buffer, centrifuged at 2200 rpm and 4° C.
for 2 min. Cells were resuspended in 200 μl of staining
buffer 120 μl of cell suspension measured in a 96V plate
immediately after staining.

Preparation of Murine Splenocytes

Spleens were obtained from mice and transferred into
gentleMACS C Tubes containing 5 ml of FACS buffer (PBS,
2 mmol EDTA +2% FBS) and kept on ice until next
processing. Each spleen was processed in a separate tube. C
Tubes were tightly closed and attached upside down onto the
sleeve of the gentleMACS Dissociator. GentleMACS Pro-
grams: m_spleen—was used for 60 sec. Spleens were com-
pletely dissociated to obtain a splenocyte suspension. The
cell suspension was passed through a 70 μm strainer (white)
into 50 ml falcon tubes. The cells were centrifuged at 1200
rpm for 10 min at 4° C. Pellets were resuspended in 1 ml of
ACK lysis buffer (Gibco) by pipetting the cells up and down
with 1 ml tip and another 2 ml of ACK lysis buffer were
added. Red blood cells were lysed for 10 minutes in order to
obtain splenocytes. After 10 minutes 27 ml of FACS buffer
was added. Splenocytes were again centrifuged at 1200 rpm,
10 min, 4° C., and the cell pellet was resuspended in 1 ml
of FACS buffer. The cell suspension was passed through a 30
μm strainer (green) into 14 ml falcon tubes.

Flow Cytometry (FACS) Staining for Murine
Studies

The splenocyte suspension was divided at 100 μl/well into
96V-well plates for staining in duplicates. Plates were cen-
trifuged at 2000 rpm for 3 min at 4° C. Cells were blocked
with Fc receptor block (anti-Mouse CD16/CD32—Fc block,
eBioscience™, 1 μl/well) and 10% mouse serum (2 μl/well)
in 17 μl of FACS buffer for 30 min at 4° C. Wells were
washed 2x with FACS Buffer by centrifugation at 2000 rpm
for 5 min at 4° C.

For extracellular staining, cells were stained with a mix-
ture of the appropriate extracellular antibodies (for T effector
cells against antigens: CD3, CD4, CD8, CD44, CD122
CD62L; for T$_{reg}$/NK cells against antigens: CD3, CD4,
CD8, CD49b, CD25) and fixed with Fixable Viability Dye
eFluor™ 780 (dilution 1:200, eBioscience™) in FACS
buffer (prepared 10 μl/sample) for 30 min at 4° C. (exposure to light prevented). Cells were washed 2x with FACS buffer
(200 μl, centrifuged at 2000 rpm for 3 min at 4° C.).

For fixation, cells from above were fixed with 100 μl/well
fixation buffer (1:3—concentrate:diluent; Fixation/Permea-
bilization concentrate, eBioscience™; Fixation/Permeabili-
zation diluent eBioscience™) for 30 min at 4° C. After the
fixation procedure cells were permeabilized in Perm. Buffer
(1:9 in dH$_2$O, 5 min in RT), and centrifuged (2200 rpm, 2
min, 4° C.).

For intracellular staining, cells from above were washed
2x with 100 μl μl/well wash/perm buffer (eBioscience™—
1:9—buffer:dH$_2$O) and centrifuged 2000 rpm for 3 min at 4°
C. The buffer was discarded and a mixture of appropriate
intracellular antibodies (for T effector cells against antigen:
Ki67; for T$_{reg}$/NK cells against antigens: Ki67 and FoxP3)
were added at 50 μl/sample in permeabilization buffer
(eBioscience™). Cells were incubated for 30 min at 4° C.
with prevention to the exposure to light. Cells were washed
2x with wash/perm buffer, centrifuged at 2000 rpm for 3 min
at 4° C. Cells were resuspended in 100 μl of FACS buffer,
transferred into FACS tubes or 96V plates for FACS analy-
sis.

Flow cytometry was carried out using a BD LSR-
Fortessa™ flow cytometer (Becton Dickinson) according to
manufacturer's instructions. Cytometry data were collected
using BD DiVA™ (BD BioSciences) Software and analyzed
using FlowJo® Software (Tree Star).

Determination of Wet Lung Weight

Lungs were gently removed from mice and put into
microcentrifuge 1.5 ml tubes. The weight of the wet lungs
within the microcentrifuge tube was determined. Then lungs
were gently dried for 10 hours and dried lungs were
weighted in Eppendorf tubes. Wet and dry weights were
noted for VLS calculation equaling the weight of wet lungs
minus the weight of dry lungs.

2. Pharmacokinetic and Pharmacodynamic Study of
RLI-15 by the i.v. and s.c. Routes in the
Cynomolgus Monkey—Pharmacodynamic Part RLI-15/SO-C101 pharmacodynamics were tested by
evaluating immune cell profiles following repeated i.v. or
s.c. administration in the cynomolgus monkey in two
phases.

Phase 1—Comparison i.v. vs. s.c.

In phase 1, cynomolgus monkeys (2 males per group)
were treated with RLI-15 for 4 consecutive days at doses 4,
10 and 25 μg/kg per administration each i. v. (over 60 min)
or s.c. according to the design as depicted in Table 2 and
FIG. 1A. At day 5 (D5) after daily administration blood
samples (0.5 ml) were collected into K2-EDTA tubes, pro-
cessed, stained and analyzed by flow cytometry as described
above and compared to blood samples taken at day −5 (D−5)
pre-dosing.

TABLE 2

| | | | | | RLI | |
| Group | admin. route | dosing days | RLI dose [µg/kg/admin] | RLI volume [ml/kg/admin] | concentration [µg/ml] | No. of males |
| --- | --- | --- | --- | --- | --- | --- |
| 1 | i.v. | 1, 2, 3, 4 | 4 | 5 | 0.8 | 2 |
| 2 | i.v. | 1, 2, 3, 4 | 10 | 5 | 2 | 2 |
| 3 | i.v. | 1, 2, 3, 4 | 25 | 5 | 5 | 2 |
| 4 | i.v. | 1, 2, 3, 4 | 4 | 0.05 | 80 | 2 |
| 5 | i.v. | 1, 2, 3, 4 | 10 | 0.05 | 200 | 2 |
| 6 | s.c. | 1, 2, 3, 4 | 25 | 0.05 | 500 | 2 |
| 7 | | not treated | — | | | 2 |

After the four consecutive daily dosing of RLI-15 proliferating Ki67$^+$ NK and CD8$^+$ T cells were determined at day 5 by immunofluorescence analysis. Both s.c. and i.v. administration lead to increased numbers of proliferating Ki67$^+$ NK cells (see FIG. 1B) and CD8$^+$ T cells (see FIG. 1C) in a dose dependent manner (compared to pre-dose values at day −5). Importantly, s.c. administration was more potent than i.v. administration, the latter reaching a plateau at a dose of 10 µg/kg RLI for Ki67$^+$ NK cells, whereas only a slight further increase was seen between 10 and 25 µg/kg for i. v. administration; accordingly, 15 µg/kg were selected as the s.c. dose for phase 2. The difference between s.c. and i.v. administration was likely caused by the difference in RLI-15 pharmacokinetics following the different routes of administration. Sc. administration resulted in a longer circulation of biologically active serum concentrations as compared to i.v. administration, which is interpreted to result in stronger NK and CD8$^+$ T cell activation by s.c. administration.

Phase 2—Comparison 2 vs. 4 Administrations

In phase 2, after a 2-week washout period, animals were treated over 3 weeks according to the experimental groups were continued with i.v. administration dosed with 40 µg/kg/administration on D22, D23, D36 and D37 (2 admin. in weeks 1 and 3, Group 2) and on D22-D25 and D36-D39 (in case of 4 admin. in weeks 1 and 3, Group 3).

Immunofluorescence analysis was performed and further samples were taken according to the schedule of FIG. 1A. The fraction of Ki67$^+$ cells was determined in the CD3$^-$CD8$^+$CD45$^+$ (NK cells) and CD3$^+$CD8$^+$CD45$^+$ (CD8$^+$ T cells) cell fraction. Data were collected from group 1 (1 admin. per week), groups 4, 5, 7 (pooled, 2 admin. in weeks 1 and 3) and group 6 (4 admin.). Lymphocyte counts were determined during hematology assessment, CD8$^+$ T cells and NK cells were determined by immunofluorescence and multiplication of their relative proportion within CD45$^+$ cells with total white blood cell counts. Lymphocyte counts were determined during hematology assessment and CD8 T cells and NK cells according to their relative proportion within CD45$^+$ cells multiplied with total white blood cell counts.

TABLE 3

| | | | | | RLI | |
| Group | admin. route | dosing days | RLI dose [µg/kg/admin] | RLI volume [ml/kg/admin] | concentration [µg/ml] | No. of males |
| --- | --- | --- | --- | --- | --- | --- |
| 1 | s.c. | 1 ↓ in weeks 1, 2, 3 | 15 | 0.05 | 300 | 2 |
| 2 | i.v. | 2 ↓ in week 1 2 ↓ in week 3 | 40 | 5 | 8 | 2 |
| 3 | i.v. | 4 ↓ in week 1 4 ↓ in week 3 | 40 | 5 | 8 | 2 |
| 4 | s.c. | 2 ↓ in week 1 2 ↓ in week 3 | 15 | 0.05 | 300 | 2 |
| 5 | s.c. | 2 ↓ in weeks 1, 2, 3 | 15 | 0.05 | 300 | 2 |
| 6 | s. c. | 4 ↓ in week 1 4 ↓ in week 3 | 15 | 0.05 | 300 | 2 |
| 7 | s. c. | 2 ↓ in weeks 1, 2, 3 | 15 | 0.05 | 300 | 2 |

*Experimental groups in phase 2 (↓ = injection)* as depicted in Table 3 and FIG. 1A (starting D22). Cynomolgus monkeys were dosed s.c. with 15 µg/kg/administration on study days 22 (D22), D29 and D36 (1 administration per week in weeks 1, 2 and 3, Group 1), D22, D23, D36 and D37 (in case of 2 admin. in weeks 1 and 3, Group 4), D22, D23, D29, D30, D36 and D37 (in case of 2 admin. in weeks 1, 2 and 3, Groups 5 and 7), and D22-D25 and D36-D39 (in case of 4 admin. in weeks 1 and 3, Group 6). Two groups The percentage of Ki67$^+$ (activated) NK cells of total NK cells and Ki67$^+$ (activated) CD8$^+$ T cells of total CD8$^+$ T cells are shown in FIG. 1D. Optimal activation (measures as Ki67$^+$) of both NK cells and CD8$^+$ T cells in monkeys can be reached by 2 daily s.c. administrations per week on 2 consecutive days, whereas 4 daily consecutive administrations within one week do not provide any additional benefit with respect to activated NK cells and CD8$^+$ T cells, measured at day 5 after administration. This is surprising based on the short in vivo half-life of RLI-15 of only a few hours.

Phase 2—Repeating of Weekly Administrations

Looking at total lymphocyte counts from animals of Group 5 (2 animals, lymphocyte analysis performed on day 5 of each dosing week, i.e. D5, D26, D39 and D46), 2 daily s.c. administrations over 3 weeks in Phase 2 promoted an increase of total lymphocytes, CD8$^+$ T cells and NK cells, whereas from the 2$^{nd}$ to the 3$^{rd}$ week levels of NK cells and CD8$^+$ T cells were maintained but did not further increase (see FIG. 1E). Accordingly, repeated treatment of monkeys with 2 daily administrations on 2 consecutive days once or twice, i.e. for 2 or 3 weeks, was considered optimal, as a plateau was reached in the 3$^{rd}$ week and no additional benefit for further repetition was expected.

Phase 1 and Phase 2—Repeating of Monthly Cycles

Given the finding that following the treatment break between phase 1 and phase 2 NK cells and CD8$^+$ T cells can be activated again 18 days after the last treatment (day 22-day 4), it was assumed that the 2 or 3 repetitions of the 2 daily administrations on consecutive days can be again repeated after a treatment break of about 5 to 20 days.

Phase 2—Comparison Cell Activation vs. Cell Expansion

FIG. 1 F to I show either cell activation of Ki-67$^+$ NK cells (F) and CD8+ Ki-67$^+$ T cells (H) (each in percent of all NK cells or CD8$^+$ T cells, respectively) or cell expansion of NK cells (G) and CD8$^+$ T cells (I) (as cell counts) of animals 69 and 70 (Group 5). The pulsed dosing with 2 consecutive daily doses in phase 2 lead to a strong activation of both NK cells and CD8$^+$ T cells which again steeply declined during the 5 day treatment breaks. In both the 2$^{nd}$ and the 3$^{rd}$ cycle the 2 doses resulted in another activation of NK cells and CD8$^+$ T cells, for NK cells with a trend to weaker activation for the latter cycles. Looking at cell expansion of NK cells and CD8$^+$ T cells of the same animals, the 2 first cycles of 2 daily consecutive doses lead to a steady increase of the number of cells, whereas the 3$^{rd}$ cycle did not lead to a further increase, for animal 70 NK cell counts were even decreasing after the 3$^{rd}$ dosing cycle of phase 2.

3. Pharmacokinetic and Pharmacodynamic Study of RLI-15 by the i.v. and s.c. Routes in the Cynomolgus Monkey-Dense Dosing In a separate experiment it was tested whether 4 daily doses of RLI-15/SO-C101 on 4 consecutive days in 4 weekly cycles lead to improved pharmacodynamic effects. RLI-15 at dose of 100 μg/kg was injected s.c. in 1 female and 1 male cynomolgus monkeys on 4 consecutive days (D1-4; D8-11, D15-18, D22-25). The pharmacodynamic activity was evaluated on Days 5, 12, 19 and 26. Assessment of absolute and relative numbers of lymphocyte subsets in peripheral blood of all animals was determined by flow cytometry. Absolute lymphocyte subset counts were determined using BD TruCount™ tubes and reported as NK cells (CD16$^+$)-CD3$^-$CD16$^+$, Total T lymphocytes (CD3$^+$)-CD3$^+$, Helper T lymphocytes (CD4)-CD3$^+$CD4$^+$CD8$^-$, Cytotoxic T lymphocytes (CD8$^+$)-CD3±CD4$^-$CD8$^+$ and B lymphocytes (CD20$^+$)-CD3$^-$CD20$^+$, each as cells per μl of whole blood (FIG. 2).

Looking at NK cell and CD8$^+$ T cell counts (FIG. 2), the 1$^{st}$ cycle of 4 daily doses on 4 consecutive days leads to a strong expansion of lymphocytes with increasing numbers of NK cells and CD8$^+$ T cell. However, already after the 2$^{nd}$ cycle numbers of lymphocytes, NK cells and CD8$^+$ T cells declined, which continued also for the 3$^{rd}$ and 4$^{th}$ cycle. Comparing these results to the less dense dosing schedule shown in FIG. 1 E, where increasing/high cell counts were observed in the treated monkeys over 3 cycles, it becomes clear that no benefits were observed for a very dense and continuous schedule with 4 consecutive administrations per week on the expansion of NK and CD8$^+$ T cells.

4. Human/In Vitro to Cynomolgus/In Vivo Correlation

The in vitro proliferation of immune cell populations in peripheral blood, obtained from human and cynomolgus monkeys, after RLI-15/SO-C101 exposure was determined by flow cytometry in order to calculate the half maximal effective concentration (EC50) of RLI-15 for the proliferation of human and cynomolgus monkey NK and CD8$^+$ T cells as well as the 10% and 90% effective concentrations (EC10, EC90).

There was a strong correlation between NK and CD8$^+$ T cell activation in vitro and in vivo as shown in FIG. 3. The relationship between concentration and response in vitro correlated well with the relationship between $C_{max}$ following s.c. administration and NK and CD8$^+$ T cell activation levels in cynomolgus monkeys. For example, RLI-15 at 4 μg/kg and the corresponding $C_{max}$ of 1.2 ng/ml (approximately 48 pM) resulted in 71% activated NK cells and 18% activated CD8$^+$ T cells. Similar activation levels were achieved in vitro at 0.93 ng/ml (approximately 37 pM) with human NK cells (64%) and CD8$^+$ T cells (17%) (FIG. 3). This dose and concentration response was used to determine the Minimal Anticipated Biologic Effect Level (MABEL), the Pharmacologic Active Doses (PAD) and, together with the No Observed Adverse Effect Level (NOAEL) and Maximum Tolerated Dose (MTD) to select the starting dose and dose escalation steps for clinical study SC103 (FIG. 3).

Minimal activation of NK cells and no activation of CD8$^+$ T cells was observed at a RLI-15 concentration of 0.1 ng/ml (approximately 4 pM) in vitro (FIG. 3). This concentration is considered as MABEL. A dose of 0.7 μg/kg was extrapolated to achieve this $C_{max}$ of 0.1 ng/ml, based on the observed relationship between SC dose and $C_{max}$. Receptor Occupancy (RO) calculated for this dose is between 0.5% and 2%, considering a $K_D$ of 200 pM and 800 pM, respectively. Pharmacologic doses range between 1.5 μg/kg and 25 μg/kg, corresponding to $C_{max}$ between 0.3 ng/ml (approximately 12 pM) and 14 ng/ml (approximately 560 pM) and ROs of 1.5% to 6% and 40% and 65%, respectively. About 50% NK cell but no CD8$^+$ T cell activation at the lower end of this dose range to complete NK and CD8+ T cell activation at the higher end were observed. The NOAEL of 80 μg/kg and the MTD of 100 μg/kg following SC administration were calculated to promote ROs of 80% to 95%. The above described cynomolgus monkey doses were converted into the corresponding human doses by allometric scaling, using a factor of 3.1 (CDER 2005).

As NK and CD8$^+$ T cell activation represent a more sensitive parameter than receptor occupancy, the pharmacologic activity of RLI-15 determined in vitro and in cynomolgus monkeys was used for determining a starting dose and the escalation steps planned for clinical study SC103. Accordingly, a starting dose of 0.25 µg/kg was selected (FIG. 3). This dose representing the MABEL is expected to promote about 20% NK cell activation without affecting CD8$^+$ T cells. The subsequent dose levels as shown in FIG. 3 were selected to gradually increase NK cell activation and to promote CD8$^+$ T cell activation to 60% and ≤10% at dose level 2 and 80% and 25% at dose level 3, respectively, while reaching 100% NK and CD8$^+$ T cell activation at dose level 6. Subsequent dose levels are planned to increase by 66%, 60% and 50%. Dose level 7 would still be below the human equivalent of the NOAEL (26 µg/kg). Dose escalation in study SC103 will be made dependent on the safety observed at each dose level. Furthermore, PK parameters as well as NK and CD8$^+$ T cell activation analyzed in patients at each dose cohort will be considered into the dose escalation decision.

5. Outline for a Follow-Up Pharmacokinetic and Pharmacodynamic Study of RLI-15 by s.c. Route in the Cynomolgus Monkey In a similar setup as described in example 2 further dosing schedules are planned to be tested for s.c. administration of RLI-15/SO-C101:

route at any concentration tested. Finally, there was no significant increase in lung weight as a measure for vascular leak syndrome (VLS) at day 5 (see FIG. 4D).

Phase 2—Comparison of 2 Biweekly Cycles of 4 Doses i.v. vs. 2 Biweekly Cycles s.c.

FIG. 1 J to M compares percentages of Ki-67$^+$ NK cells and counts of Ki-67$^+$ NK cells for 2 biweekly cycles of 4 i.v. doses of each 40 µg/kg RLI-15 (Group 3 with animals 65 and 66) with 2 s.c. doses of each 15 µg/kg RLI-15 (Group 4 with animals 67 and 68). The same groups are shown for percentages of Ki-67$^+$ CD8$^+$ T cells and counts of Ki-67$^+$ CD8$^+$ T cells (FIG. 1 N to Q).

Activation of NK cells measured as percentage of Ki-67$^+$ of all NK cells was at least comparable for the 2 daily doses on 2 consecutive days for 15 µg/kg RLI-15 s.c. (total 60 µg/kg) compared to 4 daily doses on 4 consecutive days for 40 µg/kg RLI-15 i.v. (total 320 µg/kg) with a trend that the i.v. activation was reduced for the $2^{nd}$ cycle, whereas the s.c. activation was equal for the $1^{st}$ and the $2^{nd}$ cycle (FIG. 1 J and L). Activation of CD8$^+$ T cells appeared to be stronger for the 2 s.c. administrations of RLI-15 reaching more than 20% activated CD8$^+$ T cells, whereas the 4 i.v. doses lead to less than 20% activated CD8$^+$ T cells (FIG. 1 N and P). On the other hand the 4 i.v. doses appear to have induced are

| | Groups | | | | | |
|---|---|---|---|---|---|---|
| Week | 1 | 2 | 3 | 4 | 5 | 6 |
| 1 | D1, D2 | D1, D2 | D1, D2 | D1, D2, D3, D4 | D1, D2, D3, D4 | D1 |
| 2 | D1, D2 | D1, D2 | D1, D2 | D1, D2, D3, D4 | D1, D2, D3, D4 | D1 |
| 3 | — | D1, D2 | — | — | — | D1 |
| 4 | D1, D2 | D1, D2 | — | D1, D2, D3, D4 | — | D1 |
| 5 | D1, D2 | D1, D2 | D1, D2 | D1, D2, D3, D4 | D1, D2, D3, D4 | D1 |
| 6 | — | D1, D2 | D1, D2 | — | D1, D2, D3, D4 | D1 |
| 7 | D1, D2 | D1, D2 | — | D1, D2, D3, D4 | — | D1 |
| 8 | D1, D2 | D1, D2 | — | D1, D2, D3, D4 | — | D1 |
| 9 | — | — | D1, D2 | — | D1, D2, D3, D4 | — |
| 10 | — | — | D1, D2 | — | D1, D2, D3, D4 | — |

Dx indicates administration of RLI-15 on the $x^{th}$ day of the respective week, e.g. D3 in week 6 indicates the administration of RLI-15 on the $3^{rd}$ day of week 6.

6. Pharmacodynamics in Mouse at Different Doses

The dose of RLI-15 showing a maximal activity on NK cells and memory CD8$^+$ T cells was investigated. Mice were injected with RLI-15 (SO-C101, RLI2) i.p. or s.c. at increasing concentrations of 10, 20, 35 and 50 µg/dose once daily for 4 consecutive days. On day 5, lungs were harvested, and splenocytes were isolated and the relative expansion of NK cells, memory CD8$^+$ T cells and T regulatory cells (CD4$^+$ CD25$^+$FoxP3$^+$ T cells) was determined by flow cytometry on day 5 (FIG. 4).

RLI-15 at all tested concentrations induced high expansion of NK cells and memory CD8$^+$ T cells (see FIG. 4A and B). Whereas the highest expansion of NK cells was seen when mice were injected with 20 µg/dose, the maximal expansion of memory CD8$^+$ T cells was achieved when mice were injected with 35 µg/dose. There was no expansion of T regulatory cells under any dose of RLI-15 tested (see FIG. 4C). Interestingly, the expansion of NK cells and memory CD8$^+$ T cells in mice injected with RLI-15 at 50 µg/dose showed a decreasing tendency in comparison to the lower RLI-15 concentration of 35 µg/dose. There were no significant differences in the relative expansion of NK cells and memory CD8$^+$ T cells by RLI-15 administered via i.p. or s.c.

more constantly increase of CD8$^+$ T cell counts (FIG. 1 O and Q). In summary, 2 s.c. doses of RLI-15 on 2 consecutive days are at least comparable to 4 i.v. doses on 4 consecutive days.

7. Efficacy of i.p. Administration of RLI-15 in Varying Schedules in the Metastatic Renca Tumor Model The anti-metastatic activity of RLI-15 at a dose of 20 µg was investigated in a renal cell carcinoma (RENCA, BALB/c, females) mouse model (14 or 16 mice/group, 8 mice tumor progression, 6 or 8 mice pharmacodynamics). RLI-15 (SO-C101, RLI2) in 200 µl saline/daily dose was administered in different schedules starting at day 1 (D1) via i.p. route after $10^5$ RENCA tumor cells (in 300 µl saline) had been injected via i.v. injection into the tail vein on day 0. The lungs containing metastasis were weighted on day 16 (see FIG. 5A). The following groups/schedules were tested:

0) Naïve: no treatment
1) Renca $5 \times 10^5$ only
2) Renca $5 \times 10^5$+20 µg RLI2 i.p. D1-4+D8-11
3) Renca $5 \times 10^5$+20 µg RLI2 i.p. D1-4
4) Renca $5 \times 10^5$+20 µg RLI2 i.p. D1-2+D8-9
5) Renca $5 \times 10^5$+20 µg RLI2 i.p. D1+D8

FACS analysis was performed at day 5 and day 12. Weight and survival of mice was monitored 2-3 times/week, on day 16 mice were sacrificed and lungs were harvested and assessed for their weight with only short contact with filter paper to remove excess surface liquid.

TABLE 4

| Lung weight data at Day 16 (8 mice per group) | | |
| --- | --- | --- |
| | average/g | % reduction |
| tumor control | 0.67 | |
| RLI-15 20 µg i.p. D1-D4 + D8-11 | 0.22 | 67% |
| RLI-15 20 µg i.p. D1-D4 | 0.23 | 66% |
| RLI-15 20 µg i.p. D1-2 + D8-9 | 0.32 | 52% |
| RLI-15 20 µg i.p. D1 + D8 | 0.40 | 40% |

RLI-15 dosed at 20 µg in a daily dose i.p. decreased the lung metastasis by up to about 70% when compared to control tumor-bearing mice (see Table 4 and FIG. 5B), whereas schedules with repeated dosing on D1-D4 were superior to dosing on D1-D2+D8-D9 and D1+D8. Two 4-day series of dosing (D1-D4+D8-D11) were not significantly better than one 4-day series (D1-D4). 4 daily doses on 4 consecutive days (D1-D4) appear to be better than spread over two weeks (D1-D4+D8-D11).

The proliferation of NK cells and memory CD8$^+$ T cells was evaluated on day 5 and day 12 from 2 mice per group (see FIG. 5D and E) by analysis of splenocytes analyzed for the relative expansion of immune cells. RLI-15 treatment induced high proliferation in both immune cell types, which persisted on day 12 after the start of the treatment. D1-D4 dosing (D1-D4 and D1-D4+D8-D11 schedules, identical until Day 5) showed high expansion of NK cells and CD8 cells at Day 5, markedly higher than the schedules with less dosings until Day 5 (D1-D2 and D1). The D1-D4 week treatment schedule showed the highest pharmacodynamic (PD) activity on expansion of NK and CD8$^+$ T cells as detected on Day 12, which was superior to the 2 week treatment schedules (no additional benefit on PD was observed with a second round of RLI-15 administration). Treatments on D1+D8 or on D1-D2+D8-D9 resulted in a lower PD effect. Similar effects were observed for the activated subset of these cells (Ki-67$^+$).

No VLS was induced on Day 5 by RLI-15 treatment. RLI-15 treatment at all schedules prevented the mouse weight loss induced by the tumor burden (control), data not shown.

Interestingly, the expansion of both NK cells and CD8$^+$ T cells (being best for D1-D4 and D1-D4+D8-D11 schedules) very much resemble the efficacy of the treatment with respect to the treatment of lung metastasis, therefore being a suitable surrogate marker for efficacy.

8. Efficacy of s.c. Administration of RLI-15 Efficacy at Varying Doses in the Metastatic Renca Tumor Model The anti-metastatic activity of RLI-15 (SO-C101, RLI2) at doses of 10 µg or 20 µg was investigated in a renal cell carcinoma (RENCA, BALB/c, females) mouse model in comparison to an (IL-15Rα sushi)$_2$Fc fusion protein non-covalently bound to two IL-15N72D muteins (same sequence as disclosed for ALT-803 in US 2017/0088597, hereinafter IL15$_{N72D}$:IL15Rα$_{sushi}$-Fc or more precisely (IL15$_{N72D}$)$_2$IL15Rα$_{sushi}$-Fc) (8 mice/group). 10 µg or 20 µg RLI-15 (RLI2) in 200 µl saline/daily dose or 5 µg IL15$_{N72D}$:IL15Rα$_{sushi}$-Fc was administered in different schedules starting at day 1 (D1) via s.c. route after 10$^5$ RENCA tumor cells (in 300 µl saline) had been injected via i.v. injection into the tail vein on day 0. The following groups/schedules were tested:

0) Naïve: no treatment
    1) Renca 5×10$^5$ only
    2) Renca 5×10$^5$+20 µg RLI2 s.c. D1-4
    3) Renca 5×10$^5$+10 µg RLI2 s.c. D1-4
    4) Renca 5×10$^5$+20 µg RLI2 s.c. D1-3
    5) Renca 5×10$^5$+5 µg IL15$_{N72D}$:IL15Rα$_{sushi}$-Fc s.c. D1
IL15$_{N72D}$:IL15Rα$_{sushi}$-FC was dosed lower and less frequently due to the higher expected half-life.

Mice were monitored for weight and survival until mice were sacrificed on day 16 (see FIG. 6B). The lungs were harvested on day 16 with only short contact with filter paper to remove excess surface liquid, and the lung weight was determined as a measure for metastasis of the lungs (see Table 5 and FIG. 6A).

TABLE 5

| Lung weight data at Day 16 (8 mice per group) | | |
| --- | --- | --- |
| | average/g | % reduction |
| tumor control | 0.53 | |
| RLI-15 20 µg s.c. D1-D4 | 0.25 | 53% |
| RLI-15 10 µg s.c. D1-D4 | 0.32 | 40% |
| RLI-15 20 µg s.c. D1-D3 | 0.26 | 51% |
| IL15$_{N72D}$:IL15Rα$_{sushi}$-Fc 5 µg D1 | 0.20 | 62% |

All s.c. RLI-15 treatment doses and schedules showed a significant anti-metastatic efficacy by markedly reducing the lung weight at day 16. It appears that the 20 µg doses either at D1-D4 or D1-D3 were superior to the 10 µg D1-D4 schedule, and were nearly as good as 5 µg of IL15$_{N72D}$:IL15Rα$_{sushi}$-Fc administered once at D1. Further, efficacy of all treatment modalities was observed by no (for IL15$_{N72D}$:IL15Rα$_{sushi}$-Fc) or relatively modest (for RLI-15 treated mice) weight loss of the mice compared to untreated mice.

9. Clinical Trial of RLI-15/SO-C101

A first-in-human multicenter open-label phase 1/1b study to evaluate the safety and preliminary efficacy of SO-C101 as monotherapy and in combination with pembrolizumab in patients with selected advanced/metastatic solid tumors has been approved and will start soon (EurdraCT number 2018-004334-15). RLI-15 will be administered s.c. at a starting dose of 0.25 µg/kg and up to 48 µg/kg. In the combination part of the clinical trial RLI-15 will be combined with Keytruda® 25 mg/ml/pembrolizumab, which will be administered i. v. at a dose of 200 mg.

This study will assess the safety and tolerability of SO-C101 administered as monotherapy (Part A) and in combination with an anti-PD-1 antibody (pembrolizumab) (Part B) in patients with selected relapsed/refractory advanced/metastatic solid tumors (renal cell carcinoma, non-small cell lung cancer, small-cell lung cancer, bladder cancer, melanoma, Merkel-cell carcinoma, skin squamous-cell carcinoma, microsatellite instability high solid tumors, triple-negative breast cancer, mesothelioma, thyroid cancer, thymic cancer, cervical cancer, biliary track cancer, hepatocellular carcinoma, ovarian cancer, gastric cancer, head and neck squamous-cell carcinoma, and anal cancer), who are refractory to or intolerant of existing therapies known to provide clinical benefit for their condition.

Part A will start with an SO-C101 monotherapy dose escalation from 0.25 µg/kg to 48 µg/kg SO-C101 administered s.c. and will continue until the maximum tolerated dose (MTD) and/or the recommended phase 2 dose (RP2D) of SO-C101 monotherapy is defined. Patients will be treated with SO-C101 on day 1 (±1 day; Wednesday), day 2 (Thursday), day 8 (Wednesday), and day 9 (Thursday) of the 21-day cycle (FIG. 7A). The start of the treatment (day 1) is planned to be on a Wednesday as much as possible to allow biomarker sampling (fresh peripheral blood mononuclear cells [PBMCs] transfer to the central laboratory) on weekdays. However, as long as the two doses per week are given on consequent days (day 1 and day 2) and the second week dosing (day 8 and day 9) takes place 7 days after day 1, there will be ±1 day flexibility for the day 1 dosing to take place on a Tuesday or on a Thursday. Monotherapy dose escalation will continue until the MTD and/or RP2D is reached as per the dose escalation schema. If the MTD is not reached at the end of the planned dose escalation cohorts, the recruitment will stop to assess RP2D. Patients recruited in Part A will continue treatment at their assigned dose level. Patients will be discontinued from study treatment for any of the following events: (i) Radiographic disease progression; (ii) Clinical disease progression (investigator assessment); (iii) AE (inter-current illness or study treatment-related toxicity, including dose-limiting toxicities, that would, in the judgment of the investigator, affect assessments of clinical status to a significant degree or require discontinuation of study treatment)

The starting dose of Part B is planned to be 1.5 µg/kg SO-C101 administered as in Part A, which will be combined progression, pembrolizumab treatment could continue for up to 1 year as assessed by the DEC, if the patient does not progress and can tolerate the treatment. In case pembrolizumab needs to be stopped, SO-C101 treatment could continue until disease progression or unacceptable toxicity. Patients will be discontinued from study treatment for any of the following events: (i) Radiographic disease progression; (ii) Clinical disease progression (investigator assessment); (iii) AE (inter-current illness or study treatment-related toxicity, including dose-limiting toxicities, that would, in the judgment of the investigator, affect assessments of clinical status to a significant degree or require discontinuation of study treatment)

10. Tumor Cell Killing In Vitro by Concomitant Combination of RLI-15 and Daratumumab Human PBMC were isolated by ficoll separation from buffy coats of 5 healthy blood donors. Isolated human PBMC ($1 \times 10^6$) were incubated with RLI-15 (SO-C101) at a concentration of 1 nM, daratumumab at concentrations of 0.1, 1 and 10 nM and DiD-labelled (Vybrant® DiD-labeling, ThermoFisher according to manufacturer's instructions) Daudi tumor cells (40,000 cells/well) for 20 h at 37° C. (E:T ratio 25:1) with serum inactivated by heat (20 min, 56° C.—HI serum). Next, cells were stained with a mixture of fluorescent labelled antibodies and DAPI as shown in Table 6 (LAMP-1 was omitted from the staining due to late time of analysis for this degranulation marker). The percentage of dead (DAPI positive) DiD$^+$ Daudi cells was detected by flow cytometry. Immune cell markers were used to distinguish hPBMC from the Daudi tumor cells. The DiD labelling of Daudi cells was performed before the co-cultivation with human PBMC. DiD at 5 µl/$1 \times 10^6$ cells was added to Daudi tumor cells in serum-free RPMI and incubated at 37° C. for 30 min. Cells were washed twice (5 min, 1500 rpm) with RPMI medium containing FCS.

TABLE 6

| labels for flow cytometry | | | | | | |
|---|---|---|---|---|---|---|
| | marker | fluorochrome | µl/sample | clone | cat. no. | provider |
| NK cells | LAMP-1 (CD107a) | PE | 3 | H4A3 | 1P-671-T100 | EXBIO |
| | CD45 | BV605 | 1 | HI30 | 564047 | BD |
| | CD3 | APC ef780 | 1 | OKT3 | 47-0037-42 | Thermo |
| | CD8 | PE-Dylight | 1 | MEM-31 | T5-207-T100 | EXBIO |
| | CD16 | PE-Cy7 | 1 | 3G8 | 302016 | BioLegend |
| | CD56 | FITC | 2 | MEM-188 | 1F-231-T100 | EXBIO |
| Daudi | DiD | APC | 5 µl/1 M | | D7757 | Thermo |
| | DAPI | Pac blue | 1.2 | | | | with a fixed dose of pembrolizumab (200 mg i.v. every 3 weeks). Patients will be treated with escalating doses of SO-C101 on day 1 (±1 day) (Wednesday), day 2 (Thursday), day 8 (Wednesday), and day 9 (Thursday) together with a fixed dose of pembrolizumab (200 mg i.v. every 3 weeks) given on the day 1 administration of SO-C101 (FIG. 7B). Pembrolizumab will be administered within 30 minutes after the first dose of SO-C101 and as outlined in the package insert. The start of the treatment (day 1) is planned to be on a Wednesday as much as possible to allow biomarker sampling (fresh PBMCs transfer to the central laboratory) on weekdays. However, as long as the two doses of SO-C101 per week are given on consequent days (day 1 and day 2) and the second week SO-C101 dosing (day 8 and day 9) takes place 7 days after day 1, there will be ±1 day flexibility. Patients will continue SO-C101 and pembrolizumab treatment at the assigned dose level of SO-C101. In case SO-C101 needs to be stopped for reasons other than disease Whereas the presence of RLI-15 or the presence of 0.1 nM daratumumab only non-significantly increased the number of dead tumor cells (increase from about 15% to about 18% or 20%, respectively), the combination of RLI-15 with 0.1 nM daratumumab lead to more pronounced increase of dead tumor cells (about 26%). Comparably even higher numbers of dead cells were observed for increased concentrations of daratumumab at 1 nM, whereas apparently saturation was achieved at this value as no further increase was observed for 10 nM daratumumab. Further, the presence of RLI-15 always increased the number of dead tumor cells compared the respective group without RLI-15. (see FIG. 8)

In conclusion, RLI-15 synergized with daratumumab in tumor cell killing of Daudi cells in vitro, when added concomitantly.

11. Tumor Cell Killing In Vitro by a Sequential Combination of RLI-15 and Daratumumab Human PBMC were isolated by ficoll separation from buffy coats of 6 healthy blood donors. Isolated human PBMC ($1\times10^6$) were incubated with RLI-15 (SO-C101) at concentration of 0.1 nM at 37° C. for 48 h. Next, the stimulated PBMC were incubated in absence or with increasing concentrations of daratumumab (0.1, 1 or 10 nM) and DiD-labelled Daudi tumor cells (40,000/well) at 37° C. for 4 h (E:T ratio 1:1) using either active serum or serum inactivated by heat (20 min, 56° C.). Next, cells were stained with a mixture of fluorescent labelled antibodies and DAPI as shown in Table 6. The percentage of dead (DAPI positive) $DiD^+$ Daudi cells was detected by flow cytometry. Immune cell markers were used to distinguish hPBMC from the Daudi tumor cells. The DiD labelling of Daudi cells was performed before the co-cultivation with human PBMC. DiD at 5 µl/$1\times10^6$ cells was added to Daudi tumor cells in serum-free RPMI and incubated at 37° C. for 30 min. Cells were washed twice (5 min, 1500 rpm) with RPMI medium containing FCS.

Similar to the concomitant setting in example 10, the addition of daratumumab lead to a synergistic increase of dead tumor cells, whereas in the heat inactivated (HI) serum there was hardly an additional increase from 0.1 nM to 1 nM and no increase from 1 nM to 10 nM of daratumumab, but in contrast % of dead tumor cells further increased to >60% for incubation in active serum which points to a further synergistic effect with the active complement (complement-dependent cytotoxicity—CDC). Accordingly, RLI-15 and daratumumab synergistically killed Daudi cell also in a sequential setting in vitro. (see FIG. 9)

12. Anti-Tumor Efficacy of Concomitant Combination of RLI-15 and Daratumumab in Multiple Myeloma In Vivo CB17 SCID mice were inoculated s.c. with $1\times10^7$ RPMI8226 myeloma cells, an established model for multiple myeloma. The treatment started at day 0 (randomization day, tumor volume ~100 mm³). RLI-15 was administered s.c. at 1 mg/kg at days 0, 1, 2 and 3 and daratumumab was administered i.p. at 20 mg/kg at day 4, one group with each RLI-15 (SO-C101) or daratumumab alone, and one group in a combination. As a control, saline was administered at 10 µl/g s.c. at days 0, 1, 2 and 3. 10 animals per group were used.

Whereas control animals treated with saline showed a steady increase of the mean tumor volume (black solid line in FIG. 10A), both monotherapy treatment groups with RLI-15 and daratumumab showed a decreased tumor growth (grey dotted line for daratumumab and black dotted line for RLI-15 in FIG. 10A), the combined treatment with RLI-15 and daratumumab even lead to a synergistic shrinkage of the tumor volume (grey solid line in FIG. 10A). Looking at individual animals, the combined treatment with RLI-15 and daratumumab lead to the rejection of tumors in all test animals, whereas RLI-15 monotherapy only in 25% of test animals. For both the control group and the daratumumab group none of the test animals rejected the tumors (see FIG. 10B, grey solid line for combination group, black dotted line for RLI-15; both saline control group and daratumumab group run with x-axis).

Accordingly, the synergistic interaction of RLI-15 and daratumumab observed in vitro was confirmed in the RPMI8226 multiple myeloma in vivo model in the concomitant setting.

13. Anti-Tumor Efficacy of Sequential Combination of RLI-15 and Daratumumab in Multiple Myeloma In Vivo As in example 12, CB17 SCID mice were inoculated s.c. with $1\times10^7$ RPMI8226 myeloma cells. The treatment started at day 0 (randomization day, tumor volume ~100 mm³). Daratumumab was administered i.p. at 20 mg/kg at day 0, whereas in this sequential setting RLI-15 (SO-C101) was administered s.c. at 1 mg/kg at days 7, 8, 9 and 10. As control, saline was administered at 10 µl/g s.c. at days 0, 1, 2 and 3. 10 animals per group were used.

Again, the saline treated control group showed a continuous increase in tumor volume (black circles on black solid line, FIG. 11A). In this setting with a late start of treatment at day 7, the RLI-15 monotherapy treatment group showed only a little reduction in tumor growth (black circles on black dotted line), whereas both the daratumumab monotherapy (here started at day 0, open circles on grey dotted line) as well as the combination group of daratumumab with RLI-15 (grey circles on grey solid line, running together with grey dotted line) showed a decrease in tumor volume (see FIG. 11A). Whereas no difference could be observed for this sequential setting for the treatment groups daratumumab+RLI-15 vs. daratumumab alone and both the combination and daratumumab alone lead to a full rejection of tumor in all tested animals around day 28, about 25% of treated mice with daratumumab only again developed tumors after day 28 (see grey dotted line for the daratumumab only treatment vs. the grey solid line for the combination treatment, FIG. 11B).

Therefore, the reduction of the tumor volume induced by the combination of RLI-15 and daratumumab was similar to daratumumab monotherapy alone (A), however the combination treatment led to a rapid and durable tumor regression in all treated animals in contrast to single daratumumab treatment, where some animals later developed tumors again. Accordingly, also the sequential treatment with daratumumab first and RLI-15 starting one week later lead to an important therapeutic improvement.

14. Clinical Trial of RLI-15/SO-C101 Incombination With Daratumumab

A clinical study to evaluate the safety and preliminary efficacy of RLI-15/SO-C101 in combination with daratumumab is planned.

Initial 8 Weeks of Treatment

Following the 3-week cycle of SO-C101, SO-C101 will be administered s.c. at the established dose from example 9 at day 1 and day 2 (week 1) and day 8 and day 9 (week 2) followed by one week with no treatment with SO-C101. Daratumumab will be administered i. v. via infusion at a dose of 16 mg/kg once weekly. Infusion will be administered either at the $3^{rd}$ day of each week (i.e. day 3, day 10 and day 17) or at the $1^{st}$ day of each week (i.e. day 1, day 8 and day 15). The treatment according to this schedule will be continued for 8 weeks (i.e. 8 doses of daratumumab), as depicted in FIG. 12 A (with daratumumab administered at each $3^{rd}$ day of each week) and B (with daratumumab administered at each $1^{st}$ day of each week).

Alternatively, following the established 4-week cycle of daratumumab, SO-C101 will be administered s.c. at the established dose from example 9 at day 1 and day 2 (week 1) and day 8 and day 9 (week 2) followed by two weeks with no treatment with SO-C101. Daratumumab will be administered i.v. via infusion at a dose of 16 mg/kg once weekly. Infusion will be administered either at the 3' day of each week (i.e. day 3, day 10, day 17 and day 24) or at the 1st day of each week (i.e. day 1, day 8, day 15 and day 22). The treatment according to this schedule will be continued for 8 weeks (i.e. 8 doses of daratumumab), as depicted in FIG. 13 A (with daratumumab administered at each $3^{rd}$ day of each week) or B (with daratumumab administered at each $1^{st}$ day of each week).

Weeks 9 to 24 of Treatment

For the following weeks of treatment, SO-C101 will be administered s.c. at the established dose from example 9 at day 1 and day 2 (week 1) and day 8 and day 9 (week 2) followed by two weeks with no treatment with SO-C101. Daratumumab will be administered i.v. via infusion at a dose of 16 mg/kg once weekly for 2 weeks, followed by 2 weeks with no treatment with daratumumab in a 4-week cycle. Again, daratumumab will be administered either at the $3^{rd}$ day of such week (i.e. day 3 and day 10) or at the $1^{st}$ day of such wee k (i.e. day 1 and day 8) and the treatment will be continued for 16 weeks, i.e. until the end of the $24^{th}$ week of the total treatment. The schedule is depicted in FIG. 14 A (with daratumumab administered at each $3^{rd}$ day of each daratumumab treatment week) and B (with daratumumab administered at each $1^{st}$ day of each daratumumab treatment week).

Week 25 Until Disease Progression

Starting with week 25 of the total treatment, daratumumab will only be administered i.v. via infusion at a dose of 16 mg/kg once every 4 weeks, either on day 3 of such 4-week cycle or on day 1 of each 4-week cycle, whereas SO-C101 will be further administered s.c. at the established dose from example 9 at day 1 and day 2 (week 1) and day 8 and day 9 (week 2) followed by two weeks with no treatment with SO-C101. The schedule is depicted in FIG. 15 A (with daratumumab administered at each $3^{rd}$ day of each daratumumab treatment week) and B (with daratumumab administered at each $1^{st}$ day of each daratumumab treatment week).

According to this example for the three treatment periods above (initial 8 weeks, week 9 to 24 and week 25 until disease progression) the schedule for daratumumab compared to the administration of SO-C101 is not changed from one period to the other, i.e. for all periods daratumumab is either always administered on the $3^{rd}$ day of each week when administered, or on the $1^{st}$ day of each week when administered.

15. Follow-Up Pharmacokinetic and Pharmacodynamic Study of RLI-15 by s.c. Route in the Cynomolgus Monkey RLI-15 pharmacodynamics were tested by evaluating immune cell profiles following s.c. administration in a follow-up 10-week study in the cynomolgus monkey. RLI-15 (SO-C101) was administered at 40 or 80 µg/kg once daily for 1, 1 and 2, and 1, 2, 3 and 4 consecutive days every week (G3, G7 and G8) or for 2 weeks with a week pause (G1, G2 and G5) or with a two weeks pause (G4 and G6), in total for 10 weeks (FIG. 16). 1 male and 1 female per group were used. The pharmacodynamic activity on NK and CD8$^+$ T cells was evaluated in all groups on days –4, 5, 12, 19, 26, 33, 40, 47, 54, 61 and 68. The assessment of absolute and relative numbers of lymphocyte subsets in peripheral blood of all animals was determined by flow cytometry. Absolute lymphocyte subset counts were determined using percentage of cell populations obtained by flow cytometry which were recalculated to hematology leucocyte count depicted in cell count per µl (FIG. 17$a,b$). The percentage of proliferating Ki67$^+$ NK and CD8$^+$ T cells was evaluated by flow cytometry (FIG. 17$c,d$).

Looking at NK cell and CD8$^+$ T cell counts (FIG. 17$a,b$) all treatment schedules led to an increased number of NK cells. The selected doses were chosen to observe the possible differences between schedules focusing on the level of CD8$^+$ T cells. As NK cells are about one order of magnitude more sensitive to RLI-15 stimulation than CD8$^+$ T cells, the similar increase of NK cell counts in all schedules was therefore expected. As for CD8$^+$ T cells, the schedules exploring continuous stimulation once weekly (G7 and G8) showed the least CD8$^+$ T cell expansion under the continuous treatment. For example comparing equal total amounts of RLI-15 per treatment week (80 µg/kg) dosed at two days for two weeks with one week of break (G1), with continuously dosed over 8 weeks either split into two days (G3) or once a week (G8) shows that for both continuous dosing schedules the number of CD8$^+$ T cells already starts decreasing during the treatment, whereas the dosing schedule having the treatment break of one week (i.e. also in total less administered RLI-15) shows a continuous increase of the number of CD8$^+$ T cells (FIG. 17$a$). This effect becomes even clearer looking at the % of Ki-67$^+$ CD8$^+$ T cells (FIG. 17$c$), where clearly G1 outperforms G8 and G3 despite less total administered RLI-15. Each treatment period leads to a similar high activation of CD8$^+$ T cells with higher peaks, whereas for both continuous treatments also the % of activated CD8$^+$ T cells starts declining still during the treatment period (G8 and G3).

In conclusion, the treatment break is advantageous and the pulsed cyclic regimen leads to cyclic, high expansion and activation of CD8$^+$ T cells. Further, comparing G8 and G3, where same amounts of RLI-15 was administered, the % of Ki67$^+$ CD8$^+$ T cells is significantly higher, if the same total dose is split and administered over two consecutive days (G3) compared to administration at once on a single day (G1). Accordingly, the pulsed dosing regimen G3 is clearly advantageous over the continuous dosing schedule G8. Although, as described above, the amounts of administered RLI-15 were chosen to focus on CD8$^+$ T cells and are on the high end to see differences in NK cell responses, it still can be observed that NK cell proliferation is decreasing with continuous treatment of RLI-15 (compare G1 with G8 and G3 in FIG. 17$a$ and $c$).

Comparing G2 and G6, where the same total amount of RLI-15 is either administered at two consecutive days (day 1 and 2, 80 µg/kg each) or split over 4 consecutive days (day 1, 2, 3 and 4, 40 µg/kg each), it becomes apparent that extending the treatment from 2 to 4 days (even though reducing the daily dose) leads to stronger increase of CD8$^+$ T cell counts, whereas at the same time NK cell counts are lower (compare FIG. 17$b$, G2 and G6). However, looking at the % of activated CD8$^+$ T cells (Ki-671, the 2-day treatment schedule appears to be superior (FIG. 17$d$, G2 and G6).

16. Pharmacokinetic and Pharmacodynamic Study of RLI-15 by s.c. Route in the Cynomolgus Monkey by Intense Dosing RLI-15 pharmacodynamics under more intense dosing were tested in order to understand the limits of stimulation by evaluating immune cell profiles following s.c. administration in the cynomolgus monkey. RLI-15 (SO-C101) was administered at 3×7 µg/kg/day (G2) or 3×13 µg/kg/day (G3) and compared to 40 µg/kg administered 1×/day over 4 consecutive days/week (G1) (FIG. 18). 1 male and 1 female per group were used. The pharmacodynamic activity on NK and CD8⁺ T cells was evaluated in all groups on Days –4, 3, 5, 9 and 16. The assessment of absolute and relative numbers of lymphocyte subsets in peripheral blood of all animals was determined by flow cytometry as well as the mean fluorescence intensity (MFI) of selected markers. Absolute lymphocyte subset counts were determined using percentage of cell populations obtained by flow cytometry, which were recalculated to hematology leucocyte count depicted in cell count per µl (FIG. 19). The percentage of proliferating Ki67⁺ NK and CD8⁺ T cells was evaluated by flow cytometry (FIG. 19).

IL-2Rβ (CD122) expression levels were determined, as IL-2 and IL-15 have been described to induce exhaustion and terminal differentiation under chronical viral exposure (Beltra et al. 2016). Accordingly, high CD122 expression levels can be seen as a marker of exhaustion and terminal differentiation. Further, CD8 expression levels were determined, as low CD8 levels correlate with low sensitivity for antigens and low CD8 expression correlates with a type-2 T cell phenotype (Harland et al. 2014) which is lowering T cell activity and responsiveness to antigens.

The tested intense/dense dosing schedule with daily doses split into 3 administrations leads to substantially higher NK and CD8⁺ T cell counts compared to administration once daily over 4 consecutive days (FIG. 19, left panels). Looking at Ki67⁺ cells it becomes clear that starting at day 5 for NK cells and between day 5 and day 9 for CD8⁺ T cells the number of proliferating cells starts decreasing despite further stimulation (FIG. 19, middle panels). As there is a delay between measurable proliferation and the dosing, which is longer for CD8⁺ T cells than for NK cells, stimulation for more than 4 consecutive days does not add to proliferation. Additionally, it was observed that after day 5 the expression of the exhaustion marker CD122 on CD8⁺ T cells markedly increased again suggesting that too strong and/or too long exposure to an IL-2/IL-15Rβγ agonist leads to exhaustion of immune effector cells and does not further contribute to the treatment.

On the other hand the study showed that a short dense (i.e. split daily doses into multiple injections within a day, here 3 administrations per day) pulsing (for a few consecutive days, likely up to 4 days) with a high dose of RLI-15/SO-C101 resulted in a very high cell counts of both NK cells and CD8⁺ T cells as well as Ki67⁺ NK and CD8⁺ T cells, whereas the exhaustion markers had not increased yet. Accordingly, a dense pulsed cyclic dosing is seen as alternative promising schedule, which may even be combined with longer treatment breaks/resting periods of several weeks.

17. Pharmacokinetic and Pharmacodynamic Study of RLI-15 by s.c. Route in the Cynomolgus Monkey by Dense Pulsed Cyclic Dosing Schedule An intense/dense pulsed cyclic dosing schedule is planned to be translated to the clinics and tested for single agent activity, as relatively short half-lived IL-2/IL-15Rβγ agonists like RLI-15/S0-C101 are well suited for a dense pulsed schedule even at a high dose in order to allow withdrawal of exposure in case of safety complications. As previous experiments have shown, a stronger NK and CD8⁺ T cell expansion than with the pulsed cyclic dosing schedule is expected, but such regimen again should have a pulsing period with 2, 3 or 4 consecutive days to avoid the immune cell exhaustion.

Accordingly, a further pharmacokinetic and pharmacodynamic study of RLI-15 by s.c. route in the cynomolgus monkey testing the intense/dense pulsed cyclic dosing is presently being prepared in a similar fashion as in example 16 with the following dosing groups G1 to G6 (see FIG. 20): G1 and G2 are groups lasting 12 weeks (study weeks 1 to 12, W1 to W12); G3 to G6 are groups lasting 10 weeks (W1 to W10).

As outlined in FIG. 20, G1 and G2 are administered for 3 consecutive days without further treatment for the rest of 14 days, repeated once, followed by 3 weeks of break, whereas the daily dose about 40 µg/kg RLI-15 is split into 3 doses of 13 µg/kg in G1 and 2 doses of 20 µg/kg in G2. G3 starts with a pre-treatment of 3 consecutive days of administration without further treatment for the rest of the week, followed by 2 weeks of treatment break, followed by 3 consecutive days of administration without further treatment for the rest of the week, repeated once, followed by 1 week of treatment break; the daily dose of 40 µg/kg is split into 2 administration of 20 µg/kg. G4, G5 and G6 are administered for 2 consecutive days without treatment for the rest of the week, repeated once, followed by a week of break; for G4 the daily dose about 40 µg/kg RLI-15 is split into 3 doses of 13 µg/kg and for G5 the daily dose of 40 µg/kg RLI-15 is split into 2 doses of 20 µg/kg; both G4 and G5 are scheduled to have treatment at day 1 and 2 with no treatment for the rest of the week, being repeated once, followed by 1 week of treatment break. G6 is identical to G5 with the only difference that the initial daily dose of 40 µg/kg RLI-15 (again split into 2 doses of 20 µg/kg) is increased after the first cycle (2 administrations at consecutive days per week, repeated once, with one week of treatment break) by 50% to a daily dose of 60 µg/kg RLI-15 (split into 2 doses of 30 µg/kg) administered at 2 consecutive days per week, repeated once, with one week of treatment break.

It is assumed that the dense dosing preferably with a high dose of an IL-2/IL-15Rβγ agonist, e.g. RLI-15/SO-C101, for a pulse of 2, 3 or 4 consecutive days followed by a resting period with continuing such cycle over several weeks will translate into a pronounced CD8⁺ T cell expansion and activation (in addition to NK cells which are the more responsive effector cells), which may translate even into a strong single agent activity of such agonist, as this has been observed with IL-2 but not with long acting IL-2 variants, due to the avoidance of overstimulation and exhaustion of the effector cells. Additionally, in case of safety complications becoming more likely with high doses of the IL-2/IL-15Rβg agonist, such complications can get easier managed given the short half-life of the agonists of the invention as treatment can be stopped with only a short delay of the agent withdrawal becoming effective.

LITERATURE

Abramson, H. N. (2018). "Monoclonal Antibodies for the Treatment of Multiple Myeloma: An Update." *Int J Mol Sci* 19 (12).

Bacac, M., et al. (2017). "Abstract 1594: Enhancement of the anti-tumor activity of CEA TCB via combination with checkpoint blockade by PD-L1 and interleukin-2 variant immunocytokine." *Cancer Research* 77 (13 Supplement): 1594.

Bacac, M., et al. (2016). "A Novel Carcinoembryonic Antigen T-Cell Bispecific Antibody (CEA TCB) for the Treatment of Solid Tumors." *Clin Cancer Res* 22 (13): 3286-3297.

Beltra, J. C., et al. (2016). "IL2Rbeta-dependent signals drive terminal exhaustion and suppress memory development during chronic viral infection." *Proc Natl Acad Sci USA* 113 (37): E5444-5453.

Bentebibel, S. E., et al. (2017). The Novel IL-2 Cytokine Immune Agonist NKTR-214 Harnesses the Adaptive and Innate Immune System for the Treatment of Solid Cancers. *Society for Immunotherapy of Cancer* 2017 *Annual Meeting*. National Harbor, Md.

Bergamaschi, C., et al. (2018). "Optimized administration of hetIL-15 expands lymphocytes and minimizes toxicity in rhesus macaques." *Cytokine* 108: 213-224.

Bernett, M. J., et al. (2017). "IL15/IL15Rα heterodimeric Fc-fusions with extended half-lives." *Proceedings of the American Association for Cancer Research* 58: 408.

Caffaro, C. E., et al. (2019). Discovery of pharmacologically differentiated Interleukin 15 (IL-15) agonists employing a synthetic biology platform. *SITC* 2019. National Harbor, Md.

Castro, I., et al. (2011). "The basis of distinctive IL-2- and IL-15-dependent signaling: weak CD122-dependent signaling favors CD8+ T central-memory cell survival but not T effector-memory cell development." *J Immunol* 187 (10): 5170-5182.

CDER (2005). Guidance for Industry: Estimating the Maximum Safe Starting Dose in Initial Clinical Trials for Therapeutics in Adult Healthy Volunteers. US Department of Health and Human Services Food and Drug Administration Center for Drug Evaluation and Research (CDER)

Charych, D., et al. (2017). "Modeling the receptor pharmacology, pharmacokinetics, and pharmacodynamics of NKTR-214, a kinetically-controlled interleukin-2 (IL2) receptor agonist for cancer immunotherapy." *PLoS One* 12 (7): e0179431.

Charych, D., et al. (2013). "Abstract 482: Tipping the balance in the tumor microenvironment: An engineered cytokine (NKTR-214) with altered IL2 receptor binding selectivity and improved efficacy." *Cancer Research* 73 (8 Supplement): 482.

Charych, D. H., et al. (2016). "NKTR-214, an Engineered Cytokine with Biased IL2 Receptor Binding, Increased Tumor Exposure, and Marked Efficacy in Mouse Tumor Models." *Clinical Cancer Research* 22 (3): 680.

Chenoweth, M. J., et al. (2012). "IL-15 can signal via IL-15Ralpha, JNK, and NF-kappaB to drive RANTES production by myeloid cells." *J Immunol* 188 (9): 4149-4157.

Conlon, K., et al. (2019). *Phase I/Ib study of NIZ985 with and without spartalizumab (PDR001) in patients with metastatic/unresectable solid tumors*. AACR Annual Meeting, Atlanta, Ga.

Conlon, K. C., et al. (2015). "Redistribution, hyperproliferation, activation of natural killer cells and CD8 T cells, and cytokine production during first-in-human clinical trial of recombinant human interleukin-15 in patients with cancer." *J Clin Oncol* 33 (1): 74-82.

Conlon, K. C., et al. (2019). "Cytokines in the Treatment of Cancer." *J Interferon Cytokine Res* 39 (1): 6-21.

Darvin, P., et al. (2018). "Immune checkpoint inhibitors: recent progress and potential biomarkers." *Exp Mol Med* 50 (12): 165.

De Sousa Linhares, A., et al. (2018). "Not All Immune Checkpoints Are Created Equal." *Frontiers in Immunology* 9 (1909).

Edgar, R. C. (2004). "MUSCLE: multiple sequence alignment with high accuracy and high throughput." *Nucleic Acids Res* 32 (5): 1792-1797.

Elpek, K. G., et al. (2010). "Mature natural killer cells with phenotypic and functional alterations accumulate upon sustained stimulation with IL-15/IL-15Ralpha complexes." *Proc Natl Acad Sci USA* 107 (50): 21647-21652.

Felices, M., et al. (2018). "Continuous treatment with IL-15 exhausts human NK cells via a metabolic defect." *JCI Insight* 3 (3).

Frutoso, M., et al. (2018). "Emergence of NK Cell Hyporesponsiveness after Two IL-15 Stimulation Cycles." *J Immunol* 201 (2): 493-506.

Fyfe, G., et al. (1995). "Results of treatment of 255 patients with metastatic renal cell carcinoma who received high-dose recombinant interleukin-2 therapy." *J Clin Oncol* 13 (3): 688-696.

Gajewski, T. F., et al. (2013). "Cancer immunotherapy strategies based on overcoming barriers within the tumor microenvironment." *Curr Opin Immunol* 25 (2): 268-276.

Gearing, A. J. and R. Thorpe (1988). "The international standard for human interleukin-2. Calibration by international collaborative study." *J Immunol Methods* 114 (1-2): 3-9.

Ghasemi, R., et al. (2016). "Selective targeting of IL-2 to NKG2D bearing cells for improved immunotherapy." *Nat Commun* 7: 12878.

Giron-Michel, J., et al. (2005). "Membrane-bound and soluble IL-15/IL-15Ralpha complexes display differential signaling and functions on human hematopoietic progenitors." *Blood* 106 (7): 2302-2310.

Goujon, M., et al. (2010). "A new bioinformatics analysis tools framework at EMBL-EBI." *Nucleic Acids Res* 38 (Web Server issue): W695-699.

Han, K. P., et al. (2011). "IL-15:IL-15 receptor alpha superagonist complex: high-level co-expression in recombinant mammalian cells, purification and characterization." *Cytokine* 56 (3): 804-810.

Harland, K. L., et al. (2014). "Epigenetic plasticity of Cd8a locus during CD8(+) T-cell development and effector differentiation and reprogramming." *Nat Commun* 5: 3547.

Heaton, K. M., et al. (1993). "Human interleukin 2 analogues that preferentially bind the intermediate-affinity interleukin 2 receptor lead to reduced secondary cytokine secretion: implications for the use of these interleukin 2 analogues in cancer immunotherapy." *Cancer Res* 53 (11): 2597-2602.

Hori, T., et al. (1987). "Establishment of an interleukin 2-dependent human T cell line from a patient with T cell chronic lymphocytic leukemia who is not infected with human T cell leukemia/lymphoma virus." *Blood* 70 (4): 1069-1072.

Hu, P., et al. (2003). "Generation of low-toxicity interleukin-2 fusion proteins devoid of vasopermeability activity." *Blood* 101 (12): 4853-4861.

Joseph, I. B., et al. (2019). "THOR-707, a novel not-alpha IL-2, elicits durable pharmacodynamic responses in non-human primates and efficacy as single agent and in combination with anti PD-1 in multiple syngeneic mouse models." *Proceedings of the American Association for Cancer Research* 60: 838.

Klein, C. (2014). "S41. Novel CEA-targeted IL2 variant immunocytokine for immunotherapy of cancer." *Journal for Immunotherapy of Cancer* 2 (Suppl 2): 18-18.

Klein, C., et al. (2013). "Abstract PR8: Novel tumor-targeted, engineered IL-2 variant (IL-2v)-based immunocytokines for immunotherapy of cancer." *Cancer Research* 73 (1 Supplement): PR8.

Klein, C., et al. (2017). "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines." *Oncoimmunology* 6 (3): e1277306.

Kurowska, M., et al. (2002). "Fibroblast-like synoviocytes from rheumatoid arthritis patients express functional IL-15 receptor complex: endogenous IL-15 in autocrine fashion enhances cell proliferation and expression of Bcl-x(L) and Bcl-2." *J Immunol* 169 (4): 1760-1767.

Larsen, S. K., et al. (2014). "NK cells in the tumor microenvironment." *Crit Rev Oncog* 19 (1-2): 91-105.

Lazear, E., et al. (2017). "Targeting of IL-2 to cytotoxic lymphocytes as an improved method of cytokine-driven immunotherapy." *Oncoimmunology* 6 (2): e1265721.

Liu, B., et al. (2018). "Evaluation of the biological activities of the IL-15 superagonist complex, ALT-803, following intravenous versus subcutaneous administration in murine models." *Cytokine* 107: 105-112.

Margolin, K., et al. (2018). "Phase I Trial of ALT-803, a Novel Recombinant Interleukin-15 Complex, in Patients with Advanced Solid Tumors." *Clin Cancer Res* 24 (22): 5552-5561.

Miller, J. S., et al. (2018). "A First-in-Human Phase I Study of Subcutaneous Outpatient Recombinant Human IL15 (rhIL15) in Adults with Advanced Solid Tumors." *Clin Cancer Res* 24 (7): 1525-1535.

Miyazaki, T., et al. (2018). "Pharmacokinetic and Pharmacodynamic Study of NKTR-255, a Polymer-Conjugated Human IL-15, in Cynomolgus Monkey." *Blood* 132 (Suppl 1): 2952-2952.

Needleman, S. B. and C. D. Wunsch (1970). "A general method applicable to the search for similarities in the amino acid sequence of two proteins." *J Mol Biol* 48 (3): 443-453.

Pearson, W. R. and D. J. Lipman (1988). "Improved tools for biological sequence comparison." *Proc Natl Acad Sci USA* 85 (8): 2444-2448.

Perdreau, H., et al. (2010). "Different dynamics of IL-15R activation following IL-15 cis- or trans-presentation." *Eur Cytokine Netw* 21 (4): 297-307.

Rhode, P. R., et al. (2016). "Comparison of the Super-agonist Complex, ALT-803, to IL15 as Cancer Immunotherapeutics in Animal Models." *Cancer Immunol Res* 4 (1): 49-60.

Ring, A. M., et al. (2012). "Mechanistic and structural insight into the functional dichotomy between IL-2 and IL-15." *Nat Immunol* 13 (12): 1187-1195.

Robinson, T. O. and K. S. Schluns (2017). "The potential and promise of IL-15 in immuno-oncogenic therapies." *Immunol Lett* 190: 159-168.

Romee, R., et al. (2018). "First-in-human Phase 1 Clinical Study of the IL-15 Superagonist Complex ALT-803 to Treat Relapse after Transplantation." *Blood* 131 (23): 2515-2527.

Rosenzwajg, M., et al. (2019). "Immunological and clinical effects of low-dose interleukin-2 across 11 autoimmune diseases in a single, open clinical trial." *Ann Rheum Dis* 78 (2): 209-217.

Shanafelt, A. B., et al. (2000). "A T-cell-selective interleukin 2 mutein exhibits potent antitumor activity and is well tolerated in vivo." *Nat Biotechnol* 18 (11): 1197-1202.

Silva, D.-A., et al. (2019). "De novo design of potent and selective mimics of IL-2 and IL-15." *Nature* 565 (7738): 186-191.

Smith, T. F. and M. S. Waterman (1981). "Comparison of biosequences." *Advances in Applied Mathematics* 2 (4): 482-489.

Solomon, B. L. and I. Garrido-Laguna (2018). "TIGIT: a novel immunotherapy target moving from bench to bedside." *Cancer Immunol Immunother* 67 (11): 1659-1667.

Soman, G., et al. (2009). "MTS dye based colorimetric CTLL-2 cell proliferation assay for product release and stability monitoring of interleukin-15: assay qualification, standardization and statistical analysis." *J Immunol Methods* 348 (1-2): 83-94.

Steel, J. C., et al. (2012). "Interleukin-15 biology and its therapeutic implications in cancer." *Trends Pharmacol Sci* 33 (1): 35-41.

Thaysen-Andersen, M., et al. (2016). "Recombinant human heterodimeric IL-15 complex displays extensive and reproducible N- and O-linked glycosylation." *Glycoconj J* 33 (3): 417-433.

Toutain, P. L. and A. Bousquet-Melou (2004). "Plasma terminal half-life." *J Vet Pharmacol Ther* 27 (6): 427-439.

Wadhwa, M., et al. (2013). "The 2nd International standard for Interleukin-2 (IL-2) Report of a collaborative study." *Journal of Immunological Methods* 397 (1): 1-7.

Waldmann, T. A. (2015). "The shared and contrasting roles of IL2 and IL15 in the life and death of normal and neoplastic lymphocytes: implications for cancer therapy." *Cancer Immunol Res* 3 (3): 219-227.

Wei, X., et al. (2001). "The Sushi domain of soluble IL-15 receptor alpha is essential for binding IL-15 and inhibiting inflammatory and allogenic responses in vitro and in vivo." *J Immunol* 167 (1): 277-282.

Wrangle, J. M., et al. (2018). "ALT-803, an IL-15 superagonist, in combination with nivolumab in patients with metastatic non-small cell lung cancer: a non-randomised, open-label, phase 1b trial." *Lancet Oncol* 19 (5): 694-704.

WO 2005/085282A1
WO 2007/046006A2
WO 2008/003473A2
WO 2008/143794A1
WO 2009/135031A1
WO 2012/065086A1
WO 2012/107417A1
WO 2012/175222A1
WO 2014/066527A2
WO 2014/145806A2
WO 2014/207173A1
WO 2015/018528A1
WO 2015/109124A2
WO 2016/060996A2
WO 2016/142314A1
WO 2017/046200A1
WO 2017/112528A2
WO 2018/071918A1
WO 2018/071919A1

WO 2018/102536A1
WO 2018/151868A2
WO 2018/213341A1
WO 2019/028419A1
WO 2019/028425A1
WO 2019/165453A1
WO 2019/173798A1
US 2003/0124678
US 2006/0057680
US 2007/0036752
US 2017/0088597
US 2018/0118805
US 2019/0092830
U.S. Pat. No. 5,229,109
U.S. Pat. No. 10,206,980
NCT02983045 at www.clinicaltrials.gov, as of 16 Aug. 2018
NCT03386721 at www.clinicaltrials.gov, as of 16 Aug. 2018
NCT02627284 at www.clinicaltrials.gov, as of 16 Aug. 2018
NCT03063762 at www.clinicaltrials.gov, as of 16 Aug. 2018
NCT03388632, at www.clinicaltrials.gov, as of 16 Aug. 2018
NCT01572493, at www.clinicaltrials.gov, as of 16 Aug. 2018
NCT01021059, at www.clinicaltrials.gov, as of 14 May 2019

Embodiments of the Invention

1. An interleukin-2/interleukin-15 receptor $\beta\gamma$ (IL-2/IL-15R$\beta\gamma$) agonist for use in treating or managing cancer or infectious diseases, comprising administering the IL-2/IL-15R$\beta\gamma$ agonist to a human patient using a cyclical administration regimen, wherein the cyclical administration regimen comprises:
   (a) a first period of x days during which the IL-2/IL-15R$\beta\gamma$ agonist is administered at a daily dose on y consecutive days at the beginning of the first period followed by x-y days without administration of the IL-2/IL-15R$\beta\gamma$ agonist,
   wherein x is 5, 6, 7, 8 or 9 days, and y is 2, 3 or 4 days;
   (b) repeating the first period at least once; and
   (c) a second period of z days without administration of the IL-2/IL-15R$\beta\gamma$ agonist, wherein z is 5, 6, 7, 8, 9, 10, 11, 12, 13, 14, 15, 16, 17, 18, 19 or 20 days.
2. The IL-2/IL-15R$\beta\gamma$ agonist for use of embodiment 1, wherein x is 6, 7 or 8 days, preferably 7 days.
3. The IL-2/IL-15R$\beta\gamma$ agonist for use of embodiments 1 or 2, wherein y is 2 or 3 days, preferably 2 days.
4. The IL-2/IL-15R$\beta\gamma$ agonist for use of any of embodiments 1 to 3, wherein z is 7 days.
5. The IL-2/IL-15R$\beta\gamma$ agonist for use of any of embodiments 1 to 4, wherein x is 7 days, y is 2 days and z is 7 days.
6. The IL-2/IL-15R$\beta\gamma$ agonist for use of any of embodiments 1 to 5, wherein the daily dose is 0.1 to 50 µg/kg, preferably 0.25 to 25 µg/kg, more preferably 0.6 to 10 µg/kg and especially 2 to 10 µg/kg.
7. The IL-2/IL-15R$\beta\gamma$ agonist for use according to any of embodiments 1 to 6, wherein the IL-2/IL-15R$\beta\gamma$ agonist is administered subcutaneously (s.c.) or intraperitoneally (i.p.), preferably s.c..

8. The IL-2/IL-15R$\beta\gamma$ agonist for use according to any of embodiments 1 to 7, wherein administration of the IL-2/IL-15R$\beta\gamma$ agonist in step (a) results in an increase of the % of Ki-67$^+$ NK of total NK cells in comparison to no administration of the IL-2/IL-15R$\beta\gamma$ agonist, and wherein administration of the IL-2/IL-15R$\beta\gamma$ agonist in step (b) results in a Ki-67$^+$ NK cell level that is at least 70% of the of the Ki-67$^+$ NK cells of step (a).
9. The IL-2/IL-15R$\beta\gamma$ agonist for use according to any of embodiments 1 to 8, wherein the IL-2/IL-15R$\beta\gamma$ agonist administration results in maintenance of NK cell numbers or preferably an increase of NK cell numbers to at least 110% as compared to no administration of IL-2/IL-15R$\beta\gamma$ agonist after at least one repetition of the first period, preferably after at least two repetitions of the first period.
10. The IL-2/IL-15R$\beta\gamma$ agonist for use according to any of embodiments 1 to 9, wherein the IL-2/IL-15R$\beta\gamma$ agonist administration results in NK cell numbers of at least $1.1 \times 10^3$ NK cells/µl after at least one repetition of the first period, preferably after at least two repetitions of the first period.
11. The IL-2/IL-15R$\beta\gamma$ agonist for use according to any of embodiments 1 to 10, wherein the cyclic administration is repeated over at least 3 cycles, preferably 5 cycles, more preferably at least 10 cycles and even more preferably until disease progression.
12. The IL-2/IL-15R$\beta\gamma$ agonist for use according to any of embodiments 1 to 11, wherein the daily dose selected within the dose range of 0.1 to 50 µg/kg is not substantially increased during the administration regimen, preferably wherein the dose is maintained during the administration regimen.
13. The IL-2/IL-15R$\beta\gamma$ agonist for use according to any of embodiments 1 to 12, wherein the cancer is a hematological cancer or a solid cancer.
14. The IL-2/IL-15R$\beta\gamma$ agonist for use according to any of embodiments 1 to 13, wherein the IL-2/IL-15R$\beta\gamma$ agonist has an in vivo half-life of 30 min to 24 h, preferably 1 h to 12 h, more preferably of 2 h to 6 h.
15. The IL-2/IL-15R$\beta\gamma$ agonist for use according to any of embodiments 1 to 14, wherein the IL-2/IL-15R$\beta\gamma$ agonist is at least 70% monomeric, preferably at least 80% monomeric.
16. The IL-2/IL-15R$\beta\gamma$ agonist for use according to any of embodiments 1 to 15, wherein the IL-2/IL-15R$\beta\gamma$ agonist is an interleukin 15 (IL-15)/interleukin-15 receptor alpha (IL-15R$\alpha$) complex.
17. The IL-2/IL-15R$\beta\gamma$ agonist for use according to embodiment 16, wherein the IL-15/IL-15R$\alpha$complex is a fusion protein comprising the human IL-15R$\alpha$ sushi domain or derivative thereof, a flexible linker and the human IL-15 or derivative thereof, preferably wherein the human IL-15R$\alpha$ sushi domain comprises the sequence of SEQ ID NO: 6, and wherein the human IL-15 comprises the sequence of SEQ ID NO: 4.
18. The IL-2/IL-15R$\beta\gamma$ agonist for use according to any of embodiments 1 to 17, wherein the IL-15/IL-15R$\alpha$ complex is SEQ ID NO: 9.
19. The IL-2/IL-15R$\beta\gamma$ agonist for use according to any of embodiments 1 to 18, wherein a checkpoint inhibitor is administered at the beginning of the first period (a) of each cycle.
20. The IL-2/IL-15R$\beta\gamma$ agonist for use according to embodiment 19, wherein the checkpoint inhibitor is an anti-PD-1 antibody, an anti-PD-L1 antibody, an anti-PD-L2 antibody, an anti-LAG-3 antibody, an anti- TIM-3 antibody or an anti-CTLA4 antibody, preferably an anti-PD-L1 antibody or an anti-PD-1 antibody.

21. An IL-2/IL-15Rβγ agonist for use in treating or managing cancer or infectious diseases, comprising administering the IL-2/IL-15Rβγ agonist according to the following administration regime (i) administration of the IL-2/IL-15Rβγagonist to a human patient at a daily dose on a first number of consecutive days; and (ii) a second number of days without administration of the IL-2/IL-15Rβγ agonist, wherein the first number is 2, 3 or 4 days and the second number is 3, 4 or 5 days.

22. The IL-2/IL-15Rβγ agonist for use of embodiment 21, wherein the administration regime is repeated at least once, preferably at least twice, more preferably at least 4 times, most preferably until disease progression.

23. The IL-2/IL-15Rβγ agonist for use of embodiment 21, wherein the first period is 2 days and the second period is 5 days.

24. The IL-2/IL-15Rβγ agonist for use of embodiments 21 or 23, wherein the daily dose is 0.1 to 50 µg/kg.

25. The IL-2/IL-15Rβγ agonist for use according to any of the embodiments 21 to 24, wherein the dose of 0.1 to 50 µg/kg is not substantially increased during the administration regimen, preferably wherein the dose is maintained during the administration regimen.

26. The IL-2/IL-15Rβγ agonist for use according to any of the embodiments 21 to 25, wherein the dose is 1 to 30 µg/kg, preferably 2 to 20 µg/kg and most preferably 2-10 µg/kg of the IL-2/IL-15Rβγ agonist.

27. The IL-2/IL-15Rβγ agonist for use according to any of the embodiments 21 to 26, wherein the IL-2/IL-15Rβγ agonist is administered subcutaneously (s.c.) or intraperitoneally (i.p.), preferably s.c.

28. The IL-2/IL-15Rβγ agonist for use according to any of embodiments 22 to 27, wherein administration of the IL-2/IL-15Rβγ agonist in step (i) results in an increase of the % of Ki-67$^+$ NK of total NK cells in comparison to no administration of the IL-2/IL-15Rβγ agonist, and wherein administration of the IL-2/IL-15Rβγ agonist after the first repetition results in a Ki-67$^+$ NK cell level that is at least 70% of the of the Ki-67$^+$ NK cells of step (i).

29. The IL-2/IL-15Rβγ agonist for use according to any of embodiments 22 to 28, wherein the IL-2/IL-15Rβγ agonist administration results in maintenance of NK cell numbers or preferably an increase of NK cell numbers to at least 110% as compared to no administration of IL-2/IL-15Rβγ agonist after at least one repetition of the period (i), preferably after at least two repetitions of the period (i).

30. The IL-2/IL-15Rβγ agonist for use according to any of embodiments 22 to 29, wherein the IL-2/IL-15Rβγ agonist administration results in NK cell numbers of at least $1.1 \times 10^3$ NK cells/µl after at least one repetition of the period (i), preferably after at least two repetitions of the first period.

31. The IL-2/IL-15Rβγ agonist for use according to any of the embodiments 21 to 30, wherein the cancer is a hematological cancer or a solid cancer.

32. The IL-2/IL-15Rβγ agonist for use according to any of the embodiments 21 to 31, wherein the IL-2/IL-15Rβγ agonist has an in vivo half-life of 30 min to 24 h, preferably 1 h to 12 h, more preferably of 2 h to 6 h.

33. The IL-2/IL-15Rβγ agonist for use according to any of the embodiments 21 to 32, wherein the IL-2/IL-15Rβγ agonist is at least 70% monomeric.

34. An IL-2/IL-15Rβγ agonist for use according to any of the embodiments 21 to 33, wherein the IL-2/IL-15Rβγ agonist is an IL-15/interleukin-15 receptor alpha (IL-15Rα) complex.

35. The IL-2/IL-15Rβγ agonist for use according to any of the embodiments 21 to 34, wherein the IL-15/IL-15Rα complex is a fusion protein comprising the human IL-15Rα sushi domain or derivative thereof, a flexible linker and the human IL-15 or derivative thereof, preferably wherein the human IL-15Rα sushi domain comprises the sequence of SEQ ID NO: 6, and wherein the human IL-15 comprises the sequence of SEQ ID NO: 4.

36. The IL-2/IL-15Rβγ agonist for use according to any of the embodiments 21 to 35, wherein the IL-15/IL-15Rα complex is SEQ ID NO: 9.

37. A kit comprising the IL-2/IL-15Rβγ agonist according to any of the embodiments 1 to 36, an instruction for use of the IL-2/IL-15Rβγ agonist in the cyclic administration regime according to any of the embodiments 0 to 20 or in the administration regime according to any of the embodiments 21 to 36 and optionally an administration device for the IL-2/IL-15Rβγ agonist.

38. The kit according to embodiment 37, which further comprises a checkpoint inhibitor and an instruction for use of the checkpoint inhibitor.

---

The invention claimed is:

1. A method of treating or managing cancer or infectious diseases comprising administering an interleukin-2/interleukin-15 receptor βγ (IL-2/IL-15Rβγ) agonist to a human patient using a cyclical administration regimen, wherein the cyclical administration regimen comprises:

(a) a first period of x days during which the IL-2/IL-15Rβγ agonist is administered at a daily dose on y consecutive days at the beginning of the first period followed by x-y days without administration of the IL-2/IL-15Rβγ agonist, wherein x is 5, 6, 7, 8, 9, 10, 11, 12, 13, 14, 15, 16, 17, 18, 19, 20 or 21 days, and y is 2, 3 or 4 days;

(b) repeating the first period at least once; and (c) a second period of z days without administration of the IL-2/IL-15Rβγ agonist, wherein z is 5, 6, 7, 8, 9, 10, 11, 12, 13, 14, 15, 16, 17, 18, 19, 20, 21, 28, 35, 42, 49, 56, 63 or 70 days;

wherein the IL-2/IL-15Rβγ agonist is an interleukin 15 (IL-15)/interleukin-15 receptor alpha (IL-15Rα) complex.

2. The method of claim 1, wherein x is 7 days, y is 2, 3 or 4 days and z is 7 days.

3. The method of claim 1, wherein the daily dose is a fixed dose independent of body weight of 7 μg to 3500 μg or wherein the daily dose is 0.1 μg/kg to 50 μg/kg.

4. The method of claim 1, wherein the daily dose is administered in a single injection.

5. The method of claim 1, wherein the daily dose is split into 2 or 3 individual doses that are administered within one day, wherein the time interval between administration of the individual doses is at least about 4 h and not more than 14 h.

6. The method of claim 1, wherein the IL-2/IL-15Rβγ agonist is administered subcutaneously (s.c.) or intraperitoneally (i.p.).

7. The method of claim 1, wherein administration of the IL-2/IL-15Rβγ agonist in step (a) results in (1) an increase of the % of Ki-67+ NK of total NK cells in comparison to no administration of the IL-2/IL-15Rβγ agonist, and wherein administration of the IL-2/

IL-15Rβγ agonist in step (b) results in a Ki-67$^+$ NK cell level that is at least 70% of the of the Ki-67$^+$ NK cells of step (a), (2) maintenance of NK cell numbers or an increase of NK cell numbers to at least 110% as compared to no administration of IL-2/IL-15Rβγ agonist after at least one repetition of the first period, after at least two repetitions of the first period, and/or (3) NK cell numbers of at least $1.1 \times 10^3$ NK cells/ul after at least one repetition of the first period, after at least two repetitions of the first period.

8. The method of claim 1, wherein the interleukin 15 (IL-15)/interleukin-15 receptor alpha (IL-15Rα) complex is a fusion protein comprising the human IL-15Rα sushi domain or derivative thereof, a flexible linker and the human IL-15 or derivative thereof.

9. The method of claim 8, wherein the human IL-15Rα sushi domain comprises the sequence of SEQ ID NO: 6, the human IL-15 comprises the sequence of SEQ ID NO: 4, and the IL-15/IL-15Rα complex comprises the sequence of SEQ ID NO: 9.

10. The method of claim 1, further comprising administering a therapeutic agent in combination with the IL-2/IL-15Rβγ agonist.

11. The method of claim 10, wherein the therapeutic agent is a checkpoint inhibitor selected from the group consisting of an anti-PD-1 antibody, an anti-PD-L1 antibody, an anti-PD-L2 antibody, an anti-LAG-3 antibody, an anti-TIM-3 antibody, an anti-CTLA4 antibody or an anti-TIGIT antibody.

12. The method of claim 10, wherein the therapeutic agent is a therapeutic antibody selected from the group consisting of an anti-CD38 antibody, an anti-CD19 antibody, an anti-CD20 antibody, an anti-CD30 antibody, an anti-CD33 antibody, an anti-CD52 antibody, an anti-CD79B antibody, an anti-EGFR antibody, an anti-HER2 antibody, an anti-VEGFR2 antibody, an anti-GD2 antibody, an anti-Nectin 4 antibody and an anti-Trop-2 antibody.

13. The method of claim 1, wherein administration of the IL-15/IL-15Rα agonist in step (i) results in (1) an increase of the % of Ki-67$^+$ NK of total NK cells in comparison to no administration of the IL-2/IL-15Rα agonist, and wherein administration of the IL-2/IL-15Rα agonist after the first repetition results in a Ki-67$^+$ NK cell level that is at least 70% of the of the Ki-67$^+$ NK cells of step (i), (2) maintenance of NK cell numbers or an increase of NK cell numbers to at least 110% as compared to no administration of IL-2/IL-15Rα agonist after at least one repetition of the period (i), after at least two repetitions of the period (i), and/or (3) NK cell numbers of at least $1.1 \times 10^3$ NK cells/ul after at least one repetition of the period (i), or after at least two repetitions of the first period.

14. The method of claim 1, wherein the IL-15/IL-15Rα agonist is an IL-15/interleukin-15 receptor alpha (IL-15Rα) complex, a fusion protein comprising the human IL-15Rα sushi domain or derivative thereof, a flexible linker and the human IL-15 or derivative thereof.

15. The method of claim 14, wherein the human IL-15Rα sushi domain comprises the sequence of SEQ ID NO: 6, the human IL-15 comprises the sequence of SEQ ID NO: 4, and the IL-15/IL-15Rα complex comprises the sequence of SEQ ID NO: 9.

16. The method of claim 1, further comprising administering a therapeutic agent in combination with the IL-2/IL-15Rα agonist.

17. The method of claim 16, wherein the therapeutic agent is a checkpoint inhibitor comprising an anti-PD-1 antibody, an anti-PD-L1 antibody, an anti-PD-L2 antibody, an anti-LAG-3 antibody, an anti-TIM-3 antibody, an anti-CTLA4 antibody or an anti-TIGIT antibody.

18. The method of claim 16, wherein the therapeutic agent is a therapeutic antibody comprising from an anti-CD38 antibody, an anti-CD19 antibody, an anti-CD20 antibody, an anti-CD30 antibody, an anti-CD33 antibody, an anti-CD52 antibody, an anti-CD79B antibody, an anti-EGFR antibody, an anti-HER2 antibody, an anti-VEGFR2 antibody, an anti-GD2 antibody, an anti-Nectin 4 antibody and an anti-Trop-2 antibody.

* * * * *

SEQUENCE LISTING

<160> NUMBER OF SEQ ID NOS: 13

<210> SEQ ID NO 1
<211> LENGTH: 153
<212> TYPE: PRT
<213> ORGANISM: Homo sapiens

<400> SEQUENCE: 1

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45
```

```
Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 3
<211> LENGTH: 162
<212> TYPE: PRT
<213> ORGANISM: Homo sapiens

<400> SEQUENCE: 3

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80
```

-continued

```
Pro Ser Cys Lys Val Thr Ala Met Lys Cys Phe Leu Leu Glu Leu Gln
                85              90              95

Val Ile Ser Leu Glu Ser Gly Asp Ala Ser Ile His Asp Thr Val Glu
            100             105             110

Asn Leu Ile Ile Leu Ala Asn Asn Ser Leu Ser Ser Asn Gly Asn Val
            115             120             125

Thr Glu Ser Gly Cys Lys Glu Cys Glu Glu Leu Glu Glu Lys Asn Ile
        130             135             140

Lys Glu Phe Leu Gln Ser Phe Val His Ile Val Gln Met Phe Ile Asn
145                 150             155                 160

Thr Ser

<210> SEQ ID NO 4
<211> LENGTH: 114
<212> TYPE: PRT
<213> ORGANISM: Homo sapiens

<400> SEQUENCE: 4

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20              25              30

Pro Ser Cys Lys Val Thr Ala Met Lys Cys Phe Leu Leu Glu Leu Gln
            35              40              45

Val Ile Ser Leu Glu Ser Gly Asp Ala Ser Ile His Asp Thr Val Glu
        50              55              60

Asn Leu Ile Ile Leu Ala Asn Asn Ser Leu Ser Ser Asn Gly Asn Val
65              70              75                  80

Thr Glu Ser Gly Cys Lys Glu Cys Glu Glu Leu Glu Glu Lys Asn Ile
                85              90              95

Lys Glu Phe Leu Gln Ser Phe Val His Ile Val Gln Met Phe Ile Asn
            100             105             110

Thr Ser

<210> SEQ ID NO 5
<211> LENGTH: 267
<212> TYPE: PRT
<213> ORGANISM: Homo sapiens

<400> SEQUENCE: 5

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
                20              25              30

Cys Pro Pro Pro Met Ser Val Glu His Ala Asp Ile Trp Val Lys Ser
            35              40              45

Tyr Ser Leu Tyr Ser Arg Glu Arg Tyr Ile Cys Asn Ser Gly Phe Lys
        50              55              60

Arg Lys Ala Gly Thr Ser Ser Leu Thr Glu Cys Val Leu Asn Lys Ala
65              70              75                  80

Thr Asn Val Ala His Trp Thr Thr Pro Ser Leu Lys Cys Ile Arg Asp
                85              90              95

Pro Ala Leu Val His Gln Arg Pro Ala Pro Pro Ser Thr Val Thr Thr
            100             105             110

Ala Gly Val Thr Pro Gln Pro Glu Ser Leu Ser Pro Ser Gly Lys Glu
            115             120             125
```

-continued

```
Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
            195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

<210> SEQ ID NO 6
<211> LENGTH: 61
<212> TYPE: PRT
<213> ORGANISM: Homo sapiens

<400> SEQUENCE: 6

```
Cys Pro Pro Pro Met Ser Val Glu His Ala Asp Ile Trp Val Lys Ser
1                 5                   10                  15

Tyr Ser Leu Tyr Ser Arg Glu Arg Tyr Ile Cys Asn Ser Gly Phe Lys
                20                  25                  30

Arg Lys Ala Gly Thr Ser Ser Leu Thr Glu Cys Val Leu Asn Lys Ala
            35                  40                  45

Thr Asn Val Ala His Trp Thr Thr Pro Ser Leu Lys Cys
    50                  55                  60
```

<210> SEQ ID NO 7
<211> LENGTH: 77
<212> TYPE: PRT
<213> ORGANISM: Homo sapiens

<400> SEQUENCE: 7

```
Ile Thr Cys Pro Pro Pro Met Ser Val Glu His Ala Asp Ile Trp Val
1                 5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro
65                  70                  75
```

<210> SEQ ID NO 8
<211> LENGTH: 20
<212> TYPE: PRT
<213> ORGANISM: Artificial Sequence
<220> FEATURE:
<223> OTHER INFORMATION: Linker Sequence

<400> SEQUENCE: 8

Ser Gly Gly Ser Gly Gly Gly Ser Gly Gly Gly Ser Gly Gly Gly
1               5                   10                  15

Gly Ser Gly Gly
            20

<210> SEQ ID NO 9
<211> LENGTH: 211
<212> TYPE: PRT
<213> ORGANISM: Artificial Sequence
<220> FEATURE:
<223> OTHER INFORMATION: RLI2

<400> SEQUENCE: 9

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Gly Gly
65                  70                  75                  80

Ser Gly Gly Gly Gly Ser Gly Gly Gly Ser Gly Gly Gly Ser Gly
            85                  90                  95

Gly Asn Trp Val Asn Val Ile Ser Asp Leu Lys Lys Ile Glu Asp Leu
            100                 105                 110

Ile Gln Ser Met His Ile Asp Ala Thr Leu Tyr Thr Glu Ser Asp Val
            115                 120                 125

His Pro Ser Cys Lys Val Thr Ala Met Lys Cys Phe Leu Leu Glu Leu
    130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
                165                 170                 175

Val Thr Glu Ser Gly Cys Lys Glu Cys Glu Glu Leu Glu Glu Lys Asn
            180                 185                 190

Ile Lys Glu Phe Leu Gln Ser Phe Val His Ile Val Gln Met Phe Ile
            195                 200                 205

Asn Thr Ser
    210

<210> SEQ ID NO 10
<211> LENGTH: 133
<212> TYPE: PRT
<213> ORGANISM: Homo sapiens

<400> SEQUENCE: 10

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

-continued

```
Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
    130
```

```
<210> SEQ ID NO 11
<211> LENGTH: 20
<212> TYPE: PRT
<213> ORGANISM: Artificial Sequence
<220> FEATURE:
<223> OTHER INFORMATION: Leader peptide of (IL-15N72D)2:IL-15Ra sushi-Fc

<400> SEQUENCE: 11

Met Glu Thr Asp Thr Leu Leu Leu Trp Val Leu Leu Leu Trp Val Pro
1               5                   10                  15

Gly Ser Thr Gly
            20
```

```
<210> SEQ ID NO 12
<211> LENGTH: 297
<212> TYPE: PRT
<213> ORGANISM: Artificial Sequence
<220> FEATURE:
<223> OTHER INFORMATION: IL-15Ra sushi (65aa)-Fc (IgG1 CH2-CH3)

<400> SEQUENCE: 12

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
```

-continued

```
            195              200              205

Thr Lys Asn Gln Val Ser Leu Thr Cys Leu Val Lys Gly Phe Tyr Pro
    210              215              220

Ser Asp Ile Ala Val Glu Trp Glu Ser Asn Gly Gln Pro Glu Asn Asn
225              230              235              240

Tyr Lys Thr Thr Pro Pro Val Leu Asp Ser Asp Gly Ser Phe Phe Leu
                245              250              255

Tyr Ser Lys Leu Thr Val Asp Lys Ser Arg Trp Gln Gln Gly Asn Val
                260              265              270

Phe Ser Cys Ser Val Met His Glu Ala Leu His Asn His Tyr Thr Gln
                275              280              285

Lys Ser Leu Ser Leu Ser Pro Gly Lys
    290              295
```

```
<210> SEQ ID NO 13
<211> LENGTH: 114
<212> TYPE: PRT
<213> ORGANISM: Artificial Sequence
<220> FEATURE:
<223> OTHER INFORMATION: IL-15N72D

<400> SEQUENCE: 13

Asn Trp Val Asn Val Ile Ser Asp Leu Lys Lys Ile Glu Asp Leu Ile
1               5               10              15

Gln Ser Met His Ile Asp Ala Thr Leu Tyr Thr Glu Ser Asp Val His
                20              25              30

Pro Ser Cys Lys Val Thr Ala Met Lys Cys Phe Leu Leu Glu Leu Gln
        35              40              45

Val Ile Ser Leu Glu Ser Gly Asp Ala Ser Ile His Asp Thr Val Glu
    50              55              60

Asn Leu Ile Ile Leu Ala Asn Asp Ser Leu Ser Ser Asn Gly Asn Val
65              70              75              80

Thr Glu Ser Gly Cys Lys Glu Cys Glu Glu Leu Glu Glu Lys Asn Ile
                85              90              95

Lys Glu Phe Leu Gln Ser Phe Val His Ile Val Gln Met Phe Ile Asn
                100             105             110

Thr Ser
```